US008173136B2

(12) United States Patent
Cho et al.

(10) Patent No.: US 8,173,136 B2
(45) Date of Patent: May 8, 2012

(54) ATTENUATED RECOMBINANT NEWCASTLE DISEASE VIRUS AND VACCINE CONTAINING THE SAME

(75) Inventors: Sun-Hee Cho, Seongnam-si (KR); Hyuk-Joon Kwon, Seoul (KR); Sun-Joong Kim, Gwacheon-si (KR); Tae-Eun Kim, Seoul (KR); Young-Jin An, Gwangmyeong-si (KR); Mi-Joung Ko, Shiheung-shi (KR); Il-Hwan Kim, Seoul (KR); Young-Ho Park, Chungcheongnam-do (KR); Chae-Hyun Kim, Chungcheongnam-do (KR); Jang-Hyuck Han, Chungcheongnam-do (KR); Tae-Hwan Kim, Chungcheongnam-do (KR)

(73) Assignees: KBNP, Inc., Dugok-Ri, Sinam-Myeon, Chungcheongnam-Do, Yesan-Gun (KR); Biopoa, Inc., Gwonsun-Gu, Kyunggi-Do, Suwon-Si (KR)

( * ) Notice: Subject to any disclaimer, the term of this patent is extended or adjusted under 35 U.S.C. 154(b) by 112 days.

(21) Appl. No.: 12/442,749

(22) PCT Filed: Sep. 27, 2006

(86) PCT No.: PCT/KR2006/003837
§ 371 (c)(1),
(2), (4) Date: Apr. 20, 2009

(87) PCT Pub. No.: WO2008/038845
PCT Pub. Date: Apr. 3, 2008

(65) Prior Publication Data

US 2010/0183664 A1 Jul. 22, 2010

(30) Foreign Application Priority Data

Sep. 26, 2006 (KR) ........................ 10-2006-0093620

(51) Int. Cl.
*A61K 39/17* (2006.01)
*C12N 7/01* (2006.01)

(52) U.S. Cl. ............... 424/199.1; 424/214.1; 424/205.1; 435/235.1

(58) Field of Classification Search ........................ None
See application file for complete search history.

(56) References Cited

U.S. PATENT DOCUMENTS

| | | | | |
|---|---|---|---|---|
| 6,146,642 | A * | 11/2000 | Garcia-Sastre et al. | 424/214.1 |
| 6,451,323 | B1 * | 9/2002 | Garcia-Sastre et al. | 424/214.1 |
| 6,699,479 | B1 | 3/2004 | Mebatsion et al. | |
| 6,719,979 | B2 * | 4/2004 | Peeters et al. | 424/214.1 |

FOREIGN PATENT DOCUMENTS

| | | |
|---|---|---|
| WO | 00/67786 | 11/2000 |
| WO | WO 00/67786 | * 11/2000 |
| WO | 02/36617 | 5/2002 |
| WO | WO 2007/108568 | * 9/2007 |

OTHER PUBLICATIONS

Wakamatsu et al (Virology 353:333-343, Jul. 24, 2006).*

Peeters et al (Vaccine 19:1616-1627, 2001).*

DeLeeuw et al (Journal of General Virology 84:475-484, 2003).*

Alamares et al (Journal of Clinical Microbiology 43:4229-4233, 2005).*

Gould et al Avian Pathology 32:361-373, 2003).*

Mebatsion, T. et al.: 'A recombinant Newcastle disease virus with low-level V protein expression is immunogenic and lacks pathogenicity for chicken embryos'; Journal of Virology. vol. 75(1), pp. 420-428 (Jan. 2001).

Peeters, B. P. H. et al.: 'Generation of a recombinant chimeric Newcastle disease virus vaccine that allows serological differentiation between vaccinated and infected animals'; Vaccine, vol. 19, pp. 1616-1627 (Feb. 8, 2001).

Mebatsion, T. et al.: 'Newcastle disease virus (NDV) marker vaccine: an immunodominant epitope on the nucleoprotein gene of NDV can be deleted or replaced by a foreign epitope'; Journal of Virology, vol. 76(20), pp. 10138-10146 (Oct. 2002).

De Leeuw, O. S. et al.: 'Effect of fusion protein cleavage site mutations on virulence of Newcastle disease virus: non-virulent cleavage site mutants revert to virulence after one passage in chicken brain'; Journal of General Virology, vol. 84, pp. 475-484 (Feb. 2003).

Wakamatsu N et al., The pathogenesis of Newcastle disease: A comparis on of selected Newcastle disease virus wild-type strains and their infectious clones, virology[online], ,http://ddr.nal.usda.gov/bitstream/10113/28551/1/IND43922943.pdf>, published on Jul. 24, 2006.

Judith G. Alamares, et al., "Monoclonal Antibody Routinely Used to Identify Avirulent Strains of Newcastle Disease Virus Binds to an Epitope at the Carboxy Terminus of the Hemagglutinin-Neuraminidase Protein and Recognizes Individual Mesogenic and Velogenic Strains", J Clin Microbiol., Aug. 2005, vol. 43, p. 4229-4223.

* cited by examiner

*Primary Examiner* — Mary E Mosher
(74) *Attorney, Agent, or Firm* — Lexyoume IP Group, PLLC.

(57) ABSTRACT

The present invention relates to a recombinant vector for transcription of the Newcastle disease virus (NDV) genome, a strain of attenuated recombinant NDV with a surface antigen of pathogenic NDV prepared by the vector, a method of preparing a recombinant NDV having low pathogenicity and high protectivity efficiency against Newcastle disease (ND) using the vector, and a vaccine against ND containing the recombinant NDV.

10 Claims, 26 Drawing Sheets

FIG. 4

TM p1 (linker) 5-GAATTCTTAATACGACTCACTATAGGaccaaGAGACGGGC-3 (SEQ ID NO: 94)
TM p2 (linker) 5-CCatATCGATTCGCGACCGCGGgatACTAGTCGTACGCCT-3 (SEQ ID NO: 95)
TM p3 (linker) 5-GCGGTCGCGAATCGATATGGGCCCGTCTCTTGGTCCTATA-3 (SEQ ID NO: 96)
TM p4 (linker) 5-CATATGCTCTACCAAGAGACCCCTAGGCGTACGACTAGTATCCC-3 (SEQ ID NO: 97)

HDV F 5-GGTCTCTtggtGGGTCGGCATGGCATCTCCA-3 (SEQ ID NO: 98)
HDV R 5-CATATGCAAAAAACCCCTCAAGACCCGT-3 (SEQ ID NO: 99)

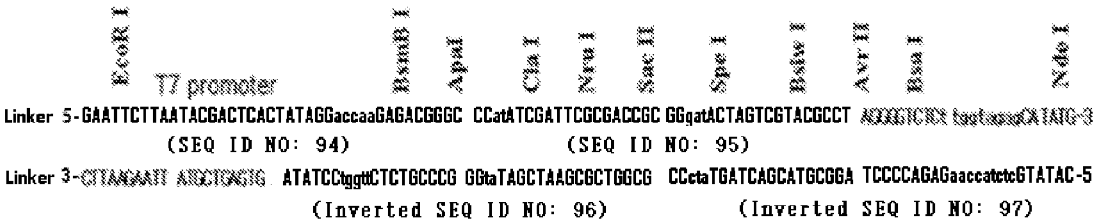

(a part of SEQ ID NO: 84)

FIG. 7

(SEQ ID NO: 84)

GAATTCTAATACGACTCACTATAGGaccaaGAGACGGGCCCatATCGATTCGCGACCGCGGgatACTAGTCGTACGCCTAGGGGTCTCtt
ggtGGGTCGGCATGGCATCTCCACCTCCTCGCGGTCCGACCTGGGCATCCGAAGGAGGACGTCGTCCACTCGGATGGCTAAGGGAGAGCt
cggatccggctgctaacaaagcccgaaaggaagctgagttggctgctgccaccgctgagcaataaCTAGCATAACCCCTTGGGGCCTCTA
AACGGGTCTTGAGGGGTTTTTTGCATATGCGGTGTGAAATACCGCACAGATGCGTAAGGAGAAAATACCGCATCAGGCGCTCTTCCGCTT
CCTCGCTCACTGACTCGCTGCGCTCGGTCGTTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTAAAAAGGCCGCGTTGCTGGCGTTTTTCCATA
GGCTCCGCCCCCCTGACGAGCATCACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTATCTCAGCGATCTGTCTATTTCGTTCATCCA
TAGTTGCCTGACTCCCCGTCGTGTAGATAACTACGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAATAGTTTGCGCAACGTTGTTGCCATTGCTGCAGGCATCGTGG
TGTCACGCTCGTCGTTTGGTATGGCTTCATTCAGCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATGGCAGCACTGCATAATTCTC
TTACTGTCATGCCATCCGTAAGATGCTTTTCTGTGACTGGTGAGTACTCAACCAAGTCATTCTGAGAATAGTGTATGCGGCGACCGAGTT
GCTCTTGCCCGGCGTCAACACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCTTTTACTTTCACCA
GCGTTTCTGGGTGAGCAAAAACAGGAAGGCAAAATGCCGCAAAAAAGGGAATAAGGGCGACACGGAAATGTTGAATACTCATACTCTTCC
TTTTTCAATATTATTGAAGCATTTATCAGGGTTATTGTCTCATGAGCGGATACATATTTGAATGTATTTAGAAAAATAAACAAATAGGGG
TTCCGCGCACATTTCCCCGAAAAGTGCCACCTGACGTCTAAGAAACCATTATTATCATGACATTAACCTATAAAAATAGGCGTATCACGA
GGCCCTTTCGTCTTCAA

FIG. 10A

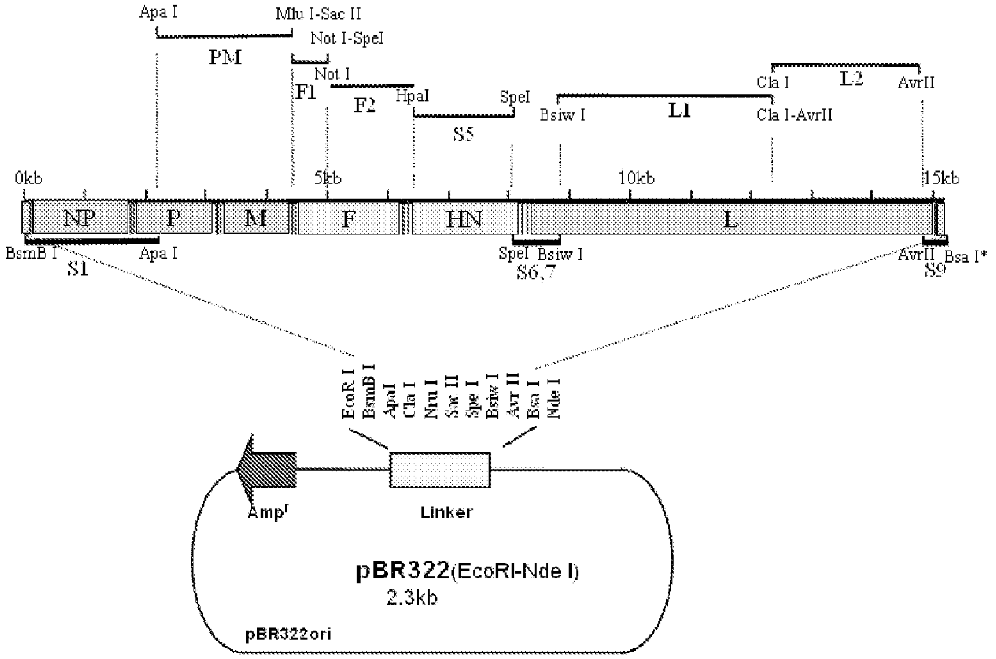

>S2-F aaaagggcccatggtcgagccc (SEQ ID NO: 38)
ApaI

>La-MR ccgcgg acgcgtgttttttctaacttgatagac
SacII MluI
(SEQ ID NO: 86)

>ND-F1S acgcgtacgggtagaagagtctggatcc
MluI
(SEQ ID NO: 87)

>ND-F1R actagt gcggccgctgctgttatctgtgc
SpeI NotI
(SEQ ID NO: 88)

>ND-F2F gcggccgcCCTAATACAAGCCAACCag
NotI
(SEQ ID NO: 89)

>S5-R ctcaactagtaagggaacgatcctaaattcc (SEQ ID NO: 45)
SpeI

>La-L1F ttcgtacggatccggcattctggtttcac (SEQ ID NO: 90)
BriWI

>La-L1R cctaggttatcgatcgattagagataaaccc
AvrII ClaI
(SEQ ID NO: 91)

>La-L2F gagaatcgatatttccaatgacaacaaccagg
ClaI
(SEQ ID NO: 92)

>La-L2R cctaggacagccttcaaatatttagg (SEQ ID NO: 93)
AvrII

FIG. 13

(a Part of SEQ ID NO: 1)

```
TACAATCCTTTTAAGAAATAAGCTGCGTCTCTGAGATTGCGCTCCGCCCACTCACCCAGA     La Sota
TCATCATGACACAAAAAACTAATCTGTCTTGATTATTTACAGTTAGTTTACCTGTCTATC   genome sequence
AAGTTAGAAAAAACACGGGTAGAAGAGTCTGGATCCCGACCGGCACATTCAGGACGCAAT     KBNP-4152
ATGGgCTCCAAACTTTCTACCAGGATTCCAGCACCTCTGATGCTGACCACCCGGATTACG   genome sequence
CTGATATTGAGCTGTATCCGTCCGACAAGCTCTCTTGACGGCAGGCCTCTTGCAGCTGCA
GGAATTGTAGTAACAGGAGATAAGGCAGTCAATGTATACACCTCGTCTCAGACAGGGTCA
ATCATAGTCAAGTTGCTCCCGAATATGCCCAGGGATAAAGAGGCGTGTGCAAAAGCCCCA
TTAGAGGCATATAACAGAACACTGACTACTTTGCTAACTCCTCTTGGCGACTCCATCCGC
AAGATCCAAGGGTCTGTGTCCACGTCTGGAGGAAGGAGACAAAAACGCTTTATAGGTGCT
                                 R  R  Q  K  R  F
                                 G  K  Q  G  R  L
                                 G  A  Q  A  R  L  Not I
GTTATTGGCAGTGTAGCTCTTGGGGTTGCAACAGCGGCACAGATAACAGCAGCGGCCGCC
CTAATACAA
```

FIG. 14

(a part of SEQ ID NO: 1)

```
                         (SEQ ID NO: 100) S41-P1→
TACAATCCTT TTAAGAAATA AGCTGCGTCT CTGAGATTGC GCT CCGCCCA CTCACCCAGA
ATGTTAGGAA AATTCTTTAT TCGACGCAGA GACTCTAACG CGA GGCGGGT GAGTGGGTCT
                         ←S41-P2 (SEQ ID NO: 110)

          (SEQ ID NO: 101) S41-P3→
TCATCATGAC ACAAAAAACT AATCTGTCTT G ATTATTTAC AGTTAGTTTA CCTGT CTATC
AGTAGTACTG TGTTTTTTGA TTAGACAGAA C TAATAAATG TCAATCAAAT GGACA GATAG
    →  ←S41-P4 (SEQ ID NO: 111)                               ←S41-P6

(SEQ ID NO: 102)
            S41-P5 →                      (SEQ ID NO: 103) S41-P7
AAGTTAGAAA AAACACGGGT AGAAAGAGTCT GGATCCCGAC CG GCACATTC AGGACGCAAT
TTCAATCTTT TTTGTGCCCA TCTTCTCAGA CCTAGGGCTG GC CGTGTAAG TCCTGCGTTA
(SEQ ID NO: 112)                                 ←S41-P8
                                              (SEQ ID NO: 113)

  →
ATGGgCTCCA AACTTTCTAC CAGGATTCCA G CACCTCTGA TGCTGACCAC CCGGATTACG
TACCcGAGGT TTGAAAGATG GTCCTAAGGT C GTGGAGACT ACGACTGGTG GGCCTAATGC
                                  →
CTGATATTGA GCTGTATCCG TCCGACAAGC TCTCTTGACG GCAGGCCTCT TGCAGCTGCA
GACTATAACT CGACATAGGC AGGCTGTTCG AGAGAACTGC CGTCCGGAGA ACGTCGACGT

GGAATTGTAG TAACAGGAGA TAAGGCAGTC AATGTATACA CCTCGTCTCA GACAGGGTCA
CCTTAACATC ATTGTCCTCT ATTCCGTCAG TTACATATGT GGAGCAGAGT CTGTCCCAGT
                                    ←
ATCATAGTCA AGTTGCTCCC GAATATGCCC AGGGATAAAG AGGCGTGTGC AAAAGCCCCA
TAGTATCAGT TCAACGAGGG CTTATACGGG TCCCTATTTC TCCGCACACG TTTTCGGGGT
                                                              ←
(SEQ ID NO: 104)
               S41-P9→
TTAGAGGCAT ATAACAGAACAC TGACTACT TTGCTAACTC CTCTTGGCGA CTCCATCCGC
AATCTCCGTA TATTGTCTTGTG ACTGATGA AACGATTGAG GAGAACCGCT GAGGTAGGCG
S41-P10 (SEQ ID NO: 114)                           →  ←S41-P12
                                                   (SEQ ID NO: 115)

(SEQ ID NO: 105)                          (SEQ ID NO: 106, 107, 108)
  S41-P11→                                     S41-P13(1,2,3)→
AAGATCCAAGG GTCTGTGTC CACGTCTGGA GGA AGGAGACAAAAACGCTTTATAGGT GCT(RRQKRF)
                                     GGCAGACAAGCACGCCTGATAGGT GCT(GRQARL)
                                     GGCGGCCAAGCACGCCTGATAGGT GCT(GGQARL)
TTCTAGGTTC CCAGACACAG GTGCAGACCT CCT TCCTCTGTTTTTGCGAAATATCCA CGA( 9/24)
                                 CCT CCGTCTGTTCGTGCGGACTATCCA CGA(14/22)
                                 CCT CCGCCGGTTCGTGCGGACTATCCA CGA(15/22)
                                   ←S41-P14(1,2,3)
                                    (SEQ ID NO: 116, 117, 118)

     (11/23)     (SEQ ID NO: 109) S41-P15 →         Not I
GTTATTGGCA GTGTAGCTCT TGGGGTTGCA ACAGCGGCAC AGATAACAGC AGCGGCCGCC
CAATAACCGT CACATCGAGA ACCCCAACGT TGTCGCCGTG TCTATTGTCG TCGCCGGCGG
                         ←S41-P16 (SEQ ID NO: 119)
CTAATACAA
GATTATGTT
```

FIG. 15

(SEQ ID NO: 85)

```
   P1                                                                   P3
cccttt ACTA GTTGAGATTC TCAAGGATGA TGGGGTTAGG GAGGCCAGGG CTGGCCG TT
gggaaatgat caactctaag agttcctact accccaatcc ctccggtccc gaccggcgaa
                                         P2

                                                            P5
GAGTCAATTG CGAGAGGGTT GGAAAGATGA CATTGTATCA CCTATCTTTT GCGACGCCAA
ctcagttaac gctctcccaa cctttctact gtaacatagt ggatagaaaa cgctgcggtt
                          P4

                                                          P7
GAATCAAACT GAGTACCGGC GTGAGCTCGA GTCTTACGCT GCCAGCTGGC CA   TCAGC
cttagtttga ctcatggccg cactcgagct cagaatgcga cggtcgaccg gtattagtcg
                      P6

                                                     P9
TAGCGCTAAT GTGATTAGAT TAAATCTTGT CG ATAGTCAC TTGATTAAGA AAAAATGTAA
atcgcgatta cactaatcta atttagaaca gc tatcagtg aactaattct ttttacatt
                P8

GTGGCAATGA GATACAAGGC AAAACAGCTC ATGGTAAATA ATACGGGTAG GACATGGCGA
caccgttact ctatgttccg ttttgtcgag taccatttat tatgcccatc ctgtaccgct
P10
```

1: RT(-)ve ND-com
2: RT(-)ve ND-patho
M: 100bp DNA ladder
3: C4152-R2L ND-com
4: C4152-R2L ND-patho A. Normal CEF
B. La Sota
C. KBNP-4152
D. KBNP-C4152-R2L
E. KBNP-C4152-R2L

```
                         SEQUENCE LISTING


<160> NUMBER OF SEQ ID NOS: 123

<210> SEQ ID NO 1
<211> LENGTH: 17481
<212> TYPE: DNA
<213> ORGANISM: Artificial Sequence
<220> FEATURE:
<223> OTHER INFORMATION: Nucleotide sequence of full length genomic
      clone of pTMH c4152-R2L
<220> FEATURE:
<221> NAME/KEY: CDS
<222> LOCATION: (122)..(1588)
<223> OTHER INFORMATION: NP protein coding site
<220> FEATURE:
<221> NAME/KEY: CDS
<222> LOCATION: (1887)..(3071)
<223> OTHER INFORMATION: P protein coding site
<220> FEATURE:
<221> NAME/KEY: CDS
<222> LOCATION: (3290)..(4381)
<223> OTHER INFORMATION: M protein coding site
<220> FEATURE:
<221> NAME/KEY: CDS
<222> LOCATION: (4550)..(6208)
<223> OTHER INFORMATION: F protein coding site
<220> FEATURE:
<221> NAME/KEY: CDS
<222> LOCATION: (6418)..(8148)
<223> OTHER INFORMATION: HN protein coding site
<220> FEATURE:
<221> NAME/KEY: CDS
<222> LOCATION: (8387)..(14998)
<223> OTHER INFORMATION: L protein coding site

<400> SEQUENCE: 1

accaaacaga gaatccgtga gttacgataa aaggcgaagg agcaattgaa gtcgcacggg     60

tagaaggtgt gaatctcgag tgcgagcccg aagcacaaac tcgagaaagc cttctgccaa    120

c          atg tct tcc gta ttt gat gag tac gaa cag ctc ctc gcg gct   163
           Met Ser Ser Val Phe Asp Glu Tyr Glu Gln Leu Leu Ala Ala
             1               5                  10

cag act cgc ccc aat gga gct cat gga ggg gga gaa aaa ggg agt acc      211
Gln Thr Arg Pro Asn Gly Ala His Gly Gly Gly Glu Lys Gly Ser Thr
 15                  20                  25                  30

tta aaa gta gac gtc ccg gta ttc act ctt aac agt gat gac cca gaa      259
Leu Lys Val Asp Val Pro Val Phe Thr Leu Asn Ser Asp Asp Pro Glu
                 35                  40                  45

gat aga tgg agc ttt gtg gta ttc tgc ctc cgg att gct gtt agc gaa      307
Asp Arg Trp Ser Phe Val Val Phe Cys Leu Arg Ile Ala Val Ser Glu
             50                  55                  60

gat gcc aac aaa cca ctc agg caa ggt gct ctc ata tct ctt tta tgc      355
Asp Ala Asn Lys Pro Leu Arg Gln Gly Ala Leu Ile Ser Leu Leu Cys
         65                  70                  75

tcc cac tca cag gta atg agg aac cat gtt gcc att gca ggg aaa cag      403
Ser His Ser Gln Val Met Arg Asn His Val Ala Ile Ala Gly Lys Gln
     80                  85                  90

aat gaa gcc aca ttg gcc gtg ctt gag att gat ggc ttt gcc aac ggc      451
```

-continued

```
Asn Glu Ala Thr Leu Ala Val Leu Glu Ile Asp Gly Phe Ala Asn Gly
 95                 100                 105                 110

acg ccc cag ttc aac aat agg agt gga gtg tct gaa gag aga gca cag      499
Thr Pro Gln Phe Asn Asn Arg Ser Gly Val Ser Glu Glu Arg Ala Gln
                115                 120                 125

aga ttt gcg atg ata gca gga tct ctc cct cgg gca tgc agc aac gga      547
Arg Phe Ala Met Ile Ala Gly Ser Leu Pro Arg Ala Cys Ser Asn Gly
            130                 135                 140

acc ccg ttc gtc aca gcc ggg gca gaa gat gat gca cca gaa gac atc      595
Thr Pro Phe Val Thr Ala Gly Ala Glu Asp Asp Ala Pro Glu Asp Ile
        145                 150                 155

acc gat acc ctg gag agg atc ctc tct atc cag gct caa gta tgg gtc      643
Thr Asp Thr Leu Glu Arg Ile Leu Ser Ile Gln Ala Gln Val Trp Val
    160                 165                 170

aca gta gca aaa gcc atg act gcg tat gag act gca gat gag tcg gaa      691
Thr Val Ala Lys Ala Met Thr Ala Tyr Glu Thr Ala Asp Glu Ser Glu
175                 180                 185                 190

aca agg cga atc aat aag tat atg cag caa ggc agg gtc caa aag aaa      739
Thr Arg Arg Ile Asn Lys Tyr Met Gln Gln Gly Arg Val Gln Lys Lys
                195                 200                 205

tac atc ctc tac ccc gta tgc agg agc aca atc caa ctc acg atc aga      787
Tyr Ile Leu Tyr Pro Val Cys Arg Ser Thr Ile Gln Leu Thr Ile Arg
            210                 215                 220

cag tct ctt gca gtc cgc atc ttt ttg gtt agc gag ctc aag aga ggc      835
Gln Ser Leu Ala Val Arg Ile Phe Leu Val Ser Glu Leu Lys Arg Gly
        225                 230                 235

cgc aac acg gca ggt ggt acc tct act tat tat aac ctg gta ggg gac      883
Arg Asn Thr Ala Gly Gly Thr Ser Thr Tyr Tyr Asn Leu Val Gly Asp
    240                 245                 250

gta gac tca tac atc agg aat acc ggg ctt act gca ttc ttc ttg aca      931
Val Asp Ser Tyr Ile Arg Asn Thr Gly Leu Thr Ala Phe Phe Leu Thr
255                 260                 265                 270

ctc aag tac gga atc aac acc aag aca tca gcc ctt gca ctt agt agc      979
Leu Lys Tyr Gly Ile Asn Thr Lys Thr Ser Ala Leu Ala Leu Ser Ser
                275                 280                 285

ctc tca ggc gac atc cag aag atg aag cag ctc atg cgt ttg tat cgg     1027
Leu Ser Gly Asp Ile Gln Lys Met Lys Gln Leu Met Arg Leu Tyr Arg
            290                 295                 300

atg aaa gga gat aat gcg ccg tac atg aca tta ctt ggt gat agt gac     1075
Met Lys Gly Asp Asn Ala Pro Tyr Met Thr Leu Leu Gly Asp Ser Asp
        305                 310                 315

cag atg agc ttt gcg cct gcc gag tat gca caa ctt tac tcc ttt gcc     1123
Gln Met Ser Phe Ala Pro Ala Glu Tyr Ala Gln Leu Tyr Ser Phe Ala
    320                 325                 330

atg ggt atg gca tca gtc cta gat aaa ggt act ggg aaa tac caa ttt     1171
Met Gly Met Ala Ser Val Leu Asp Lys Gly Thr Gly Lys Tyr Gln Phe
335                 340                 345                 350

gcc agg gac ttt atg agc aca tca ttc tgg aga ctt gga gta gag tac     1219
Ala Arg Asp Phe Met Ser Thr Ser Phe Trp Arg Leu Gly Val Glu Tyr
                355                 360                 365

gct cag gct cag gga agt agc att aac gag gat atg gct gcc gag cta     1267
Ala Gln Ala Gln Gly Ser Ser Ile Asn Glu Asp Met Ala Ala Glu Leu
            370                 375                 380

aag cta acc cca gca gca atg aag ggc ctg gca gct gct gcc caa cgg     1315
Lys Leu Thr Pro Ala Ala Met Lys Gly Leu Ala Ala Ala Ala Gln Arg
        385                 390                 395

gtc tcc gac gat acc agc agc ata tac atg cct act caa caa gtc gga     1363
Val Ser Asp Asp Thr Ser Ser Ile Tyr Met Pro Thr Gln Gln Val Gly
    400                 405                 410

gtc ctc act ggg ctt agc gag ggg ggg tcc caa gct cta caa ggc gga     1411
```

-continued

```
Val Leu Thr Gly Leu Ser Glu Gly Gly Ser Gln Ala Leu Gln Gly Gly
415                 420                 425                 430

tcg aat aga tcg caa ggg caa cca gaa gcc ggg gat ggg gag acc caa     1459
Ser Asn Arg Ser Gln Gly Gln Pro Glu Ala Gly Asp Gly Glu Thr Gln
                435                 440                 445

ttc ctg gat ctg atg aga gcg gta gca aat agc atg agg gag gcg cca     1507
Phe Leu Asp Leu Met Arg Ala Val Ala Asn Ser Met Arg Glu Ala Pro
            450                 455                 460

aac tct gca cag ggc act ccc caa tcg ggg cct ccc cca act cct ggg     1555
Asn Ser Ala Gln Gly Thr Pro Gln Ser Gly Pro Pro Pro Thr Pro Gly
        465                 470                 475

cca tcc caa gat aac gac acc gac tgg ggg tat         tg atggacaaaa   1600
Pro Ser Gln Asp Asn Asp Thr Asp Trp Gly Tyr
    480                 485

cccagcctgc ttccacaaaa acatcccaat gccctcaccc gtagtcgacc cctcgatttg   1660

cggctctata tgaccacacc ctcaaacaaa catccccctc tttcctccct ccccctgctg   1720

tacaactccg cacgccctag ataccacagg cacaatgcgg ctcactaaca atcaaaacag   1780

agccgaggga attagaaaaa agtacgggta gaagagggat attcagagat cagggcaagt   1840

ctcccgagtc tctgctctct cctctacctg atagaccagg acaaac     atg gcc acc   1895
                                                       Met Ala Thr
                                                         1

ttt aca gat gca gag atc gac gag cta ttt gag aca agt gga act gtc     1943
Phe Thr Asp Ala Glu Ile Asp Glu Leu Phe Glu Thr Ser Gly Thr Val
      5                  10                  15

att gac aac ata att aca gcc cag ggt aaa cca gca gag act gtt gga     1991
Ile Asp Asn Ile Ile Thr Ala Gln Gly Lys Pro Ala Glu Thr Val Gly
 20                  25                  30                  35

agg agt gca atc cca caa ggc aag acc aag gtg ctg agc gca gca tgg     2039
Arg Ser Ala Ile Pro Gln Gly Lys Thr Lys Val Leu Ser Ala Ala Trp
                 40                  45                  50

gag aag cat ggg agc atc cag cca ccg gcc agt caa gac aac ccc gat     2087
Glu Lys His Gly Ser Ile Gln Pro Pro Ala Ser Gln Asp Asn Pro Asp
             55                  60                  65

cga cag gac aga tct gac aaa caa cca tcc aca ccc gag caa acg acc     2135
Arg Gln Asp Arg Ser Asp Lys Gln Pro Ser Thr Pro Glu Gln Thr Thr
         70                  75                  80

ccg cat gac agc ccg ccg gcc aca tcc gcc gac cag ccc ccc acc cag     2183
Pro His Asp Ser Pro Pro Ala Thr Ser Ala Asp Gln Pro Pro Thr Gln
     85                  90                  95

gcc aca gac gaa gcc gtc gac aca cag ttc agg acc gga gca agc aac     2231
Ala Thr Asp Glu Ala Val Asp Thr Gln Phe Arg Thr Gly Ala Ser Asn
100                 105                 110                 115

tct ctg ctg ttg atg ctt gac aag ctc agc aat aaa tcg tcc aat gct     2279
Ser Leu Leu Leu Met Leu Asp Lys Leu Ser Asn Lys Ser Ser Asn Ala
                120                 125                 130

aaa aag ggc cca tgg tcg agc ccc caa gag ggg aat cac caa cgt ccg     2327
Lys Lys Gly Pro Trp Ser Ser Pro Gln Glu Gly Asn His Gln Arg Pro
            135                 140                 145

act caa cag cag ggg agt caa ccc agt cgc gga aac agt cag gaa aga     2375
Thr Gln Gln Gln Gly Ser Gln Pro Ser Arg Gly Asn Ser Gln Glu Arg
        150                 155                 160

ccg cag aac caa gtc aag gcc gcc cct gga aac cag ggc aca gac gtg     2423
Pro Gln Asn Gln Val Lys Ala Ala Pro Gly Asn Gln Gly Thr Asp Val
    165                 170                 175

aac aca gca tat cat gga caa tgg gag gag tca caa cta tca gct ggt     2471
Asn Thr Ala Tyr His Gly Gln Trp Glu Glu Ser Gln Leu Ser Ala Gly
180                 185                 190                 195

gca acc cct cat gct ctc cga tca agg cag agc caa gac aat acc ctt     2519
```

-continued

```
Ala Thr Pro His Ala Leu Arg Ser Arg Gln Ser Gln Asp Asn Thr Leu
                200                 205                 210

gta tct gcg gat cat gtc cag ccg cct gta gac ttt gtg caa gcg atg     2567
Val Ser Ala Asp His Val Gln Pro Pro Val Asp Phe Val Gln Ala Met
            215                 220                 225

atg tct atg atg gag gcg ata tca cag aga gta agt aag gtt gac tat     2615
Met Ser Met Met Glu Ala Ile Ser Gln Arg Val Ser Lys Val Asp Tyr
        230                 235                 240

cag cta gat ctt gtc ttg aaa cag aca tcc tcc atc cct atg atg cgg     2663
Gln Leu Asp Leu Val Leu Lys Gln Thr Ser Ser Ile Pro Met Met Arg
    245                 250                 255

tcc gaa atc caa cag ctg aaa aca tct gtt gca gtc atg gaa gcc aac     2711
Ser Glu Ile Gln Gln Leu Lys Thr Ser Val Ala Val Met Glu Ala Asn
260                 265                 270                 275

ttg gga atg atg aag att ctg gat ccc ggt tgt gcc aac att tca tct     2759
Leu Gly Met Met Lys Ile Leu Asp Pro Gly Cys Ala Asn Ile Ser Ser
                280                 285                 290

ctg agt gat cta cgg gca gtt gcc cga tct cac ccg gtt tta gtt tca     2807
Leu Ser Asp Leu Arg Ala Val Ala Arg Ser His Pro Val Leu Val Ser
            295                 300                 305

ggc cct gga gac ccc tct ccc tat gtg aca caa gga ggc gaa atg gca     2855
Gly Pro Gly Asp Pro Ser Pro Tyr Val Thr Gln Gly Gly Glu Met Ala
        310                 315                 320

ctt aat aaa ctt tcg caa cca gtg cca cat cca tct gaa ttg att aaa     2903
Leu Asn Lys Leu Ser Gln Pro Val Pro His Pro Ser Glu Leu Ile Lys
    325                 330                 335

ccc gcc act gca tgc ggg cct gat ata gga gtg gaa aag gac act gtc     2951
Pro Ala Thr Ala Cys Gly Pro Asp Ile Gly Val Glu Lys Asp Thr Val
340                 345                 350                 355

cgt gca ttg atc atg tca cgc cca atg cac ccg agt tct tca gcc aag     2999
Arg Ala Leu Ile Met Ser Arg Pro Met His Pro Ser Ser Ser Ala Lys
                360                 365                 370

ctc cta agc aag tta gat gca gcc ggg tcg atc gag gaa atc agg aaa     3047
Leu Leu Ser Lys Leu Asp Ala Ala Gly Ser Ile Glu Glu Ile Arg Lys
            375                 380                 385

atc aag cgc ctt gct cta aat ggc   taattacta ctgccacacg tagcgggtcc   3100
Ile Lys Arg Leu Ala Leu Asn Gly
        390                 395

ctgtccactc ggcatcacac ggaatctgca ccgagttccc ccccgcagac ccaaggtcca   3160

actctccaag cggcaatcct ctctcgcttc ctcagcccca ctgaatgatc gcgtaaccgt   3220

aattaatcta gctacattta agattaagaa aaaatacggg tagaattgga gtgccccaat   3280

tgtgccaag  atg gac tca tct agg aca att ggg ctg tac ttt gat tct gcc  3331
           Met Asp Ser Ser Arg Thr Ile Gly Leu Tyr Phe Asp Ser Ala
             1               5                  10

cat tct tct agc aac ctg tta gca ttt ccg atc gtc cta caa gac aca     3379
His Ser Ser Ser Asn Leu Leu Ala Phe Pro Ile Val Leu Gln Asp Thr
 15                  20                  25                  30

gga gat ggg aag aag caa atc gcc ccg caa tat agg atc cag cgc ctt     3427
Gly Asp Gly Lys Lys Gln Ile Ala Pro Gln Tyr Arg Ile Gln Arg Leu
                35                  40                  45

gac ttg tgg act gat agt aag gag gac tca gta ttc atc acc acc tat     3475
Asp Leu Trp Thr Asp Ser Lys Glu Asp Ser Val Phe Ile Thr Thr Tyr
            50                  55                  60

gga ttc atc ttt caa gtt ggg aat gaa gaa gcc act gtc ggc atg atc     3523
Gly Phe Ile Phe Gln Val Gly Asn Glu Glu Ala Thr Val Gly Met Ile
        65                  70                  75

gat gat aaa ccc aag cgc gag tta ctt tcc gct gcg atg ctc tgc cta     3571
Asp Asp Lys Pro Lys Arg Glu Leu Leu Ser Ala Ala Met Leu Cys Leu
    80                  85                  90
```

-continued

```
gga agc gtc cca aat acc gga gac ctt att gag ctg gca agg gcc tgt      3619
Gly Ser Val Pro Asn Thr Gly Asp Leu Ile Glu Leu Ala Arg Ala Cys
 95                 100                 105                 110

ctc act atg ata gtc aca tgc aag aag agt gca act aat act gag aga      3667
Leu Thr Met Ile Val Thr Cys Lys Lys Ser Ala Thr Asn Thr Glu Arg
                115                 120                 125

atg gtt ttc tca gta gtg cag gca ccc caa gtg ctg caa agc tgt agg      3715
Met Val Phe Ser Val Val Gln Ala Pro Gln Val Leu Gln Ser Cys Arg
            130                 135                 140

gtt gtg gca aac aaa tac tca tca gtg aat gca gtc aag cac gtg aaa      3763
Val Val Ala Asn Lys Tyr Ser Ser Val Asn Ala Val Lys His Val Lys
        145                 150                 155

gcg cca gag aag att ccc ggg agt gga acc cta gaa tac aag gtg aac      3811
Ala Pro Glu Lys Ile Pro Gly Ser Gly Thr Leu Glu Tyr Lys Val Asn
    160                 165                 170

ttt gtc tcc ttg act gtg gta ccg aag aag gat gtc tac aag atc cca      3859
Phe Val Ser Leu Thr Val Val Pro Lys Lys Asp Val Tyr Lys Ile Pro
175                 180                 185                 190

gct gca gta ttg aag gtt tct ggc tcg agt ctg tac aat ctt gcg ctc      3907
Ala Ala Val Leu Lys Val Ser Gly Ser Ser Leu Tyr Asn Leu Ala Leu
                195                 200                 205

aat gtc act att aat gtg gag gta gac ccg agg agt cct ttg gtt aaa      3955
Asn Val Thr Ile Asn Val Glu Val Asp Pro Arg Ser Pro Leu Val Lys
            210                 215                 220

tct ctg tct aag tct gac agc gga tac tat gct aac ctc ttc ttg cat      4003
Ser Leu Ser Lys Ser Asp Ser Gly Tyr Tyr Ala Asn Leu Phe Leu His
        225                 230                 235

att gga ctt atg acc acc gta gat agg aag ggg aag aaa gtg aca ttt      4051
Ile Gly Leu Met Thr Thr Val Asp Arg Lys Gly Lys Lys Val Thr Phe
    240                 245                 250

gac aag ctg gaa aag aaa ata agg agc ctt gat cta tct gtc ggg ctc      4099
Asp Lys Leu Glu Lys Lys Ile Arg Ser Leu Asp Leu Ser Val Gly Leu
255                 260                 265                 270

agt gat gtg ctc ggg cct tcc gtg ttg gta aaa gca aga ggt gca cgg      4147
Ser Asp Val Leu Gly Pro Ser Val Leu Val Lys Ala Arg Gly Ala Arg
                275                 280                 285

act aag ctt ttg gca cct ttc ttc tct agc agt ggg aca gcc tgc tat      4195
Thr Lys Leu Leu Ala Pro Phe Phe Ser Ser Ser Gly Thr Ala Cys Tyr
            290                 295                 300

ccc ata gca aat gct tct cct cag gtg gcc aag ata ctc tgg agt caa      4243
Pro Ile Ala Asn Ala Ser Pro Gln Val Ala Lys Ile Leu Trp Ser Gln
        305                 310                 315

acc gcg tgc ctg cgg agc gtt aaa atc att atc caa gca ggt acc caa      4291
Thr Ala Cys Leu Arg Ser Val Lys Ile Ile Ile Gln Ala Gly Thr Gln
    320                 325                 330

cgc gct gtc gca gtg acc gcc gac cac gag gtt acc tct act aag ctg      4339
Arg Ala Val Ala Val Thr Ala Asp His Glu Val Thr Ser Thr Lys Leu
335                 340                 345                 350

gag aag ggg cac acc ctt gcc aaa tac aat cct ttt aag aaa taagctgcg    4390
Glu Lys Gly His Thr Leu Ala Lys Tyr Asn Pro Phe Lys Lys
                355                 360

tctctgagat tgcgctccgc ccactcaccc agatcatcat gacacaaaaa actaatctgt    4450

cttgattatt tacagttagt ttacctgtct atcaagttag aaaaaacacg cgtacgggta    4510

gaagagtctg gatcccgacc ggcacattca ggacgcaat  atg ggc tcc aaa ctt      4564
                                            Met Gly Ser Lys Leu
                                              1               5

tct acc agg att cca gca cct ctg atg ctg acc acc cgg att acg ctg      4612
Ser Thr Arg Ile Pro Ala Pro Leu Met Leu Thr Thr Arg Ile Thr Leu
                10                  15                  20
```

-continued

```
ata ttg agc tgt atc cgt ccg aca agc tct ctt gac ggc agg cct ctt      4660
Ile Leu Ser Cys Ile Arg Pro Thr Ser Ser Leu Asp Gly Arg Pro Leu
            25                  30                  35

gca gct gca gga att gta gta aca gga gat aag gca gtc aat gta tac      4708
Ala Ala Ala Gly Ile Val Val Thr Gly Asp Lys Ala Val Asn Val Tyr
        40                  45                  50

acc tcg tct cag aca ggg tca atc ata gtc aag ttg ctc ccg aat atg      4756
Thr Ser Ser Gln Thr Gly Ser Ile Ile Val Lys Leu Leu Pro Asn Met
    55                  60                  65

ccc agg gat aaa gag gcg tgt gca aaa gcc cca tta gag gca tat aac      4804
Pro Arg Asp Lys Glu Ala Cys Ala Lys Ala Pro Leu Glu Ala Tyr Asn
70                  75                  80                  85

aga aca ctg act act ttg cta act cct ctt ggc gac tcc atc cgc aag      4852
Arg Thr Leu Thr Thr Leu Leu Thr Pro Leu Gly Asp Ser Ile Arg Lys
                90                  95                  100

atc caa ggg tct gtg tcc acg tct gga gga ggc aga caa gca cgc ctg      4900
Ile Gln Gly Ser Val Ser Thr Ser Gly Gly Gly Arg Gln Ala Arg Leu
            105                 110                 115

ata ggt gct gtt att ggc agt gta gct ctt ggg gtt gca aca gcg gca      4948
Ile Gly Ala Val Ile Gly Ser Val Ala Leu Gly Val Ala Thr Ala Ala
        120                 125                 130

cag ata aca gca gcg gcc gcc cta ata caa gcc aac cag aat gcc gcc      4996
Gln Ile Thr Ala Ala Ala Ala Leu Ile Gln Ala Asn Gln Asn Ala Ala
    135                 140                 145

aac atc ctc cgg ctt aag gag agc att gct gca acc aat gaa gct gtg      5044
Asn Ile Leu Arg Leu Lys Glu Ser Ile Ala Ala Thr Asn Glu Ala Val
150                 155                 160                 165

cat gaa gtc acc gac gga tta tca caa cta tca gtg gca gtt ggg aag      5092
His Glu Val Thr Asp Gly Leu Ser Gln Leu Ser Val Ala Val Gly Lys
                170                 175                 180

atg cag cag ttc gtc aat gac cag ttt aat aat aca gca cga gaa ttg      5140
Met Gln Gln Phe Val Asn Asp Gln Phe Asn Asn Thr Ala Arg Glu Leu
            185                 190                 195

gac tgt ata aaa atc aca caa cag gtt ggt gta gag cta aac cta tac      5188
Asp Cys Ile Lys Ile Thr Gln Gln Val Gly Val Glu Leu Asn Leu Tyr
        200                 205                 210

cta act gaa ttg act aca gta ttc ggg cca cag atc act tcc cct gca      5236
Leu Thr Glu Leu Thr Thr Val Phe Gly Pro Gln Ile Thr Ser Pro Ala
    215                 220                 225

tta act cag ttg acc atc caa gca ctt tat aat tta gct ggt ggc aat      5284
Leu Thr Gln Leu Thr Ile Gln Ala Leu Tyr Asn Leu Ala Gly Gly Asn
230                 235                 240                 245

atg aat tac tta tta act aag tta ggt ata ggg aac aat caa ctc agc      5332
Met Asn Tyr Leu Leu Thr Lys Leu Gly Ile Gly Asn Asn Gln Leu Ser
                250                 255                 260

tca tta att ggt agc ggc ctg atc act ggt tac cct ata ctg tat gat      5380
Ser Leu Ile Gly Ser Gly Leu Ile Thr Gly Tyr Pro Ile Leu Tyr Asp
            265                 270                 275

tca cag act caa ctc ttg ggc ata caa gtg aat ttg ccc tca gtc ggg      5428
Ser Gln Thr Gln Leu Leu Gly Ile Gln Val Asn Leu Pro Ser Val Gly
        280                 285                 290

aac tta aat aat atg cgt gcc acc tat ttg gag acc tta tct gta agt      5476
Asn Leu Asn Asn Met Arg Ala Thr Tyr Leu Glu Thr Leu Ser Val Ser
    295                 300                 305

aca acc aaa gga tat gcc tca gca ctt gtc ccg aaa gta gtg aca cag      5524
Thr Thr Lys Gly Tyr Ala Ser Ala Leu Val Pro Lys Val Val Thr Gln
310                 315                 320                 325

gtc ggt tct gtg ata gaa gag ctc gac acc tca tac tgc ata gag tcc      5572
Val Gly Ser Val Ile Glu Glu Leu Asp Thr Ser Tyr Cys Ile Glu Ser
                330                 335                 340
```

```
gat ctg gat tta tat tgt act aga ata gtg aca ttc ccc atg tcc cca      5620
Asp Leu Asp Leu Tyr Cys Thr Arg Ile Val Thr Phe Pro Met Ser Pro
            345                 350                 355

ggt att tat tcc tgc ttg agc ggc aac aca tca gct tgc atg tat tca      5668
Gly Ile Tyr Ser Cys Leu Ser Gly Asn Thr Ser Ala Cys Met Tyr Ser
        360                 365                 370

aag act gaa ggc gca ctc act acg ccg tat atg gcc ctt aaa ggc tcg      5716
Lys Thr Glu Gly Ala Leu Thr Thr Pro Tyr Met Ala Leu Lys Gly Ser
    375                 380                 385

gtt att gcc aat tgt aag ata aca aca tgt aga tgt aca gac cct cct      5764
Val Ile Ala Asn Cys Lys Ile Thr Thr Cys Arg Cys Thr Asp Pro Pro
390                 395                 400                 405

ggt atc ata tcg caa aat tat gga gaa gcc gta tcc ctg ata gat aga      5812
Gly Ile Ile Ser Gln Asn Tyr Gly Glu Ala Val Ser Leu Ile Asp Arg
                410                 415                 420

cat tcg tgc aat gtc tta tca tta gac ggg ata act ctg agg ctc agt      5860
His Ser Cys Asn Val Leu Ser Leu Asp Gly Ile Thr Leu Arg Leu Ser
            425                 430                 435

ggg gaa ttt gat gca act tat caa aag aac atc tca ata cta gat tct      5908
Gly Glu Phe Asp Ala Thr Tyr Gln Lys Asn Ile Ser Ile Leu Asp Ser
        440                 445                 450

caa gtc atc gtg aca ggc aat ctt gat atc tca act gaa ctt gga aac      5956
Gln Val Ile Val Thr Gly Asn Leu Asp Ile Ser Thr Glu Leu Gly Asn
    455                 460                 465

gtc aac aat tca atc agc aat gcc ttg gat agt ttg gca gaa agc aac      6004
Val Asn Asn Ser Ile Ser Asn Ala Leu Asp Ser Leu Ala Glu Ser Asn
470                 475                 480                 485

agc aag ctg gaa aaa atc aat gtc aga cta acc agc aca tct gct ctc      6052
Ser Lys Leu Glu Lys Ile Asn Val Arg Leu Thr Ser Thr Ser Ala Leu
                490                 495                 500

att acc tat att gtt cta act gtc att tct cta gtt ttc ggt gca ttt      6100
Ile Thr Tyr Ile Val Leu Thr Val Ile Ser Leu Val Phe Gly Ala Phe
            505                 510                 515

agt ttg ggt tta gcg tgt tac ctg atg tac aaa cag aag gca caa caa      6148
Ser Leu Gly Leu Ala Cys Tyr Leu Met Tyr Lys Gln Lys Ala Gln Gln
        520                 525                 530

aag acc ttg cta tgg ctt ggg aat aat acc ctc gat cag atg aga gcc      6196
Lys Thr Leu Leu Trp Leu Gly Asn Asn Thr Leu Asp Gln Met Arg Ala
    535                 540                 545

act aca aga gca    tg aatgcagata agaggtgggt atatacccaa cagcagcctg   6250
Thr Thr Arg Ala
550

tgtatcaatt ccgataacct gtcaagtaga agacttaaga aaaaactact gggaataagc   6310

aaccaaagag cactacacgg gtagaacgat cagaggagcc acccttcaat cggaaattag   6370

gcttcacaac atccgttcta ccgcatcacc aacaacaaga gtcaatc    atg gac cgc  6426
                                                       Met Asp Arg
                                                         1

gcg gtt aac aga gtc gtg ctg gag aat gag gaa aga gaa gca aag aac      6474
Ala Val Asn Arg Val Val Leu Glu Asn Glu Glu Arg Glu Ala Lys Asn
      5                   10                  15

aca tgg cgc ctg gtt ttc cgg atc gca gtt tta ctt tta atg gta atg      6522
Thr Trp Arg Leu Val Phe Arg Ile Ala Val Leu Leu Leu Met Val Met
 20                  25                  30                  35

act cta gct atc tcc tca gct gcc ctg gca tac agc acg ggg gcc agt      6570
Thr Leu Ala Ile Ser Ser Ala Ala Leu Ala Tyr Ser Thr Gly Ala Ser
                40                  45                  50

acg ccg cac gac ctc gca agc ata ttg act gtg atc tcc aag aca gaa      6618
Thr Pro His Asp Leu Ala Ser Ile Leu Thr Val Ile Ser Lys Thr Glu
             55                  60                  65
```

```
gat aag gtt acg tct tta ctc agt tca agt caa gac gtg ata gat agg      6666
Asp Lys Val Thr Ser Leu Leu Ser Ser Ser Gln Asp Val Ile Asp Arg
         70                  75                  80

ata tac aag cag gtg gct ctt gaa tcc ccg ctg gca cta cta aac act      6714
Ile Tyr Lys Gln Val Ala Leu Glu Ser Pro Leu Ala Leu Leu Asn Thr
     85                  90                  95

gaa tct gta att atg aat gca ata acc tct ctt tct tat caa att aac      6762
Glu Ser Val Ile Met Asn Ala Ile Thr Ser Leu Ser Tyr Gln Ile Asn
100                 105                 110                 115

ggg gct gcg aac aat agc gga tgt ggg gcg cct gtt cat gac cca gat      6810
Gly Ala Ala Asn Asn Ser Gly Cys Gly Ala Pro Val His Asp Pro Asp
                120                 125                 130

tat atc ggg ggg ata ggc aaa gaa ctc ata gtg gac gac atc agt gat      6858
Tyr Ile Gly Gly Ile Gly Lys Glu Leu Ile Val Asp Asp Ile Ser Asp
            135                 140                 145

gtt aca tca ttt tat cct tct gca tat caa gaa cac ttg aat ttc atc      6906
Val Thr Ser Phe Tyr Pro Ser Ala Tyr Gln Glu His Leu Asn Phe Ile
        150                 155                 160

ccg gca cct act aca gga tcc ggt tgc act cgg ata ccc tcg ttt gac      6954
Pro Ala Pro Thr Thr Gly Ser Gly Cys Thr Arg Ile Pro Ser Phe Asp
    165                 170                 175

atg agc acc acc cat tat tgt tat act cac aat gtg ata cta tcc ggt      7002
Met Ser Thr Thr His Tyr Cys Tyr Thr His Asn Val Ile Leu Ser Gly
180                 185                 190                 195

tgc aga gat cac tca cac tca cat caa tac tta gca ctt ggt gtg ctt      7050
Cys Arg Asp His Ser His Ser His Gln Tyr Leu Ala Leu Gly Val Leu
                200                 205                 210

cgg aca tct gca aca ggg agg gta ttc ttt tct act ctg cgc tct atc      7098
Arg Thr Ser Ala Thr Gly Arg Val Phe Phe Ser Thr Leu Arg Ser Ile
            215                 220                 225

aat tta gat gac acc caa aat cgg aag tcc tgc agt gtg agt gca acc      7146
Asn Leu Asp Asp Thr Gln Asn Arg Lys Ser Cys Ser Val Ser Ala Thr
        230                 235                 240

cct tta ggt tgt gat atg ctg tgc tcc aag gtc aca ggg act gaa gag      7194
Pro Leu Gly Cys Asp Met Leu Cys Ser Lys Val Thr Gly Thr Glu Glu
    245                 250                 255

gag gat tac aag tca gtt gcc ccc aca tca atg gtg cac gga agg cta      7242
Glu Asp Tyr Lys Ser Val Ala Pro Thr Ser Met Val His Gly Arg Leu
260                 265                 270                 275

ggg ttt gac ggt caa tac cat gaa aag gac tta gac acc acg gtc tta      7290
Gly Phe Asp Gly Gln Tyr His Glu Lys Asp Leu Asp Thr Thr Val Leu
                280                 285                 290

ttt aag gat tgg gtg gca aat tac cca gga gcg gga gga ggg tct ttt      7338
Phe Lys Asp Trp Val Ala Asn Tyr Pro Gly Ala Gly Gly Gly Ser Phe
            295                 300                 305

att gac gac cgt gta tgg ttc cca gtt tac gga ggg ctc aaa ccc gat      7386
Ile Asp Asp Arg Val Trp Phe Pro Val Tyr Gly Gly Leu Lys Pro Asp
        310                 315                 320

tca ccc agt gac act gca caa gaa ggg aaa tac gta ata tac aag cgc      7434
Ser Pro Ser Asp Thr Ala Gln Glu Gly Lys Tyr Val Ile Tyr Lys Arg
    325                 330                 335

cat aac aac aca tgc ccc gat aaa caa gat tac caa att cgg aag gct      7482
His Asn Asn Thr Cys Pro Asp Lys Gln Asp Tyr Gln Ile Arg Lys Ala
340                 345                 350                 355

aag tct tca tat aaa ccc ggg cga ttt ggt ggg aag cgc gta cag caa      7530
Lys Ser Ser Tyr Lys Pro Gly Arg Phe Gly Gly Lys Arg Val Gln Gln
                360                 365                 370

gcc atc tta tcc atc aaa gtg tca aca tct ttg ggt aag gac ccg gtg      7578
Ala Ile Leu Ser Ile Lys Val Ser Thr Ser Leu Gly Lys Asp Pro Val
            375                 380                 385
```

-continued

```
ctg act att cca cct aat aca atc aca ctc atg gga gcc gaa ggc aga      7626
Leu Thr Ile Pro Pro Asn Thr Ile Thr Leu Met Gly Ala Glu Gly Arg
        390                 395                 400

att ctc aca gtg ggg aca tct cac ttc ttg tac caa cga ggg tct tca      7674
Ile Leu Thr Val Gly Thr Ser His Phe Leu Tyr Gln Arg Gly Ser Ser
    405                 410                 415

tat ttc tcc cct gcc tta tta tat ccc atg aca gta aat aac aaa acg      7722
Tyr Phe Ser Pro Ala Leu Leu Tyr Pro Met Thr Val Asn Asn Lys Thr
420                 425                 430                 435

gct aca ctc cat agt cct tat acg ttt aat gct ttc act cgg cca ggt      7770
Ala Thr Leu His Ser Pro Tyr Thr Phe Asn Ala Phe Thr Arg Pro Gly
                440                 445                 450

agt gtc cct tgc cag gca tca gca aga tgc ccc aac tca tgc att act      7818
Ser Val Pro Cys Gln Ala Ser Ala Arg Cys Pro Asn Ser Cys Ile Thr
            455                 460                 465

gga gtc tat act gat cca tat ccc tta atc ttc cat agg aat cat act      7866
Gly Val Tyr Thr Asp Pro Tyr Pro Leu Ile Phe His Arg Asn His Thr
        470                 475                 480

cta cga ggg gtc ttc gga acg atg ctt gat gat gaa caa gcg aga ctt      7914
Leu Arg Gly Val Phe Gly Thr Met Leu Asp Asp Glu Gln Ala Arg Leu
    485                 490                 495

aac ccc gta tcc gca gta ttc gac aac gta tcc cgc agt cgt gtc acc      7962
Asn Pro Val Ser Ala Val Phe Asp Asn Val Ser Arg Ser Arg Val Thr
500                 505                 510                 515

cgg gtg agt tca agc agc acc aag gca gca tac acg aca tcg aca tgt      8010
Arg Val Ser Ser Ser Ser Thr Lys Ala Ala Tyr Thr Thr Ser Thr Cys
                520                 525                 530

ttc aaa gtt gtc aag acc aat aaa act tat tgt ctt agt att gca gaa      8058
Phe Lys Val Val Lys Thr Asn Lys Thr Tyr Cys Leu Ser Ile Ala Glu
            535                 540                 545

ata tcc aat acc ctg ttc ggg gaa ttt agg atc gtt ccc tta cta gtt      8106
Ile Ser Asn Thr Leu Phe Gly Glu Phe Arg Ile Val Pro Leu Leu Val
        550                 555                 560

gag atc ctc aag gat gac ggg gtt aga gaa gcc agg tct ggc        ta    8150
Glu Ile Leu Lys Asp Asp Gly Val Arg Glu Ala Arg Ser Gly
    565                 570                 575

gttgagtcaa ttataaagga gttggaaaga tggcattgta tcacctatct tctgtgacat    8210

caagaatcaa accgaatgcc ggcgcgtgct cgaattccat gttgccagtt gaccacaatc    8270

agccagtgct catgcgatca gattaagcct tgtcaatagt ctcttgatta agaaaaaatg    8330

taagtggcaa tgagatacaa ggcaaaacag ctcatggtaa ataatacggg taggac        8386

atg gcg agc tcc ggt cct gaa agg gca gag cat cag att atc cta cca      8434
Met Ala Ser Ser Gly Pro Glu Arg Ala Glu His Gln Ile Ile Leu Pro
  1               5                  10                  15

gag tca cac ctg tct tca cca ttg gtc aag cac aaa cta ctc tat tac      8482
Glu Ser His Leu Ser Ser Pro Leu Val Lys His Lys Leu Leu Tyr Tyr
             20                  25                  30

tgg aaa tta act ggg cta ccg ctt cct gat gaa tgt gac ttc gac cac      8530
Trp Lys Leu Thr Gly Leu Pro Leu Pro Asp Glu Cys Asp Phe Asp His
         35                  40                  45

ctc att ctc agc cga caa tgg aaa aaa ata ctt gaa tcg gcc tct cct      8578
Leu Ile Leu Ser Arg Gln Trp Lys Lys Ile Leu Glu Ser Ala Ser Pro
     50                  55                  60

gat act gag aga atg ata aaa ctc gga agg gca gta cac caa act ctt      8626
Asp Thr Glu Arg Met Ile Lys Leu Gly Arg Ala Val His Gln Thr Leu
 65                  70                  75                  80

aac cac aat tcc aga ata acc gga gtg ctc cac ccc agg tgt tta gaa      8674
Asn His Asn Ser Arg Ile Thr Gly Val Leu His Pro Arg Cys Leu Glu
                 85                  90                  95
```

```
gaa ctg gct aat att gag gtc cca gat tca acc aac aaa ttt cgg aag      8722
Glu Leu Ala Asn Ile Glu Val Pro Asp Ser Thr Asn Lys Phe Arg Lys
            100                 105                 110

att gag aag aag atc caa att cac aac acg aga tat gga gaa ctg ttc      8770
Ile Glu Lys Lys Ile Gln Ile His Asn Thr Arg Tyr Gly Glu Leu Phe
        115                 120                 125

aca agg ctg tgt acg cat ata gag aag aaa ctg ctg ggg tca tct tgg      8818
Thr Arg Leu Cys Thr His Ile Glu Lys Lys Leu Leu Gly Ser Ser Trp
    130                 135                 140

tct aac aat gtc ccc cgg tca gag gag ttc agc agc att cgt acg gat      8866
Ser Asn Asn Val Pro Arg Ser Glu Glu Phe Ser Ser Ile Arg Thr Asp
145                 150                 155                 160

ccg gca ttc tgg ttt cac tca aaa tgg tcc aca gcc aag ttt gca tgg      8914
Pro Ala Phe Trp Phe His Ser Lys Trp Ser Thr Ala Lys Phe Ala Trp
                165                 170                 175

ctc cat ata aaa cag atc cag agg cat ctg atg gtg gca gct agg aca      8962
Leu His Ile Lys Gln Ile Gln Arg His Leu Met Val Ala Ala Arg Thr
            180                 185                 190

agg tct gcg gcc aac aaa ttg gtg atg cta acc cat aag gta ggc caa      9010
Arg Ser Ala Ala Asn Lys Leu Val Met Leu Thr His Lys Val Gly Gln
        195                 200                 205

gtc ttt gtc act cct gaa ctt gtc gtt gtg acg cat acg aat gag aac      9058
Val Phe Val Thr Pro Glu Leu Val Val Val Thr His Thr Asn Glu Asn
    210                 215                 220

aag ttc aca tgt ctt acc cag gaa ctt gta ttg atg tat gca gat atg      9106
Lys Phe Thr Cys Leu Thr Gln Glu Leu Val Leu Met Tyr Ala Asp Met
225                 230                 235                 240

atg gag ggc aga gat atg gtc aac ata ata tca acc acg gcg gtg cat      9154
Met Glu Gly Arg Asp Met Val Asn Ile Ile Ser Thr Thr Ala Val His
                245                 250                 255

ctc aga agc tta tca gag aaa att gat gac att ttg cgg tta ata gac      9202
Leu Arg Ser Leu Ser Glu Lys Ile Asp Asp Ile Leu Arg Leu Ile Asp
            260                 265                 270

gct ctg gca aaa gac ttg ggt aat caa gtc tac gat gtc gta tca cta      9250
Ala Leu Ala Lys Asp Leu Gly Asn Gln Val Tyr Asp Val Val Ser Leu
        275                 280                 285

atg gag gga ttt gca tac gga gct gtc cag cta ctc gag ccg tca ggt      9298
Met Glu Gly Phe Ala Tyr Gly Ala Val Gln Leu Leu Glu Pro Ser Gly
    290                 295                 300

aca ttt gca gga gat ttc ttc gca ttc aac ctg cag gag ctt aaa gac      9346
Thr Phe Ala Gly Asp Phe Phe Ala Phe Asn Leu Gln Glu Leu Lys Asp
305                 310                 315                 320

att cta att ggc ctc ctc ccc aat gat ata gca gaa tcc gtg act cat      9394
Ile Leu Ile Gly Leu Leu Pro Asn Asp Ile Ala Glu Ser Val Thr His
                325                 330                 335

gca atc gct act gta ttc tct ggt tta gaa cag aat caa gca gct gag      9442
Ala Ile Ala Thr Val Phe Ser Gly Leu Glu Gln Asn Gln Ala Ala Glu
            340                 345                 350

atg ttg tgt ctg ttg cgt ctg tgg ggt cac cca ctg ctt gag tcc cgt      9490
Met Leu Cys Leu Leu Arg Leu Trp Gly His Pro Leu Leu Glu Ser Arg
        355                 360                 365

att gca gca aag gca gtc agg agc caa atg tgc gca ccg aaa atg gta      9538
Ile Ala Ala Lys Ala Val Arg Ser Gln Met Cys Ala Pro Lys Met Val
    370                 375                 380

gac ttt gat atg atc ctt cag gta ctg tct ttc ttc aag gga aca atc      9586
Asp Phe Asp Met Ile Leu Gln Val Leu Ser Phe Phe Lys Gly Thr Ile
385                 390                 395                 400

atc aac ggg tac aga aag aag aat gca ggt gtg tgg ccg cga gtc aaa      9634
Ile Asn Gly Tyr Arg Lys Lys Asn Ala Gly Val Trp Pro Arg Val Lys
                405                 410                 415
```

-continued gtg gat aca ata tat ggg aag gtc att ggg caa cta cat gca gat tca     9682
Val Asp Thr Ile Tyr Gly Lys Val Ile Gly Gln Leu His Ala Asp Ser
            420                 425                 430 gca gag att tca cac gat atc atg tta aga gag tat aag agt tta tct     9730
Ala Glu Ile Ser His Asp Ile Met Leu Arg Glu Tyr Lys Ser Leu Ser
        435                 440                 445 gca ctt gaa ttt gag cca tgt ata gaa tat gac cct gtc acc aac ctg     9778
Ala Leu Glu Phe Glu Pro Cys Ile Glu Tyr Asp Pro Val Thr Asn Leu
    450                 455                 460 agc atg ttc cta aaa gac aag gca atc gca cac ccc aac gat aat tgg     9826
Ser Met Phe Leu Lys Asp Lys Ala Ile Ala His Pro Asn Asp Asn Trp
465                 470                 475                 480 ctt gcc tcg ttt agg cgg aac ctt ctc tcc gaa gac cag aag aaa cat     9874
Leu Ala Ser Phe Arg Arg Asn Leu Leu Ser Glu Asp Gln Lys Lys His
                485                 490                 495 gta aaa gaa gca act tcg act aat cgc ctc ttg ata gag ttt tta gag     9922
Val Lys Glu Ala Thr Ser Thr Asn Arg Leu Leu Ile Glu Phe Leu Glu
            500                 505                 510 tca aat gat ttt gat cca tat aaa gag atg gaa tat ctg acg acc ctt     9970
Ser Asn Asp Phe Asp Pro Tyr Lys Glu Met Glu Tyr Leu Thr Thr Leu
        515                 520                 525 gag tac ctt aga gat gac aat gtg gca gta tca tac tcg ctc aag gag     10018
Glu Tyr Leu Arg Asp Asp Asn Val Ala Val Ser Tyr Ser Leu Lys Glu
    530                 535                 540 aag gaa gtg aaa gtt aat gga cgg atc ttc gct aag ctg aca aag aag     10066
Lys Glu Val Lys Val Asn Gly Arg Ile Phe Ala Lys Leu Thr Lys Lys
545                 550                 555                 560 tta agg aac tgt cag gtg atg gcg gaa ggg atc cta gcc gat cag att     10114
Leu Arg Asn Cys Gln Val Met Ala Glu Gly Ile Leu Ala Asp Gln Ile
                565                 570                 575 gca cct ttc ttt cag gga aat gga gtc att cag gat agc ata tcc ttg     10162
Ala Pro Phe Phe Gln Gly Asn Gly Val Ile Gln Asp Ser Ile Ser Leu
            580                 585                 590 acc aag agt atg cta gcg atg agt caa ctg tct ttt aac agc aat aag     10210
Thr Lys Ser Met Leu Ala Met Ser Gln Leu Ser Phe Asn Ser Asn Lys
        595                 600                 605 aaa cgt atc act gac tgt aaa gaa aga gta tct tca aac cgc aat cat     10258
Lys Arg Ile Thr Asp Cys Lys Glu Arg Val Ser Ser Asn Arg Asn His
    610                 615                 620 gat ccg aaa agc aag aac cgt cgg aga gtt gca acc ttc ata aca act     10306
Asp Pro Lys Ser Lys Asn Arg Arg Arg Val Ala Thr Phe Ile Thr Thr
625                 630                 635                 640 gac ctg caa aag tac tgt ctt aat tgg aga tat cag aca atc aaa ttg     10354
Asp Leu Gln Lys Tyr Cys Leu Asn Trp Arg Tyr Gln Thr Ile Lys Leu
                645                 650                 655 ttc gct cat gcc atc aat cag ttg atg ggc cta cct cac ttc ttc gaa     10402
Phe Ala His Ala Ile Asn Gln Leu Met Gly Leu Pro His Phe Phe Glu
            660                 665                 670 tgg att cac cta aga ctg atg gac act acg atg ttc gta gga gac cct     10450
Trp Ile His Leu Arg Leu Met Asp Thr Thr Met Phe Val Gly Asp Pro
        675                 680                 685 ttc aat cct cca agt gac cct act gac tgt gac ctc tca aga gtc cct     10498
Phe Asn Pro Pro Ser Asp Pro Thr Asp Cys Asp Leu Ser Arg Val Pro
    690                 695                 700 aat gat gac ata tat att gtc agt gcc aga ggg ggt atc gaa gga tta     10546
Asn Asp Asp Ile Tyr Ile Val Ser Ala Arg Gly Gly Ile Glu Gly Leu
705                 710                 715                 720 tgc cag aag cta tgg aca atg atc tca att gct gca atc caa ctt gct     10594
Cys Gln Lys Leu Trp Thr Met Ile Ser Ile Ala Ala Ile Gln Leu Ala
                725                 730                 735

```
gca gct aga tcg cat tgt cgt gtt gcc tgt atg gta cag ggt gat aat     10642
Ala Ala Arg Ser His Cys Arg Val Ala Cys Met Val Gln Gly Asp Asn
            740                 745                 750

caa gta ata gca gta acg aga gag gta aga tca gac gac tct ccg gag     10690
Gln Val Ile Ala Val Thr Arg Glu Val Arg Ser Asp Asp Ser Pro Glu
        755                 760                 765

atg gtg ttg aca cag ttg cat caa gcc agt gat aat ttc ttc aag gaa     10738
Met Val Leu Thr Gln Leu His Gln Ala Ser Asp Asn Phe Phe Lys Glu
    770                 775                 780

tta att cat gtc aat cat ttg att ggc cat aat ttg aag gat cgt gaa     10786
Leu Ile His Val Asn His Leu Ile Gly His Asn Leu Lys Asp Arg Glu
785                 790                 795                 800

acc atc agg tca gac aca ttc ttc ata tac agc aaa cga atc ttc aaa     10834
Thr Ile Arg Ser Asp Thr Phe Phe Ile Tyr Ser Lys Arg Ile Phe Lys
            805                 810                 815

gat gga gca atc ctc agt caa gtc ctc aaa aat tca tct aaa tta gtg     10882
Asp Gly Ala Ile Leu Ser Gln Val Leu Lys Asn Ser Ser Lys Leu Val
            820                 825                 830

cta gtg tca ggt gat ctc agt gaa aac acc gta atg tcc tgt gcc aac     10930
Leu Val Ser Gly Asp Leu Ser Glu Asn Thr Val Met Ser Cys Ala Asn
        835                 840                 845

att gcc tct act gta gca cgg cta tgc gag aac ggg ctt ccc aaa gac     10978
Ile Ala Ser Thr Val Ala Arg Leu Cys Glu Asn Gly Leu Pro Lys Asp
    850                 855                 860

ttc tgt tac tat tta aac tat ata atg agt tgt gtg cag aca tac ttt     11026
Phe Cys Tyr Tyr Leu Asn Tyr Ile Met Ser Cys Val Gln Thr Tyr Phe
865                 870                 875                 880

gac tct gag ttc tcc atc acc aac aat tcg cac ccc gat ctt aat cag     11074
Asp Ser Glu Phe Ser Ile Thr Asn Asn Ser His Pro Asp Leu Asn Gln
            885                 890                 895

tcg tgg att gag gac atc tct ttt gtg cac tca tat gtt ctg act cct     11122
Ser Trp Ile Glu Asp Ile Ser Phe Val His Ser Tyr Val Leu Thr Pro
            900                 905                 910

gcc caa tta ggg gga ctg agt aac ctt caa tac tca agg ctc tac act     11170
Ala Gln Leu Gly Gly Leu Ser Asn Leu Gln Tyr Ser Arg Leu Tyr Thr
        915                 920                 925

aga aat atc ggt gac ccg ggg act act gct ttt gca gag atc aag cga     11218
Arg Asn Ile Gly Asp Pro Gly Thr Thr Ala Phe Ala Glu Ile Lys Arg
    930                 935                 940

cta gaa gca gtg gga tta ctg agt cct aac att atg act aat atc tta     11266
Leu Glu Ala Val Gly Leu Leu Ser Pro Asn Ile Met Thr Asn Ile Leu
945                 950                 955                 960

act agg ccg cct ggg aat gga gat tgg gcc agt ctg tgc aac gac cca     11314
Thr Arg Pro Pro Gly Asn Gly Asp Trp Ala Ser Leu Cys Asn Asp Pro
                965                 970                 975

tac tct ttc aat ttt gag act gtt gca agc cca aat att gtt ctt aag     11362
Tyr Ser Phe Asn Phe Glu Thr Val Ala Ser Pro Asn Ile Val Leu Lys
            980                 985                 990

aaa cat acg caa aga gtc cta ttt gaa act tgt tca aat ccc tta ttg     11410
Lys His Thr Gln Arg Val Leu Phe Glu Thr Cys Ser Asn Pro Leu Leu
        995                1000                1005

tct gga gtg cac aca gag gat aat gag gca gaa gag aag gca ttg gct     11458
Ser Gly Val His Thr Glu Asp Asn Glu Ala Glu Glu Lys Ala Leu Ala
   1010                1015                1020

gaa ttc ttg ctt aat caa gag gtg att cat ccc cgc gtt gcg cat gcc     11506
Glu Phe Leu Leu Asn Gln Glu Val Ile His Pro Arg Val Ala His Ala
1025               1030                1035                1040

atc atg gag gca agc tct gta ggt agg aga aag caa att caa ggg ctt     11554
Ile Met Glu Ala Ser Ser Val Gly Arg Arg Lys Gln Ile Gln Gly Leu
               1045                1050                1055
```

```
gtt gac aca aca aac acc gta att aag att gcg ctt act agg agg cca    11602
Val Asp Thr Thr Asn Thr Val Ile Lys Ile Ala Leu Thr Arg Arg Pro
            1060                1065                1070

tta ggc atc aag agg ctg atg cgg ata gtc aat tat tct agc atg cat    11650
Leu Gly Ile Lys Arg Leu Met Arg Ile Val Asn Tyr Ser Ser Met His
        1075                1080                1085

gca atg ctg ttt aga gac gat gtt ttt tcc tcc agt aga tcc aac cac    11698
Ala Met Leu Phe Arg Asp Asp Val Phe Ser Ser Ser Arg Ser Asn His
    1090                1095                1100

ccc tta gtc tct tct aat atg tgt tct ctg aca ctg gca gac tat gca    11746
Pro Leu Val Ser Ser Asn Met Cys Ser Leu Thr Leu Ala Asp Tyr Ala
1105                1110                1115                1120

cgg aat aga agc tgg tca cct ttg acg gga ggc agg aaa ata ctg ggt    11794
Arg Asn Arg Ser Trp Ser Pro Leu Thr Gly Gly Arg Lys Ile Leu Gly
                1125                1130                1135

gta tct aat cct gat acg ata gaa ctc gta gag ggt gag att ctt agt    11842
Val Ser Asn Pro Asp Thr Ile Glu Leu Val Glu Gly Glu Ile Leu Ser
            1140                1145                1150

gta agc gga ggg tgt aca aga tgt gac agc gga gat gaa caa ttt act    11890
Val Ser Gly Gly Cys Thr Arg Cys Asp Ser Gly Asp Glu Gln Phe Thr
        1155                1160                1165

tgg ttc cat ctt cca agc aat ata gaa ttg acc gat gac acc agc aag    11938
Trp Phe His Leu Pro Ser Asn Ile Glu Leu Thr Asp Asp Thr Ser Lys
    1170                1175                1180

aat cct ccg atg agg gta cca tat ctc ggg tca aag aca cag gag agg    11986
Asn Pro Pro Met Arg Val Pro Tyr Leu Gly Ser Lys Thr Gln Glu Arg
1185                1190                1195                1200

aga gct gcc tca ctt gca aaa ata gct cat atg tcg cca cat gta aag    12034
Arg Ala Ala Ser Leu Ala Lys Ile Ala His Met Ser Pro His Val Lys
                1205                1210                1215

gct gcc cta agg gca tca tcc gtg ttg atc tgg gct tat ggg gat aat    12082
Ala Ala Leu Arg Ala Ser Ser Val Leu Ile Trp Ala Tyr Gly Asp Asn
            1220                1225                1230

gaa gta aat tgg act gct gct ctt acg att gca aaa tct cgg tgt aat    12130
Glu Val Asn Trp Thr Ala Ala Leu Thr Ile Ala Lys Ser Arg Cys Asn
        1235                1240                1245

gta aac tta gag tat ctt cgg tta ctg tcc cct tta ccc acg gct ggg    12178
Val Asn Leu Glu Tyr Leu Arg Leu Leu Ser Pro Leu Pro Thr Ala Gly
    1250                1255                1260

aat ctt caa cat aga cta gat gat ggt ata act cag atg aca ttc acc    12226
Asn Leu Gln His Arg Leu Asp Asp Gly Ile Thr Gln Met Thr Phe Thr
1265                1270                1275                1280

cct gca tct ctc tac agg gtg tca cct tac att cac ata tcc aat gat    12274
Pro Ala Ser Leu Tyr Arg Val Ser Pro Tyr Ile His Ile Ser Asn Asp
                1285                1290                1295

tct caa agg ctg ttc act gaa gaa gga gtc aaa gag ggg aat gtg gtt    12322
Ser Gln Arg Leu Phe Thr Glu Glu Gly Val Lys Glu Gly Asn Val Val
            1300                1305                1310

tac caa cag atc atg ctc ttg ggt tta tct cta atc gaa tcg ata ttt    12370
Tyr Gln Gln Ile Met Leu Leu Gly Leu Ser Leu Ile Glu Ser Ile Phe
        1315                1320                1325

cca atg aca aca acc agg aca tat gat gag atc aca ctg cac cta cat    12418
Pro Met Thr Thr Thr Arg Thr Tyr Asp Glu Ile Thr Leu His Leu His
    1330                1335                1340

agt aaa ttt agt tgc tgt atc aga gaa gca cct gtt gcg gtt cct ttc    12466
Ser Lys Phe Ser Cys Cys Ile Arg Glu Ala Pro Val Ala Val Pro Phe
1345                1350                1355                1360

gag cta ctt ggg gtg gta ccg gaa ctg agg aca gtg acc tca aat aag    12514
Glu Leu Leu Gly Val Val Pro Glu Leu Arg Thr Val Thr Ser Asn Lys
                1365                1370                1375
```

-continued

```
ttt atg tat gat cct agc cct gta tcg gag gga gac ttt gcg aga ctt    12562
Phe Met Tyr Asp Pro Ser Pro Val Ser Glu Gly Asp Phe Ala Arg Leu
            1380                1385                1390

gac tta gct atc ttc aag agt tat gag ctt aat ctg gag tca tat ccc    12610
Asp Leu Ala Ile Phe Lys Ser Tyr Glu Leu Asn Leu Glu Ser Tyr Pro
        1395                1400                1405

acg ata gag cta atg aac att ctt tca ata tcc agc ggg aag ttg att    12658
Thr Ile Glu Leu Met Asn Ile Leu Ser Ile Ser Ser Gly Lys Leu Ile
    1410                1415                1420

ggc cag tct gtg gtt tct tat gat gaa gat acc tcc ata aag aat gac    12706
Gly Gln Ser Val Val Ser Tyr Asp Glu Asp Thr Ser Ile Lys Asn Asp
1425                1430                1435                1440

gcc ata ata gtg tat gac aat acc cga aat tgg atc agt gaa gct cag    12754
Ala Ile Ile Val Tyr Asp Asn Thr Arg Asn Trp Ile Ser Glu Ala Gln
                1445                1450                1455

aat tca gat gtg gtc cgc cta ttt gaa tat gca gca ctt gaa gtg ctc    12802
Asn Ser Asp Val Val Arg Leu Phe Glu Tyr Ala Ala Leu Glu Val Leu
            1460                1465                1470

ctc gac tgt tct tac caa ctc tat tac ctg aga gta aga ggc cta gac    12850
Leu Asp Cys Ser Tyr Gln Leu Tyr Tyr Leu Arg Val Arg Gly Leu Asp
        1475                1480                1485

aat att gtc tta tat atg ggt gat tta tac aag aat atg cca gga att    12898
Asn Ile Val Leu Tyr Met Gly Asp Leu Tyr Lys Asn Met Pro Gly Ile
    1490                1495                1500

cta ctt tcc aac att gca gct aca ata tct cat ccc gtc att cat tca    12946
Leu Leu Ser Asn Ile Ala Ala Thr Ile Ser His Pro Val Ile His Ser
1505                1510                1515                1520

agg tta cat gca gtg ggc ctg gtc aac cat gac gga tca cac caa ctt    12994
Arg Leu His Ala Val Gly Leu Val Asn His Asp Gly Ser His Gln Leu
                1525                1530                1535

gca gat acg gat ttt atc gaa atg tct gca aaa cta tta gta tct tgc    13042
Ala Asp Thr Asp Phe Ile Glu Met Ser Ala Lys Leu Leu Val Ser Cys
            1540                1545                1550

acc cga cgt gtg atc tcc ggc tta tat tca gga aat aag tat gat ctg    13090
Thr Arg Arg Val Ile Ser Gly Leu Tyr Ser Gly Asn Lys Tyr Asp Leu
        1555                1560                1565

ctg ttc cca tct gtc tta gat gat aac ctg aat gag aag atg ctt cag    13138
Leu Phe Pro Ser Val Leu Asp Asp Asn Leu Asn Glu Lys Met Leu Gln
    1570                1575                1580

ctg ata tcc cgg tta tgc tgt ctg tac acg gta ctc ttt gct aca aca    13186
Leu Ile Ser Arg Leu Cys Cys Leu Tyr Thr Val Leu Phe Ala Thr Thr
1585                1590                1595                1600

aga gaa atc ccg aaa ata aga ggc tta act gca gaa gag aaa tgt tca    13234
Arg Glu Ile Pro Lys Ile Arg Gly Leu Thr Ala Glu Glu Lys Cys Ser
                1605                1610                1615

ata ctc act gag tat tta ctg tcg gat gct gtg aaa cca tta ctt agc    13282
Ile Leu Thr Glu Tyr Leu Leu Ser Asp Ala Val Lys Pro Leu Leu Ser
            1620                1625                1630

ccc gat caa gtg agc tct atc atg tct cct aac ata att aca ttc cca    13330
Pro Asp Gln Val Ser Ser Ile Met Ser Pro Asn Ile Ile Thr Phe Pro
        1635                1640                1645

gct aat ctg tac tac atg tct cgg aag agc ctc aat ttg atc agg gaa    13378
Ala Asn Leu Tyr Tyr Met Ser Arg Lys Ser Leu Asn Leu Ile Arg Glu
    1650                1655                1660

agg gag gac agg gat act atc ctg gcg ttg ttg ttc ccc caa gag cca    13426
Arg Glu Asp Arg Asp Thr Ile Leu Ala Leu Leu Phe Pro Gln Glu Pro
1665                1670                1675                1680

tta tta gag ttc cct tct gtg caa gat att ggt gct cga gtg aaa gat    13474
Leu Leu Glu Phe Pro Ser Val Gln Asp Ile Gly Ala Arg Val Lys Asp
                1685                1690                1695
```

-continued

```
cca ttc acc cga caa cct gcg gca ttt ttg caa gag tta gat ttg agt    13522
Pro Phe Thr Arg Gln Pro Ala Ala Phe Leu Gln Glu Leu Asp Leu Ser
            1700                1705                1710

gct cca gca agg tat gac gca ttc aca ctt agt cag att cat cct gaa    13570
Ala Pro Ala Arg Tyr Asp Ala Phe Thr Leu Ser Gln Ile His Pro Glu
        1715                1720                1725

ctc aca tct cca aat ccg gag gaa gac tac tta gta cga tac ttg ttc    13618
Leu Thr Ser Pro Asn Pro Glu Glu Asp Tyr Leu Val Arg Tyr Leu Phe
    1730                1735                1740

aga ggg ata ggg act gca tct tcc tct tgg tat aag gca tcc cat ctc    13666
Arg Gly Ile Gly Thr Ala Ser Ser Ser Trp Tyr Lys Ala Ser His Leu
1745                1750                1755                1760

ctt tct gta ccc gag gta aga tgt gca aga cac ggg aac tcc tta tac    13714
Leu Ser Val Pro Glu Val Arg Cys Ala Arg His Gly Asn Ser Leu Tyr
                1765                1770                1775

tta gct gaa ggg agc gga gcc atc atg agt ctt ctc gaa ctg cat gta    13762
Leu Ala Glu Gly Ser Gly Ala Ile Met Ser Leu Leu Glu Leu His Val
            1780                1785                1790

cca cat gaa act atc tat tac aat acg ctc ttt tca aat gag atg aac    13810
Pro His Glu Thr Ile Tyr Tyr Asn Thr Leu Phe Ser Asn Glu Met Asn
        1795                1800                1805

ccc ccg caa cga cat ttc ggg ccg acc cca act cag ttt ttg aat tcg    13858
Pro Pro Gln Arg His Phe Gly Pro Thr Pro Thr Gln Phe Leu Asn Ser
    1810                1815                1820

gtt gtt tat agg aat cta cag gcg gag gta aca tgc aaa gat gga ttt    13906
Val Val Tyr Arg Asn Leu Gln Ala Glu Val Thr Cys Lys Asp Gly Phe
1825                1830                1835                1840

gtc caa gag ttc cgt cca tta tgg aga gaa aat aca gag gaa agt gac    13954
Val Gln Glu Phe Arg Pro Leu Trp Arg Glu Asn Thr Glu Glu Ser Asp
                1845                1850                1855

ctg acc tca gat aaa gca gtg ggg tat att aca tct gca gtg ccc tac    14002
Leu Thr Ser Asp Lys Ala Val Gly Tyr Ile Thr Ser Ala Val Pro Tyr
            1860                1865                1870

aga tct gta tca ttg ctg cat tgt gac att gaa att cct cca ggg tcc    14050
Arg Ser Val Ser Leu Leu His Cys Asp Ile Glu Ile Pro Pro Gly Ser
        1875                1880                1885

aat caa agc tta cta gat caa cta gct atc aat tta tct ctg att gcc    14098
Asn Gln Ser Leu Leu Asp Gln Leu Ala Ile Asn Leu Ser Leu Ile Ala
    1890                1895                1900

atg cat tct gta agg gag ggc ggg gta gta atc atc aaa gtg ttg tat    14146
Met His Ser Val Arg Glu Gly Gly Val Val Ile Ile Lys Val Leu Tyr
1905                1910                1915                1920

gca atg gga tac tac ttt cat cta ctc atg aac ttg ttt gct ccg tgt    14194
Ala Met Gly Tyr Tyr Phe His Leu Leu Met Asn Leu Phe Ala Pro Cys
                1925                1930                1935

tcc aca aaa gga tat att ctc tct aat ggt tat gca tgt cga gga gat    14242
Ser Thr Lys Gly Tyr Ile Leu Ser Asn Gly Tyr Ala Cys Arg Gly Asp
            1940                1945                1950

atg gag tgt tac ctg gta ttt gtc atg ggt tac ctg ggc ggg cct aca    14290
Met Glu Cys Tyr Leu Val Phe Val Met Gly Tyr Leu Gly Gly Pro Thr
        1955                1960                1965

ttt gta cat gag gtg gtg agg atg gca aaa act ctg gtg cag cgg cac    14338
Phe Val His Glu Val Val Arg Met Ala Lys Thr Leu Val Gln Arg His
    1970                1975                1980

ggt acg ctt ttg tct aaa tca gat gag atc aca ctg acc agg tta ttc    14386
Gly Thr Leu Leu Ser Lys Ser Asp Glu Ile Thr Leu Thr Arg Leu Phe
1985                1990                1995                2000

acc tca cag cgg cag cgt gtg aca gac atc cta tcc agt cct tta cca    14434
Thr Ser Gln Arg Gln Arg Val Thr Asp Ile Leu Ser Ser Pro Leu Pro
                2005                2010                2015
```

```
aga tta ata aag tac ttg agg aag aat att gac act gcg ctg att gaa    14482
Arg Leu Ile Lys Tyr Leu Arg Lys Asn Ile Asp Thr Ala Leu Ile Glu
            2020                2025                2030

gcc ggg gga cag ccc gtc cgt cca ttc tgt gcg gag agt ctg gtg agc    14530
Ala Gly Gly Gln Pro Val Arg Pro Phe Cys Ala Glu Ser Leu Val Ser
        2035                2040                2045

acg cta gcg aac ata act cag ata acc cag atc atc gct agt cac att    14578
Thr Leu Ala Asn Ile Thr Gln Ile Thr Gln Ile Ile Ala Ser His Ile
    2050                2055                2060

gac aca gtt atc cgg tct gtg ata tat atg gaa gct gag ggt gat ctc    14626
Asp Thr Val Ile Arg Ser Val Ile Tyr Met Glu Ala Glu Gly Asp Leu
2065                2070                2075                2080

gct gac aca gta ttt cta ttt acc cct tac aat ctc tct act gac ggg    14674
Ala Asp Thr Val Phe Leu Phe Thr Pro Tyr Asn Leu Ser Thr Asp Gly
                2085                2090                2095

aaa aag agg aca tca ctt aaa cag tgc acg aga cag atc cta gag gtt    14722
Lys Lys Arg Thr Ser Leu Lys Gln Cys Thr Arg Gln Ile Leu Glu Val
            2100                2105                2110

aca ata cta ggt ctt aga gtc gaa aat ctc aat aaa ata ggc gat ata    14770
Thr Ile Leu Gly Leu Arg Val Glu Asn Leu Asn Lys Ile Gly Asp Ile
        2115                2120                2125

atc agc cta gtg ctt aaa ggc atg atc tcc atg gag gac ctt atc cca    14818
Ile Ser Leu Val Leu Lys Gly Met Ile Ser Met Glu Asp Leu Ile Pro
    2130                2135                2140

cta agg aca tac ttg aag cat agt acc tgc cct aaa tat ttg aag gct    14866
Leu Arg Thr Tyr Leu Lys His Ser Thr Cys Pro Lys Tyr Leu Lys Ala
2145                2150                2155                2160

gtc cta ggt att acc aaa ctc aaa gaa atg ttt aca gac act tct gta    14914
Val Leu Gly Ile Thr Lys Leu Lys Glu Met Phe Thr Asp Thr Ser Val
                2165                2170                2175

ctg tac ttg act cgt gct caa caa aaa ttc tac atg aaa act ata ggc    14962
Leu Tyr Leu Thr Arg Ala Gln Gln Lys Phe Tyr Met Lys Thr Ile Gly
            2180                2185                2190

aat gca gtc aaa gga tat tac agt aac tgt gac tct     ta acgaaaatca  15010
Asn Ala Val Lys Gly Tyr Tyr Ser Asn Cys Asp Ser
        2195                2200

catattaata ggctcctttt ttggccaatt gtattcttgt tgatttaatc atattatgtt  15070

agaaaaaagt tgaaccctga ctccttagga ctcgaattcg aactcaaata aatgtcttaa  15130

aaaaaggttg cgcacaatta ttcttgagtg tagtctcgtc attcaccaaa tctttgtttg  15190

gtgggtcggc atggcatctc cacctcctcg cggtccgacc tgggcatccg aaggaggacg  15250

tcgtccactc ggatggctaa gggagagctc ggatccggct gctaacaaag cccgaaagga  15310

agctgagttg gctgctgcca ccgctgagca ataactagca taaccccttg gggcctctaa  15370

acgggtcttg aggggttttt tgcatatgcg gtgtgaaata ccgcacagat gcgtaaggag  15430

aaaataccgc atcaggcgct cttccgcttc ctcgctcact gactcgctgc gctcggtcgt  15490

tcggctgcgg cgagcggtat cagctcactc aaaggcggta atacggttat ccacagaatc  15550

aggggataac gcaggaaaga acatgtgagc aaaaggccag caaaaggcca ggaaccgtaa  15610

aaaggccgcg ttgctggcgt ttttccatag gctccgcccc cctgacgagc atcacaaaaa  15670

tcgacgctca agtcagaggt ggcgaaaccc gacaggacta taaagatacc aggcgtttcc  15730

ccctggaagc tccctcgtgc gctctcctgt tccgaccctg ccgcttaccg gatacctgtc  15790

cgcctttctc ccttcgggaa gcgtggcgct ttctcatagc tcacgctgta ggtatctcag  15850

ttcggtgtag gtcgttcgct ccaagctggg ctgtgtgcac gaacccccccg ttcagcccga  15910

ccgctgcgcc ttatccggta actatcgtct tgagtccaac ccggtaagac acgacttatc  15970
```

-continued

```
gccactggca gcagccactg gtaacaggat tagcagagcg aggtatgtag gcggtgctac  16030

agagttcttg aagtggtggc ctaactacgg ctacactaga aggacagtat ttggtatctg  16090

cgctctgctg aagccagtta ccttcggaaa aagagttggt agctcttgat ccggcaaaca  16150

aaccaccgct ggtagcggtg gtttttttgt ttgcaagcag cagattacgc gcagaaaaaa  16210

aggatctcaa gaagatcctt tgatcttttc tacggggtct gacgctcagt ggaacgaaaa  16270

ctcacgttaa gggattttgg tcatgagatt atcaaaaagg atcttcacct agatcctttt  16330

aaattaaaaa tgaagtttta aatcaatcta aagtatatat gagtaaactt ggtctgacag  16390

ttaccaatgc ttaatcagtg aggcacctat ctcagcgatc tgtctatttc gttcatccat  16450

agttgcctga ctccccgtcg tgtagataac tacgatacgg gagggcttac catctggccc  16510

cagtgctgca atgataccgc gagacccacg ctcaccggct ccagatttat cagcaataaa  16570

ccagccagcc ggaagggccg agcgcagaag tggtcctgca actttatccg cctccatcca  16630

gtctattaat tgttgccggg aagctagagt aagtagttcg ccagttaata gtttgcgcaa  16690

cgttgttgcc attgctgcag gcatcgtggt gtcacgctcg tcgtttggta tggcttcatt  16750

cagctccggt tcccaacgat caaggcgagt tacatgatcc cccatgttgt gcaaaaaagc  16810

ggttagctcc ttcggtcctc cgatcgttgt cagaagtaag ttggccgcag tgttatcact  16870

catggttatg gcagcactgc ataattctct tactgtcatg ccatccgtaa gatgcttttc  16930

tgtgactggt gagtactcaa ccaagtcatt ctgagaatag tgtatgcggc gaccgagttg  16990

ctcttgcccg gcgtcaacac gggataatac cgcgccacat agcagaactt taaaagtgct  17050

catcattgga aaacgttctt cggggcgaaa actctcaagg atcttaccgc tgttgagatc  17110

cagttcgatg taacccactc gtgcacccaa ctgatcttca gcatctttta ctttcaccag  17170

cgtttctggg tgagcaaaaa caggaaggca aaatgccgca aaaaagggaa taagggcgac  17230

acggaaatgt tgaatactca tactcttcct ttttcaatat tattgaagca tttatcaggg  17290

ttattgtctc atgagcggat acatatttga atgtatttag aaaaataaac aaataggggt  17350

tccgcgcaca tttccccgaa aagtgccacc tgacgtctaa gaaaccatta ttatcatgac  17410

attaacctat aaaaataggc gtatcacgag gccctttcgt cttcaagaat tctaatacga  17470

ctcactatag g                                                       17481
```

<210> SEQ ID NO 2
<211> LENGTH: 489
<212> TYPE: PRT
<213> ORGANISM: Artificial Sequence
<220> FEATURE:
<223> OTHER INFORMATION: NP protein

<400> SEQUENCE: 2

```
Met Ser Ser Val Phe Asp Glu Tyr Glu Gln Leu Leu Ala Ala Gln Thr
  1               5                  10                  15

Arg Pro Asn Gly Ala His Gly Gly Gly Glu Lys Gly Ser Thr Leu Lys
             20                  25                  30

Val Asp Val Pro Val Phe Thr Leu Asn Ser Asp Asp Pro Glu Asp Arg
         35                  40                  45

Trp Ser Phe Val Val Phe Cys Leu Arg Ile Ala Val Ser Glu Asp Ala
     50                  55                  60

Asn Lys Pro Leu Arg Gln Gly Ala Leu Ile Ser Leu Leu Cys Ser His
 65                  70                  75                  80

Ser Gln Val Met Arg Asn His Val Ala Ile Ala Gly Lys Gln Asn Glu
                 85                  90                  95
```

-continued

```
Ala Thr Leu Ala Val Leu Glu Ile Asp Gly Phe Ala Asn Gly Thr Pro
            100                 105                 110

Gln Phe Asn Asn Arg Ser Gly Val Ser Glu Glu Arg Ala Gln Arg Phe
        115                 120                 125

Ala Met Ile Ala Gly Ser Leu Pro Arg Ala Cys Ser Asn Gly Thr Pro
    130                 135                 140

Phe Val Thr Ala Gly Ala Glu Asp Asp Ala Pro Glu Asp Ile Thr Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
            180                 185                 190

Arg Ile Asn Lys Tyr Met Gln Gln Gly Arg Val Gln Lys Lys Tyr Ile
        195                 200                 205

Leu Tyr Pro Val Cys Arg Ser Thr Ile Gln Leu Thr Ile Arg Gln Ser
    210                 215                 220

Leu Ala Val Arg Ile Phe Leu Val Ser Glu Leu Lys Arg Gly Arg Asn
225                 230                 235                 240

Thr Ala Gly Gly Thr Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
            260                 265                 270

Tyr Gly Ile Asn Thr Lys Thr Ser Ala Leu Ala Leu Ser Ser Leu Ser
        275                 280                 285

Gly Asp Ile Gln Lys Met Lys Gln Leu Met Arg Leu Tyr Arg Met Lys
    290                 295                 300

Gly Asp Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Gly
                325                 330                 335

Met Ala Ser Val Leu Asp Lys Gly Thr Gly Lys Tyr Gln Phe Ala Arg
            340                 345                 350

Asp Phe Met Ser Thr Ser Phe Trp Arg Leu Gly Val Glu Tyr Ala Gln
        355                 360                 365

Ala Gln Gly Ser Ser Ile Asn Glu Asp Met Ala Ala Glu Leu Lys Leu
    370                 375                 380

Thr Pro Ala Ala Met Lys Gly Leu Ala Ala Ala Ala Gln Arg Val Ser
385                 390                 395                 400

Asp Asp Thr Ser Ser Ile Tyr Met Pro Thr Gln Gln Val Gly Val Leu
                405                 410                 415

Thr Gly Leu Ser Glu Gly Gly Ser Gln Ala Leu Gln Gly Gly Ser Asn
            420                 425                 430

Arg Ser Gln Gly Gln Pro Glu Ala Gly Asp Gly Glu Thr Gln Phe Leu
        435                 440                 445

Asp Leu Met Arg Ala Val Ala Asn Ser Met Arg Glu Ala Pro Asn Ser
    450                 455                 460

Ala Gln Gly Thr Pro Gln Ser Gly Pro Pro Pro Thr Pro Gly Pro Ser
465                 470                 475                 480

Gln Asp Asn Asp Thr Asp Trp Gly Tyr
                485
```

<210> SEQ ID NO 3
<211> LENGTH: 395
<212> TYPE: PRT

<213> ORGANISM: Artificial Sequence
<220> FEATURE:
<223> OTHER INFORMATION: P protein

<400> SEQUENCE: 3

```
Met Ala Thr Phe Thr Asp Ala Glu Ile Asp Glu Leu Phe Glu Thr Ser
  1               5                  10                  15

Gly Thr Val Ile Asp Asn Ile Ile Thr Ala Gln Gly Lys Pro Ala Glu
             20                  25                  30

Thr Val Gly Arg Ser Ala Ile Pro Gln Gly Lys Thr Lys Val Leu Ser
         35                  40                  45

Ala Ala Trp Glu Lys His Gly Ser Ile Gln Pro Pro Ala Ser Gln Asp
     50                  55                  60

Asn Pro Asp Arg Gln Asp Arg Ser Asp Lys Gln Pro Ser Thr Pro Glu
 65                  70                  75                  80

Gln Thr Thr Pro His Asp Ser Pro Pro Ala Thr Ser Ala Asp Gln Pro
                 85                  90                  95

Pro Thr Gln Ala Thr Asp Glu Ala Val Asp Thr Gln Phe Arg Thr Gly
            100                 105                 110

Ala Ser Asn Ser Leu Leu Leu Met Leu Asp Lys Leu Ser Asn Lys Ser
        115                 120                 125

Ser Asn Ala Lys Lys Gly Pro Trp Ser Ser Pro Gln Glu Gly Asn His
    130                 135                 140

Gln Arg Pro Thr Gln Gln Gly Ser Gln Pro Ser Arg Gly Asn Ser
145                 150                 155                 160

Gln Glu Arg Pro Gln Asn Gln Val Lys Ala Ala Pro Gly Asn Gln Gly
                165                 170                 175

Thr Asp Val Asn Thr Ala Tyr His Gly Gln Trp Glu Glu Ser Gln Leu
            180                 185                 190

Ser Ala Gly Ala Thr Pro His Ala Leu Arg Ser Arg Gln Ser Gln Asp
        195                 200                 205

Asn Thr Leu Val Ser Ala Asp His Val Gln Pro Pro Val Asp Phe Val
    210                 215                 220

Gln Ala Met Met Ser Met Met Glu Ala Ile Ser Gln Arg Val Ser Lys
225                 230                 235                 240

Val Asp Tyr Gln Leu Asp Leu Val Leu Lys Gln Thr Ser Ser Ile Pro
                245                 250                 255

Met Met Arg Ser Glu Ile Gln Gln Leu Lys Thr Ser Val Ala Val Met
            260                 265                 270

Glu Ala Asn Leu Gly Met Met Lys Ile Leu Asp Pro Gly Cys Ala Asn
        275                 280                 285

Ile Ser Ser Leu Ser Asp Leu Arg Ala Val Ala Arg Ser His Pro Val
    290                 295                 300

Leu Val Ser Gly Pro Gly Asp Pro Ser Pro Tyr Val Thr Gln Gly Gly
305                 310                 315                 320

Glu Met Ala Leu Asn Lys Leu Ser Gln Pro Val Pro His Pro Ser Glu
                325                 330                 335

Leu Ile Lys Pro Ala Thr Ala Cys Gly Pro Asp Ile Gly Val Glu Lys
            340                 345                 350

Asp Thr Val Arg Ala Leu Ile Met Ser Arg Pro Met His Pro Ser Ser
        355                 360                 365

Ser Ala Lys Leu Leu Ser Lys Leu Asp Ala Ala Gly Ser Ile Glu Glu
    370                 375                 380

Ile Arg Lys Ile Lys Arg Leu Ala Leu Asn Gly
385                 390                 395
```

<210> SEQ ID NO 4
<211> LENGTH: 364
<212> TYPE: PRT
<213> ORGANISM: Artificial Sequence
<220> FEATURE:
<223> OTHER INFORMATION: M protein

<400> SEQUENCE: 4

```
Met Asp Ser Ser Arg Thr Ile Gly Leu Tyr Phe Asp Ser Ala His Ser
  1               5                  10                  15

Ser Ser Asn Leu Leu Ala Phe Pro Ile Val Leu Gln Asp Thr Gly Asp
             20                  25                  30

Gly Lys Lys Gln Ile Ala Pro Gln Tyr Arg Ile Gln Arg Leu Asp Leu
         35                  40                  45

Trp Thr Asp Ser Lys Glu Asp Ser Val Phe Ile Thr Thr Tyr Gly Phe
     50                  55                  60

Ile Phe Gln Val Gly Asn Glu Glu Ala Thr Val Gly Met Ile Asp Asp
 65                  70                  75                  80

Lys Pro Lys Arg Glu Leu Leu Ser Ala Ala Met Leu Cys Leu Gly Ser
                 85                  90                  95

Val Pro Asn Thr Gly Asp Leu Ile Glu Leu Ala Arg Ala Cys Leu Thr
            100                 105                 110

Met Ile Val Thr Cys Lys Lys Ser Ala Thr Asn Thr Glu Arg Met Val
        115                 120                 125

Phe Ser Val Val Gln Ala Pro Gln Val Leu Gln Ser Cys Arg Val Val
    130                 135                 140

Ala Asn Lys Tyr Ser Ser Val Asn Ala Val Lys His Val Lys Ala Pro
145                 150                 155                 160

Glu Lys Ile Pro Gly Ser Gly Thr Leu Glu Tyr Lys Val Asn Phe Val
                165                 170                 175

Ser Leu Thr Val Val Pro Lys Lys Asp Val Tyr Lys Ile Pro Ala Ala
            180                 185                 190

Val Leu Lys Val Ser Gly Ser Ser Leu Tyr Asn Leu Ala Leu Asn Val
        195                 200                 205

Thr Ile Asn Val Glu Val Asp Pro Arg Ser Pro Leu Val Lys Ser Leu
    210                 215                 220

Ser Lys Ser Asp Ser Gly Tyr Tyr Ala Asn Leu Phe Leu His Ile Gly
225                 230                 235                 240

Leu Met Thr Thr Val Asp Arg Lys Gly Lys Lys Val Thr Phe Asp Lys
                245                 250                 255

Leu Glu Lys Lys Ile Arg Ser Leu Asp Leu Ser Val Gly Leu Ser Asp
            260                 265                 270

Val Leu Gly Pro Ser Val Leu Val Lys Ala Arg Gly Ala Arg Thr Lys
        275                 280                 285

Leu Leu Ala Pro Phe Phe Ser Ser Ser Gly Thr Ala Cys Tyr Pro Ile
    290                 295                 300

Ala Asn Ala Ser Pro Gln Val Ala Lys Ile Leu Trp Ser Gln Thr Ala
305                 310                 315                 320

Cys Leu Arg Ser Val Lys Ile Ile Ile Gln Ala Gly Thr Gln Arg Ala
                325                 330                 335

Val Ala Val Thr Ala Asp His Glu Val Thr Ser Thr Lys Leu Glu Lys
            340                 345                 350

Gly His Thr Leu Ala Lys Tyr Asn Pro Phe Lys Lys
        355                 360
```

<210> SEQ ID NO 5
<211> LENGTH: 553
<212> TYPE: PRT
<213> ORGANISM: Artificial Sequence
<220> FEATURE:
<223> OTHER INFORMATION: F protein

<400> SEQUENCE: 5

Met Gly Ser Lys Leu Ser Thr Arg Ile Pro Ala Pro Leu Met Leu Thr
1 5 10 15

Thr Arg Ile Thr Leu Ile Leu Ser Cys Ile Arg Pro Thr Ser Ser Leu
20 25 30

Asp Gly Arg Pro Leu Ala Ala Ala Gly Ile Val Val Thr Gly Asp Lys
35 40 45

Ala Val Asn Val Tyr Thr Ser Ser Gln Thr Gly Ser Ile Ile Val Lys
50 55 60

Leu Leu Pro Asn Met Pro Arg Asp Lys Glu Ala Cys Ala Lys Ala Pro
65 70 75 80

Leu Glu Ala Tyr Asn Arg Thr Leu Thr Thr Leu Leu Thr Pro Leu Gly
85 90 95

Asp Ser Ile Arg Lys Ile Gln Gly Ser Val Ser Thr Ser Gly Gly Gly
100 105 110

Arg Gln Ala Arg Leu Ile Gly Ala Val Ile Gly Ser Val Ala Leu Gly
115 120 125

Val Ala Thr Ala Ala Gln Ile Thr Ala Ala Ala Ala Leu Ile Gln Ala
130 135 140

Asn Gln Asn Ala Ala Asn Ile Leu Arg Leu Lys Glu Ser Ile Ala Ala
145 150 155 160

Thr Asn Glu Ala Val His Glu Val Thr Asp Gly Leu Ser Gln Leu Ser
165 170 175

Val Ala Val Gly Lys Met Gln Gln Phe Val Asn Asp Gln Phe Asn Asn
180 185 190

Thr Ala Arg Glu Leu Asp Cys Ile Lys Ile Thr Gln Gln Val Gly Val
195 200 205

Glu Leu Asn Leu Tyr Leu Thr Glu Leu Thr Thr Val Phe Gly Pro Gln
210 215 220

Ile Thr Ser Pro Ala Leu Thr Gln Leu Thr Ile Gln Ala Leu Tyr Asn
225 230 235 240

Leu Ala Gly Gly Asn Met Asn Tyr Leu Leu Thr Lys Leu Gly Ile Gly
245 250 255

Asn Asn Gln Leu Ser Ser Leu Ile Gly Ser Gly Leu Ile Thr Gly Tyr
260 265 270

Pro Ile Leu Tyr Asp Ser Gln Thr Gln Leu Leu Gly Ile Gln Val Asn
275 280 285

Leu Pro Ser Val Gly Asn Leu Asn Asn Met Arg Ala Thr Tyr Leu Glu
290 295 300

Thr Leu Ser Val Ser Thr Thr Lys Gly Tyr Ala Ser Ala Leu Val Pro
305 310 315 320

Lys Val Val Thr Gln Val Gly Ser Val Ile Glu Glu Leu Asp Thr Ser
325 330 335

Tyr Cys Ile Glu Ser Asp Leu Asp Leu Tyr Cys Thr Arg Ile Val Thr
340 345 350

Phe Pro Met Ser Pro Gly Ile Tyr Ser Cys Leu Ser Gly Asn Thr Ser
355 360 365

Ala Cys Met Tyr Ser Lys Thr Glu Gly Ala Leu Thr Thr Pro Tyr Met

```
    370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Ser
465                 470                 475                 480

Leu Ala Glu Ser Asn Ser Lys Leu Glu Lys Ile Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Phe Ser Leu Gly Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Arg Ala
545                 550


<210> SEQ ID NO 6
<211> LENGTH: 577
<212> TYPE: PRT
<213> ORGANISM: Artificial Sequence
<220> FEATURE:
<223> OTHER INFORMATION: HN protein

<400> SEQUENCE: 6

Met Asp Arg Ala Val Asn Arg Val Val Leu Glu Asn Glu Glu Arg Glu
  1               5                  10                  15

Ala Lys Asn Thr Trp Arg Leu Val Phe Arg Ile Ala Val Leu Leu Leu
             20                  25                  30

Met Val Met Thr Leu Ala Ile Ser Ser Ala Ala Leu Ala Tyr Ser Thr
         35                  40                  45

Gly Ala Ser Thr Pro His Asp Leu Ala Ser Ile Leu Thr Val Ile Ser
     50                  55                  60

Lys Thr Glu Asp Lys Val Thr Ser Leu Leu Ser Ser Ser Gln Asp Val
 65                  70                  75                  80

Ile Asp Arg Ile Tyr Lys Gln Val Ala Leu Glu Ser Pro Leu Ala Leu
                 85                  90                  95

Leu Asn Thr Glu Ser Val Ile Met Asn Ala Ile Thr Ser Leu Ser Tyr
            100                 105                 110

Gln Ile Asn Gly Ala Ala Asn Asn Ser Gly Cys Gly Ala Pro Val His
        115                 120                 125

Asp Pro Asp Tyr Ile Gly Gly Ile Gly Lys Glu Leu Ile Val Asp Asp
    130                 135                 140

Ile Ser Asp Val Thr Ser Phe Tyr Pro Ser Ala Tyr Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Thr Thr His Tyr Cys Tyr Thr His Asn Val Ile
            180                 185                 190
```

```
Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Gly
                245                 250                 255

Thr Glu Glu Glu Asp Tyr Lys Ser Val Ala Pro Thr Ser Met Val His
            260                 265                 270

Gly Arg Leu Gly Phe Asp Gly Gln Tyr His Glu Lys Asp Leu Asp Thr
        275                 280                 285

Thr Val Leu Phe Lys Asp Trp Val Ala Asn Tyr Pro Gly Ala Gly Gly
    290                 295                 300

Gly Ser Phe Ile Asp Asp Arg Val Trp Phe Pro Val Tyr Gly Gly Leu
305                 310                 315                 320

Lys Pro Asp Ser Pro Ser Asp Thr Ala Gln Glu Gly Lys Tyr Val Ile
                325                 330                 335

Tyr Lys Arg His Asn Asn Thr Cys Pro Asp Lys Gln Asp Tyr Gln Ile
            340                 345                 350

Arg Lys Ala Lys Ser Ser Tyr Lys Pro Gly Arg Phe Gly Gly Lys Arg
        355                 360                 365

Val Gln Gln Ala Ile Leu Ser Ile Lys Val Ser Thr Ser Leu Gly Lys
    370                 375                 380

Asp Pro Val Leu Thr Ile Pro Pro Asn Thr Ile Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Asn
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Ile Thr Gly Val Tyr Thr Asp Pro Tyr Pro Leu Ile Phe His Arg
465                 470                 475                 480

Asn His Thr Leu Arg Gly Val Phe Gly Thr Met Leu Asp Asp Glu Gln
                485                 490                 495

Ala Arg Leu Asn Pro Val Ser Ala Val Phe Asp Asn Val Ser Arg Ser
            500                 505                 510

Arg Val Thr Arg Val Ser Ser Ser Ser Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly

<210> SEQ ID NO 7
<211> LENGTH: 2204
<212> TYPE: PRT
<213> ORGANISM: Artificial Sequence
```

```
<220> FEATURE:
<223> OTHER INFORMATION: HN protein

<400> SEQUENCE: 7

Met Ala Ser Ser Gly Pro Glu Arg Ala Glu His Gln Ile Ile Leu Pro
  1               5                  10                  15

Glu Ser His Leu Ser Ser Pro Leu Val Lys His Lys Leu Leu Tyr Tyr
             20                  25                  30

Trp Lys Leu Thr Gly Leu Pro Leu Pro Asp Glu Cys Asp Phe Asp His
         35                  40                  45

Leu Ile Leu Ser Arg Gln Trp Lys Lys Ile Leu Glu Ser Ala Ser Pro
     50                  55                  60

Asp Thr Glu Arg Met Ile Lys Leu Gly Arg Ala Val His Gln Thr Leu
 65                  70                  75                  80

Asn His Asn Ser Arg Ile Thr Gly Val Leu His Pro Arg Cys Leu Glu
                 85                  90                  95

Glu Leu Ala Asn Ile Glu Val Pro Asp Ser Thr Asn Lys Phe Arg Lys
            100                 105                 110

Ile Glu Lys Lys Ile Gln Ile His Asn Thr Arg Tyr Gly Glu Leu Phe
        115                 120                 125

Thr Arg Leu Cys Thr His Ile Glu Lys Lys Leu Leu Gly Ser Ser Trp
    130                 135                 140

Ser Asn Asn Val Pro Arg Ser Glu Glu Phe Ser Ser Ile Arg Thr Asp
145                 150                 155                 160

Pro Ala Phe Trp Phe His Ser Lys Trp Ser Thr Ala Lys Phe Ala Trp
                165                 170                 175

Leu His Ile Lys Gln Ile Gln Arg His Leu Met Val Ala Ala Arg Thr
            180                 185                 190

Arg Ser Ala Ala Asn Lys Leu Val Met Leu Thr His Lys Val Gly Gln
        195                 200                 205

Val Phe Val Thr Pro Glu Leu Val Val Val Thr His Thr Asn Glu Asn
    210                 215                 220

Lys Phe Thr Cys Leu Thr Gln Glu Leu Val Leu Met Tyr Ala Asp Met
225                 230                 235                 240

Met Glu Gly Arg Asp Met Val Asn Ile Ile Ser Thr Thr Ala Val His
                245                 250                 255

Leu Arg Ser Leu Ser Glu Lys Ile Asp Asp Ile Leu Arg Leu Ile Asp
            260                 265                 270

Ala Leu Ala Lys Asp Leu Gly Asn Gln Val Tyr Asp Val Val Ser Leu
        275                 280                 285

Met Glu Gly Phe Ala Tyr Gly Ala Val Gln Leu Leu Glu Pro Ser Gly
    290                 295                 300

Thr Phe Ala Gly Asp Phe Phe Ala Phe Asn Leu Gln Glu Leu Lys Asp
305                 310                 315                 320

Ile Leu Ile Gly Leu Leu Pro Asn Asp Ile Ala Glu Ser Val Thr His
                325                 330                 335

Ala Ile Ala Thr Val Phe Ser Gly Leu Glu Gln Asn Gln Ala Ala Glu
            340                 345                 350

Met Leu Cys Leu Leu Arg Leu Trp Gly His Pro Leu Leu Glu Ser Arg
        355                 360                 365

Ile Ala Ala Lys Ala Val Arg Ser Gln Met Cys Ala Pro Lys Met Val
    370                 375                 380

Asp Phe Asp Met Ile Leu Gln Val Leu Ser Phe Phe Lys Gly Thr Ile
385                 390                 395                 400
```

-continued

```
Ile Asn Gly Tyr Arg Lys Lys Asn Ala Gly Val Trp Pro Arg Val Lys
                405                 410                 415

Val Asp Thr Ile Tyr Gly Lys Val Ile Gly Gln Leu His Ala Asp Ser
            420                 425                 430

Ala Glu Ile Ser His Asp Ile Met Leu Arg Glu Tyr Lys Ser Leu Ser
        435                 440                 445

Ala Leu Glu Phe Glu Pro Cys Ile Glu Tyr Asp Pro Val Thr Asn Leu
    450                 455                 460

Ser Met Phe Leu Lys Asp Lys Ala Ile Ala His Pro Asn Asp Asn Trp
465                 470                 475                 480

Leu Ala Ser Phe Arg Arg Asn Leu Leu Ser Glu Asp Gln Lys Lys His
                485                 490                 495

Val Lys Glu Ala Thr Ser Thr Asn Arg Leu Leu Ile Glu Phe Leu Glu
            500                 505                 510

Ser Asn Asp Phe Asp Pro Tyr Lys Glu Met Glu Tyr Leu Thr Thr Leu
        515                 520                 525

Glu Tyr Leu Arg Asp Asp Asn Val Ala Val Ser Tyr Ser Leu Lys Glu
    530                 535                 540

Lys Glu Val Lys Val Asn Gly Arg Ile Phe Ala Lys Leu Thr Lys Lys
545                 550                 555                 560

Leu Arg Asn Cys Gln Val Met Ala Glu Gly Ile Leu Ala Asp Gln Ile
                565                 570                 575

Ala Pro Phe Phe Gln Gly Asn Gly Val Ile Gln Asp Ser Ile Ser Leu
            580                 585                 590

Thr Lys Ser Met Leu Ala Met Ser Gln Leu Ser Phe Asn Ser Asn Lys
        595                 600                 605

Lys Arg Ile Thr Asp Cys Lys Glu Arg Val Ser Ser Asn Arg Asn His
    610                 615                 620

Asp Pro Lys Ser Lys Asn Arg Arg Arg Val Ala Thr Phe Ile Thr Thr
625                 630                 635                 640

Asp Leu Gln Lys Tyr Cys Leu Asn Trp Arg Tyr Gln Thr Ile Lys Leu
                645                 650                 655

Phe Ala His Ala Ile Asn Gln Leu Met Gly Leu Pro His Phe Phe Glu
            660                 665                 670

Trp Ile His Leu Arg Leu Met Asp Thr Thr Met Phe Val Gly Asp Pro
        675                 680                 685

Phe Asn Pro Pro Ser Asp Pro Thr Asp Cys Asp Leu Ser Arg Val Pro
    690                 695                 700

Asn Asp Asp Ile Tyr Ile Val Ser Ala Arg Gly Gly Ile Glu Gly Leu
705                 710                 715                 720

Cys Gln Lys Leu Trp Thr Met Ile Ser Ile Ala Ala Ile Gln Leu Ala
                725                 730                 735

Ala Ala Arg Ser His Cys Arg Val Ala Cys Met Val Gln Gly Asp Asn
            740                 745                 750

Gln Val Ile Ala Val Thr Arg Glu Val Arg Ser Asp Asp Ser Pro Glu
        755                 760                 765

Met Val Leu Thr Gln Leu His Gln Ala Ser Asp Asn Phe Phe Lys Glu
    770                 775                 780

Leu Ile His Val Asn His Leu Ile Gly His Asn Leu Lys Asp Arg Glu
785                 790                 795                 800

Thr Ile Arg Ser Asp Thr Phe Phe Ile Tyr Ser Lys Arg Ile Phe Lys
                805                 810                 815

Asp Gly Ala Ile Leu Ser Gln Val Leu Lys Asn Ser Ser Lys Leu Val
            820                 825                 830
```

```
Leu Val Ser Gly Asp Leu Ser Glu Asn Thr Val Met Ser Cys Ala Asn
        835                 840                 845

Ile Ala Ser Thr Val Ala Arg Leu Cys Glu Asn Gly Leu Pro Lys Asp
    850                 855                 860

Phe Cys Tyr Tyr Leu Asn Tyr Ile Met Ser Cys Val Gln Thr Tyr Phe
865                 870                 875                 880

Asp Ser Glu Phe Ser Ile Thr Asn Asn Ser His Pro Asp Leu Asn Gln
                885                 890                 895

Ser Trp Ile Glu Asp Ile Ser Phe Val His Ser Tyr Val Leu Thr Pro
            900                 905                 910

Ala Gln Leu Gly Gly Leu Ser Asn Leu Gln Tyr Ser Arg Leu Tyr Thr
        915                 920                 925

Arg Asn Ile Gly Asp Pro Gly Thr Thr Ala Phe Ala Glu Ile Lys Arg
    930                 935                 940

Leu Glu Ala Val Gly Leu Leu Ser Pro Asn Ile Met Thr Asn Ile Leu
945                 950                 955                 960

Thr Arg Pro Pro Gly Asn Gly Asp Trp Ala Ser Leu Cys Asn Asp Pro
                965                 970                 975

Tyr Ser Phe Asn Phe Glu Thr Val Ala Ser Pro Asn Ile Val Leu Lys
            980                 985                 990

Lys His Thr Gln Arg Val Leu Phe Glu Thr Cys Ser Asn Pro Leu Leu
        995                 1000                1005

Ser Gly Val His Thr Glu Asp Asn Glu Ala Glu Glu Lys Ala Leu Ala
   1010                1015                1020

Glu Phe Leu Leu Asn Gln Glu Val Ile His Pro Arg Val Ala His Ala
1025                1030                1035                1040

Ile Met Glu Ala Ser Ser Val Gly Arg Arg Lys Gln Ile Gln Gly Leu
               1045                1050                1055

Val Asp Thr Thr Asn Thr Val Ile Lys Ile Ala Leu Thr Arg Arg Pro
           1060                1065                1070

Leu Gly Ile Lys Arg Leu Met Arg Ile Val Asn Tyr Ser Ser Met His
       1075                1080                1085

Ala Met Leu Phe Arg Asp Asp Val Phe Ser Ser Ser Arg Ser Asn His
   1090                1095                1100

Pro Leu Val Ser Ser Asn Met Cys Ser Leu Thr Leu Ala Asp Tyr Ala
1105                1110                1115                1120

Arg Asn Arg Ser Trp Ser Pro Leu Thr Gly Gly Arg Lys Ile Leu Gly
               1125                1130                1135

Val Ser Asn Pro Asp Thr Ile Glu Leu Val Glu Gly Glu Ile Leu Ser
           1140                1145                1150

Val Ser Gly Gly Cys Thr Arg Cys Asp Ser Gly Asp Glu Gln Phe Thr
       1155                1160                1165

Trp Phe His Leu Pro Ser Asn Ile Glu Leu Thr Asp Asp Thr Ser Lys
   1170                1175                1180

Asn Pro Pro Met Arg Val Pro Tyr Leu Gly Ser Lys Thr Gln Glu Arg
1185                1190                1195                1200

Arg Ala Ala Ser Leu Ala Lys Ile Ala His Met Ser Pro His Val Lys
               1205                1210                1215

Ala Ala Leu Arg Ala Ser Ser Val Leu Ile Trp Ala Tyr Gly Asp Asn
           1220                1225                1230

Glu Val Asn Trp Thr Ala Ala Leu Thr Ile Ala Lys Ser Arg Cys Asn
       1235                1240                1245

Val Asn Leu Glu Tyr Leu Arg Leu Leu Ser Pro Leu Pro Thr Ala Gly
```

```
   1250                1255                1260

Asn Leu Gln His Arg Leu Asp Asp Gly Ile Thr Gln Met Thr Phe Thr
1265                1270                1275                1280

Pro Ala Ser Leu Tyr Arg Val Ser Pro Tyr Ile His Ile Ser Asn Asp
                1285                1290                1295

Ser Gln Arg Leu Phe Thr Glu Glu Gly Val Lys Glu Gly Asn Val Val
            1300                1305                1310

Tyr Gln Gln Ile Met Leu Leu Gly Leu Ser Leu Ile Glu Ser Ile Phe
        1315                1320                1325

Pro Met Thr Thr Thr Arg Thr Tyr Asp Glu Ile Thr Leu His Leu His
   1330                1335                1340

Ser Lys Phe Ser Cys Cys Ile Arg Glu Ala Pro Val Ala Val Pro Phe
1345                1350                1355                1360

Glu Leu Leu Gly Val Val Pro Glu Leu Arg Thr Val Thr Ser Asn Lys
                1365                1370                1375

Phe Met Tyr Asp Pro Ser Pro Val Ser Glu Gly Asp Phe Ala Arg Leu
            1380                1385                1390

Asp Leu Ala Ile Phe Lys Ser Tyr Glu Leu Asn Leu Glu Ser Tyr Pro
        1395                1400                1405

Thr Ile Glu Leu Met Asn Ile Leu Ser Ile Ser Ser Gly Lys Leu Ile
   1410                1415                1420

Gly Gln Ser Val Val Ser Tyr Asp Glu Asp Thr Ser Ile Lys Asn Asp
1425                1430                1435                1440

Ala Ile Ile Val Tyr Asp Asn Thr Arg Asn Trp Ile Ser Glu Ala Gln
                1445                1450                1455

Asn Ser Asp Val Val Arg Leu Phe Glu Tyr Ala Ala Leu Glu Val Leu
            1460                1465                1470

Leu Asp Cys Ser Tyr Gln Leu Tyr Tyr Leu Arg Val Arg Gly Leu Asp
        1475                1480                1485

Asn Ile Val Leu Tyr Met Gly Asp Leu Tyr Lys Asn Met Pro Gly Ile
   1490                1495                1500

Leu Leu Ser Asn Ile Ala Ala Thr Ile Ser His Pro Val Ile His Ser
1505                1510                1515                1520

Arg Leu His Ala Val Gly Leu Val Asn His Asp Gly Ser His Gln Leu
                1525                1530                1535

Ala Asp Thr Asp Phe Ile Glu Met Ser Ala Lys Leu Leu Val Ser Cys
            1540                1545                1550

Thr Arg Arg Val Ile Ser Gly Leu Tyr Ser Gly Asn Lys Tyr Asp Leu
        1555                1560                1565

Leu Phe Pro Ser Val Leu Asp Asp Asn Leu Asn Glu Lys Met Leu Gln
   1570                1575                1580

Leu Ile Ser Arg Leu Cys Cys Leu Tyr Thr Val Leu Phe Ala Thr Thr
1585                1590                1595                1600

Arg Glu Ile Pro Lys Ile Arg Gly Leu Thr Ala Glu Glu Lys Cys Ser
                1605                1610                1615

Ile Leu Thr Glu Tyr Leu Leu Ser Asp Ala Val Lys Pro Leu Leu Ser
            1620                1625                1630

Pro Asp Gln Val Ser Ser Ile Met Ser Pro Asn Ile Ile Thr Phe Pro
        1635                1640                1645

Ala Asn Leu Tyr Tyr Met Ser Arg Lys Ser Leu Asn Leu Ile Arg Glu
   1650                1655                1660

Arg Glu Asp Arg Asp Thr Ile Leu Ala Leu Leu Phe Pro Gln Glu Pro
1665                1670                1675                1680
```

-continued

```
Leu Leu Glu Phe Pro Ser Val Gln Asp Ile Gly Ala Arg Val Lys Asp
                1685                1690                1695

Pro Phe Thr Arg Gln Pro Ala Ala Phe Leu Gln Glu Leu Asp Leu Ser
            1700                1705                1710

Ala Pro Ala Arg Tyr Asp Ala Phe Thr Leu Ser Gln Ile His Pro Glu
        1715                1720                1725

Leu Thr Ser Pro Asn Pro Glu Glu Asp Tyr Leu Val Arg Tyr Leu Phe
    1730                1735                1740

Arg Gly Ile Gly Thr Ala Ser Ser Ser Trp Tyr Lys Ala Ser His Leu
1745                1750                1755                1760

Leu Ser Val Pro Glu Val Arg Cys Ala Arg His Gly Asn Ser Leu Tyr
                1765                1770                1775

Leu Ala Glu Gly Ser Gly Ala Ile Met Ser Leu Leu Glu Leu His Val
            1780                1785                1790

Pro His Glu Thr Ile Tyr Tyr Asn Thr Leu Phe Ser Asn Glu Met Asn
        1795                1800                1805

Pro Pro Gln Arg His Phe Gly Pro Thr Pro Thr Gln Phe Leu Asn Ser
    1810                1815                1820

Val Val Tyr Arg Asn Leu Gln Ala Glu Val Thr Cys Lys Asp Gly Phe
1825                1830                1835                1840

Val Gln Glu Phe Arg Pro Leu Trp Arg Glu Asn Thr Glu Glu Ser Asp
                1845                1850                1855

Leu Thr Ser Asp Lys Ala Val Gly Tyr Ile Thr Ser Ala Val Pro Tyr
            1860                1865                1870

Arg Ser Val Ser Leu Leu His Cys Asp Ile Glu Ile Pro Pro Gly Ser
        1875                1880                1885

Asn Gln Ser Leu Leu Asp Gln Leu Ala Ile Asn Leu Ser Leu Ile Ala
    1890                1895                1900

Met His Ser Val Arg Glu Gly Gly Val Val Ile Ile Lys Val Leu Tyr
1905                1910                1915                1920

Ala Met Gly Tyr Tyr Phe His Leu Leu Met Asn Leu Phe Ala Pro Cys
                1925                1930                1935

Ser Thr Lys Gly Tyr Ile Leu Ser Asn Gly Tyr Ala Cys Arg Gly Asp
            1940                1945                1950

Met Glu Cys Tyr Leu Val Phe Val Met Gly Tyr Leu Gly Gly Pro Thr
        1955                1960                1965

Phe Val His Glu Val Val Arg Met Ala Lys Thr Leu Val Gln Arg His
    1970                1975                1980

Gly Thr Leu Leu Ser Lys Ser Asp Glu Ile Thr Leu Thr Arg Leu Phe
1985                1990                1995                2000

Thr Ser Gln Arg Gln Arg Val Thr Asp Ile Leu Ser Ser Pro Leu Pro
                2005                2010                2015

Arg Leu Ile Lys Tyr Leu Arg Lys Asn Ile Asp Thr Ala Leu Ile Glu
            2020                2025                2030

Ala Gly Gly Gln Pro Val Arg Pro Phe Cys Ala Glu Ser Leu Val Ser
        2035                2040                2045

Thr Leu Ala Asn Ile Thr Gln Ile Thr Gln Ile Ile Ala Ser His Ile
    2050                2055                2060

Asp Thr Val Ile Arg Ser Val Ile Tyr Met Glu Ala Glu Gly Asp Leu
2065                2070                2075                2080

Ala Asp Thr Val Phe Leu Phe Thr Pro Tyr Asn Leu Ser Thr Asp Gly
                2085                2090                2095

Lys Lys Arg Thr Ser Leu Lys Gln Cys Thr Arg Gln Ile Leu Glu Val
            2100                2105                2110
```

```
Thr Ile Leu Gly Leu Arg Val Glu Asn Leu Asn Lys Ile Gly Asp Ile
       2115                2120                2125

Ile Ser Leu Val Leu Lys Gly Met Ile Ser Met Glu Asp Leu Ile Pro
   2130                2135                2140

Leu Arg Thr Tyr Leu Lys His Ser Thr Cys Pro Lys Tyr Leu Lys Ala
2145                2150                2155                2160

Val Leu Gly Ile Thr Lys Leu Lys Glu Met Phe Thr Asp Thr Ser Val
               2165                2170                2175

Leu Tyr Leu Thr Arg Ala Gln Gln Lys Phe Tyr Met Lys Thr Ile Gly
           2180                2185                2190

Asn Ala Val Lys Gly Tyr Tyr Ser Asn Cys Asp Ser
       2195                2200


<210> SEQ ID NO 8
<211> LENGTH: 32
<212> TYPE: DNA
<213> ORGANISM: Artificial Sequence
<220> FEATURE:
<223> OTHER INFORMATION: ND-ZJ-1F primer

<400> SEQUENCE: 8

cgtctcgacc aaacagagaa tctgtgaggt ac                                32


<210> SEQ ID NO 9
<211> LENGTH: 20
<212> TYPE: DNA
<213> ORGANISM: Artificial Sequence
<220> FEATURE:
<223> OTHER INFORMATION: ND-ZJ-1746F primer

<400> SEQUENCE: 9

gacaacacag gcacagctcg                                              20


<210> SEQ ID NO 10
<211> LENGTH: 22
<212> TYPE: DNA
<213> ORGANISM: Artificial Sequence
<220> FEATURE:
<223> OTHER INFORMATION: ND-ZJ-2827F primer

<400> SEQUENCE: 10

catctcctta cgtgacacaa gg                                           22


<210> SEQ ID NO 11
<211> LENGTH: 28
<212> TYPE: DNA
<213> ORGANISM: Artificial Sequence
<220> FEATURE:
<223> OTHER INFORMATION: ND-ZJ-F-F primer

<400> SEQUENCE: 11

tcgcgacgca atatggctcc aaactttc                                     28


<210> SEQ ID NO 12
<211> LENGTH: 30
<212> TYPE: DNA
<213> ORGANISM: Artificial Sequence
<220> FEATURE:
<223> OTHER INFORMATION: ND-ZJ-HN-F primer

<400> SEQUENCE: 12

ccgcggcacc gacaacaaga gtcaatcatg                                   30
```

<210> SEQ ID NO 13
<211> LENGTH: 27
<212> TYPE: DNA
<213> ORGANISM: Artificial Sequence
<220> FEATURE:
<223> OTHER INFORMATION: ND-ZJ-8100F primer

<400> SEQUENCE: 13
actagttgag atcctcaagg atgatag 27

<210> SEQ ID NO 14
<211> LENGTH: 22
<212> TYPE: DNA
<213> ORGANISM: Artificial Sequence
<220> FEATURE:
<223> OTHER INFORMATION: ND-ZJ-11648F primer

<400> SEQUENCE: 14
catgcaatgt tgtccagaga tg 22

<210> SEQ ID NO 15
<211> LENGTH: 22
<212> TYPE: DNA
<213> ORGANISM: Artificial Sequence
<220> FEATURE:
<223> OTHER INFORMATION: ND-ZJ-12539F primer

<400> SEQUENCE: 15
tcagagagag atttcgcgag ac 22

<210> SEQ ID NO 16
<211> LENGTH: 23
<212> TYPE: DNA
<213> ORGANISM: Artificial Sequence
<220> FEATURE:
<223> OTHER INFORMATION: ND-ZJ-14021F primer

<400> SEQUENCE: 16
cattgtgaca ttgagattcc tcc 23

<210> SEQ ID NO 17
<211> LENGTH: 23
<212> TYPE: DNA
<213> ORGANISM: Artificial Sequence
<220> FEATURE:
<223> OTHER INFORMATION: ND-ZJ-1844R primer

<400> SEQUENCE: 17
tcgtcttggt ctctggatgt ctc 23

<210> SEQ ID NO 18
<211> LENGTH: 21
<212> TYPE: DNA
<213> ORGANISM: Artificial Sequence
<220> FEATURE:
<223> OTHER INFORMATION: ND-ZJ-2948R primer

<400> SEQUENCE: 18
cttctccact cccatgtcag g 21

<210> SEQ ID NO 19
<211> LENGTH: 22
<212> TYPE: DNA
<213> ORGANISM: Artificial Sequence
<220> FEATURE:
<223> OTHER INFORMATION: ND-ZJ-4612R primer

<400> SEQUENCE: 19
cagcataatc cgggtgatca gc 22

<210> SEQ ID NO 20
<211> LENGTH: 30
<212> TYPE: DNA
<213> ORGANISM: Artificial Sequence
<220> FEATURE:
<223> OTHER INFORMATION: ND-ZJ-F-R primer

<400> SEQUENCE: 20
ccgcggtaga acggatgttg tgaagcctaa 30

<210> SEQ ID NO 21
<211> LENGTH: 31
<212> TYPE: DNA
<213> ORGANISM: Artificial Sequence
<220> FEATURE:
<223> OTHER INFORMATION: ND-ZJ-HN-R primer

<400> SEQUENCE: 21
ctcaactagt aagggaacga tcctaaattc c 31

<210> SEQ ID NO 22
<211> LENGTH: 24
<212> TYPE: DNA
<213> ORGANISM: Artificial Sequence
<220> FEATURE:
<223> OTHER INFORMATION: ND-ZJ-11815R primer

<400> SEQUENCE: 22
tatggtatca gggttggata cacc 24

<210> SEQ ID NO 23
<211> LENGTH: 23
<212> TYPE: DNA
<213> ORGANISM: Artificial Sequence
<220> FEATURE:
<223> OTHER INFORMATION: ND-ZJ-12591R primer

<400> SEQUENCE: 23
agctcataac tcttgaagat agc 23

<210> SEQ ID NO 24
<211> LENGTH: 22
<212> TYPE: DNA
<213> ORGANISM: Artificial Sequence
<220> FEATURE:
<223> OTHER INFORMATION: ND-ZJ-14110R primer

<400> SEQUENCE: 24
cacagaatgc atggcaatca gg 22

<210> SEQ ID NO 25
<211> LENGTH: 22
<212> TYPE: DNA
<213> ORGANISM: Artificial Sequence
<220> FEATURE:
<223> OTHER INFORMATION: ND-ZJ-15118R primer

<400> SEQUENCE: 25
actgaatccg aatacgactt cc 22

<210> SEQ ID NO 26
<211> LENGTH: 21
<212> TYPE: DNA
<213> ORGANISM: Artificial Sequence
<220> FEATURE:
<223> OTHER INFORMATION: ND-ZJ-597F primer

<400> SEQUENCE: 26
ctgacactct ggaaagaatc c 21

<210> SEQ ID NO 27
<211> LENGTH: 20
<212> TYPE: DNA
<213> ORGANISM: Artificial Sequence
<220> FEATURE:
<223> OTHER INFORMATION: ND-ZJ-3421F primer

<400> SEQUENCE: 27
gatccagcgc cttgattcgt 20

<210> SEQ ID NO 28
<211> LENGTH: 21
<212> TYPE: DNA
<213> ORGANISM: Artificial Sequence
<220> FEATURE:
<223> OTHER INFORMATION: ND-ZJ-8662F primer

<400> SEQUENCE: 28
caggtgttta gaagaactgg c 21

<210> SEQ ID NO 29
<211> LENGTH: 20
<212> TYPE: DNA
<213> ORGANISM: Artificial Sequence
<220> FEATURE:
<223> OTHER INFORMATION: ND-ZJ-5759F primer

<400> SEQUENCE: 29
cctcctggta tcatatcgca 20

<210> SEQ ID NO 30
<211> LENGTH: 21
<212> TYPE: DNA
<213> ORGANISM: Artificial Sequence
<220> FEATURE:
<223> OTHER INFORMATION: ND-ZJ-4679 primer

<400> SEQUENCE: 30
gtaacaggag ataaggcagt c 21

<210> SEQ ID NO 31
<211> LENGTH: 20
<212> TYPE: DNA
<213> ORGANISM: Artificial Sequence
<220> FEATURE:
<223> OTHER INFORMATION: ND-ZJ-7670 primer

<400> SEQUENCE: 31
ttcttgtacc aacgagggtc 20

<210> SEQ ID NO 32
<211> LENGTH: 21
<212> TYPE: DNA
<213> ORGANISM: Artificial Sequence
<220> FEATURE:
<223> OTHER INFORMATION: ND-ZJ-9328F primer

<400> SEQUENCE: 32
cctacaggag ctcaaagaca c 21

<210> SEQ ID NO 33
<211> LENGTH: 20
<212> TYPE: DNA
<213> ORGANISM: Artificial Sequence
<220> FEATURE:
<223> OTHER INFORMATION: ND-ZJ-9977F primer

<400> SEQUENCE: 33
ctaagagatg acagtgtggc 20

<210> SEQ ID NO 34
<211> LENGTH: 20
<212> TYPE: DNA
<213> ORGANISM: Artificial Sequence
<220> FEATURE:
<223> OTHER INFORMATION: ND-ZJ-10588F primer

<400> SEQUENCE: 34
acttgctgca gcaagatctc 20

<210> SEQ ID NO 35
<211> LENGTH: 20
<212> TYPE: DNA
<213> ORGANISM: Artificial Sequence
<220> FEATURE:
<223> OTHER INFORMATION: ND-ZJ-13052F primer

<400> SEQUENCE: 35
gtggtctcag gcttatatgc 20

<210> SEQ ID NO 36
<211> LENGTH: 33
<212> TYPE: DNA
<213> ORGANISM: Artificial Sequence
<220> FEATURE:
<223> OTHER INFORMATION: S1-F primer

<400> SEQUENCE: 36
cgtctcgacc aaacagagaa tccgtgagtt acg 33

<210> SEQ ID NO 37
<211> LENGTH: 26
<212> TYPE: DNA
<213> ORGANISM: Artificial Sequence
<220> FEATURE:
<223> OTHER INFORMATION: S1-R primer

<400> SEQUENCE: 37
ccatgggccc tttttagcat tggacg 26

<210> SEQ ID NO 38
<211> LENGTH: 22
<212> TYPE: DNA
<213> ORGANISM: Artificial Sequence
<220> FEATURE:
<223> OTHER INFORMATION: S2-F primer

<400> SEQUENCE: 38
aaaagggccc atggtcgagc cc 22

<210> SEQ ID NO 39
<211> LENGTH: 23
<212> TYPE: DNA
<213> ORGANISM: Artificial Sequence
<220> FEATURE:
<223> OTHER INFORMATION: S2-R primer

<400> SEQUENCE: 39
tatcatcgat catgccgaca gtg 23

<210> SEQ ID NO 40
<211> LENGTH: 23
<212> TYPE: DNA
<213> ORGANISM: Artificial Sequence
<220> FEATURE:
<223> OTHER INFORMATION: S3-F primer

<400> SEQUENCE: 40
catgatcgat gataaaccca agc 23

<210> SEQ ID NO 41
<211> LENGTH: 28
<212> TYPE: DNA
<213> ORGANISM: Artificial Sequence
<220> FEATURE:
<223> OTHER INFORMATION: S3-R primer

<400> SEQUENCE: 41
tcgcgaatga gccggtcggg atccagac 28

<210> SEQ ID NO 42
<211> LENGTH: 28
<212> TYPE: DNA
<213> ORGANISM: Artificial Sequence
<220> FEATURE:
<223> OTHER INFORMATION: S4-F primer

<400> SEQUENCE: 42
tcgcgacgca atatggctcc aaactttc 28

<210> SEQ ID NO 43
<211> LENGTH: 30
<212> TYPE: DNA
<213> ORGANISM: Artificial Sequence
<220> FEATURE:
<223> OTHER INFORMATION: S4-R primer

<400> SEQUENCE: 43
ccgcggtaga acggatgttg tgaagcctaa 30

<210> SEQ ID NO 44
<211> LENGTH: 30
<212> TYPE: DNA
<213> ORGANISM: Artificial Sequence
<220> FEATURE:
<223> OTHER INFORMATION: S5-F primer

<400> SEQUENCE: 44
ccgcggcacc gacaacaaga gtcaatcatg 30

<210> SEQ ID NO 45
<211> LENGTH: 31
<212> TYPE: DNA
<213> ORGANISM: Artificial Sequence
<220> FEATURE:
<223> OTHER INFORMATION: S5-R primer

<400> SEQUENCE: 45
ctcaactagt aagggaacga tcctaaattc c 31

<210> SEQ ID NO 46
<211> LENGTH: 27
<212> TYPE: DNA
<213> ORGANISM: Artificial Sequence
<220> FEATURE:
<223> OTHER INFORMATION: S6-F primer

<400> SEQUENCE: 46
actagttgag atcctcaagg atgatag 27

<210> SEQ ID NO 47
<211> LENGTH: 25
<212> TYPE: DNA
<213> ORGANISM: Artificial Sequence
<220> FEATURE:
<223> OTHER INFORMATION: S7-R primer

<400> SEQUENCE: 47
gatccgtacg aatgcagctg aactc 25

<210> SEQ ID NO 48
<211> LENGTH: 24
<212> TYPE: DNA
<213> ORGANISM: Artificial Sequence
<220> FEATURE:
<223> OTHER INFORMATION: S9-F primer

<400> SEQUENCE: 48
cctaggtatt accaaactca aaga 24

<210> SEQ ID NO 49
<211> LENGTH: 30
<212> TYPE: DNA
<213> ORGANISM: Artificial Sequence
<220> FEATURE:
<223> OTHER INFORMATION: S9-R primer

<400> SEQUENCE: 49
ggtctcaacc aaacaaagat ttggtgaatg 30

<210> SEQ ID NO 50
<211> LENGTH: 19
<212> TYPE: DNA
<213> ORGANISM: Artificial Sequence
<220> FEATURE:
<223> OTHER INFORMATION: La-601 primer

<400> SEQUENCE: 50
taccctggag aggatcctc 19

<210> SEQ ID NO 51
<211> LENGTH: 20
<212> TYPE: DNA
<213> ORGANISM: Artificial Sequence
<220> FEATURE:
<223> OTHER INFORMATION: La-1261 primer

<400> SEQUENCE: 51
cgagctaaag ctaaccccag 20

<210> SEQ ID NO 52
<211> LENGTH: 20
<212> TYPE: DNA
<213> ORGANISM: Artificial Sequence
<220> FEATURE:
<223> OTHER INFORMATION: La-1901 primer

<400> SEQUENCE: 52
agatgcagag atcgacgagc 20

<210> SEQ ID NO 53
<211> LENGTH: 20
<212> TYPE: DNA
<213> ORGANISM: Artificial Sequence
<220> FEATURE:
<223> OTHER INFORMATION: La-2581 primer

<400> SEQUENCE: 53
aggcgatatc acagagagta 20

<210> SEQ ID NO 54
<211> LENGTH: 19
<212> TYPE: DNA
<213> ORGANISM: Artificial Sequence
<220> FEATURE:
<223> OTHER INFORMATION: La-3271 primer

<400> SEQUENCE: 54
gtgccccaat tgtgccaag 19

<210> SEQ ID NO 55
<211> LENGTH: 27
<212> TYPE: DNA
<213> ORGANISM: Artificial Sequence
<220> FEATURE:
<223> OTHER INFORMATION: S6-F-La priemr

<400> SEQUENCE: 55
actagttgag atcctcaaag atgacgg 27

<210> SEQ ID NO 56
<211> LENGTH: 33
<212> TYPE: DNA
<213> ORGANISM: Artificial Sequence
<220> FEATURE:
<223> OTHER INFORMATION: S6-R-La primer

<400> SEQUENCE: 56
tgctctgccc tttcaggacc ggagctcgcc atg 33

<210> SEQ ID NO 57
<211> LENGTH: 33
<212> TYPE: DNA
<213> ORGANISM: Artificial Sequence
<220> FEATURE:
<223> OTHER INFORMATION: S7-F-La primer

<400> SEQUENCE: 57
catggcgagc tccggtcctg aaagggcaga gca 33

<210> SEQ ID NO 58
<211> LENGTH: 20
<212> TYPE: DNA
<213> ORGANISM: Artificial Sequence
<220> FEATURE:
<223> OTHER INFORMATION: La-5121 primer

<400> SEQUENCE: 58
cagctcagga attagactgc 20

<210> SEQ ID NO 59
<211> LENGTH: 20
<212> TYPE: DNA
<213> ORGANISM: Artificial Sequence
<220> FEATURE:
<223> OTHER INFORMATION: La-5711 primer

<400> SEQUENCE: 59

-continued gtcatcgcca actgcaagat 20

<210> SEQ ID NO 60
<211> LENGTH: 19
<212> TYPE: DNA
<213> ORGANISM: Artificial Sequence
<220> FEATURE:
<223> OTHER INFORMATION: La-7042 primer

<400> SEQUENCE: 60
ctccggacat ctgcaacag 19

<210> SEQ ID NO 61
<211> LENGTH: 19
<212> TYPE: DNA
<213> ORGANISM: Artificial Sequence
<220> FEATURE:
<223> OTHER INFORMATION: La-8591 primer

<400> SEQUENCE: 61
aaactcggaa gggcagtac 19

<210> SEQ ID NO 62
<211> LENGTH: 19
<212> TYPE: DNA
<213> ORGANISM: Artificial Sequence
<220> FEATURE:
<223> OTHER INFORMATION: La-9311 primer

<400> SEQUENCE: 62
ttcgcattca acctgcagg 19

<210> SEQ ID NO 63
<211> LENGTH: 20
<212> TYPE: DNA
<213> ORGANISM: Artificial Sequence
<220> FEATURE:
<223> OTHER INFORMATION: La-9971 primer

<400> SEQUENCE: 63
cttagagatg acaatgtggc 20

<210> SEQ ID NO 64
<211> LENGTH: 20
<212> TYPE: DNA
<213> ORGANISM: Artificial Sequence
<220> FEATURE:
<223> OTHER INFORMATION: La-10661 primer

<400> SEQUENCE: 64
gtaagatcag acgactctcc 20

<210> SEQ ID NO 65
<211> LENGTH: 19
<212> TYPE: DNA
<213> ORGANISM: Artificial Sequence
<220> FEATURE:
<223> OTHER INFORMATION: La-11321 primer

<400> SEQUENCE: 65
tttgagactg ttgcaagcc 19

<210> SEQ ID NO 66
<211> LENGTH: 19
<212> TYPE: DNA
<213> ORGANISM: Artificial Sequence
<220> FEATURE:
<223> OTHER INFORMATION: La-12012 primer

<400> SEQUENCE: 66
tgtcgccaca tgtaaaggc 19

<210> SEQ ID NO 67
<211> LENGTH: 20
<212> TYPE: DNA
<213> ORGANISM: Artificial Sequence
<220> FEATURE:
<223> OTHER INFORMATION: La-12721 primer

<400> SEQUENCE: 67
tacccgaaat tggatcagtg 20

<210> SEQ ID NO 68
<211> LENGTH: 19
<212> TYPE: DNA
<213> ORGANISM: Artificial Sequence
<220> FEATURE:
<223> OTHER INFORMATION: La-13339 primer

<400> SEQUENCE: 68
catgtctcgg aagagcctc 19

<210> SEQ ID NO 69
<211> LENGTH: 19
<212> TYPE: DNA
<213> ORGANISM: Artificial Sequence
<220> FEATURE:
<223> OTHER INFORMATION: La-13981 primer

<400> SEQUENCE: 69
atctgcagtg ccctacaga 19

<210> SEQ ID NO 70
<211> LENGTH: 45
<212> TYPE: DNA
<213> ORGANISM: Artificial Sequence
<220> FEATURE:
<223> OTHER INFORMATION: La14976 primer

<400> SEQUENCE: 70
acagtaactg tgactcttaa cgaaaatcac atattaatag gctcc 45

<210> SEQ ID NO 71
<211> LENGTH: 45
<212> TYPE: DNA
<213> ORGANISM: Artificial Sequence
<220> FEATURE:
<223> OTHER INFORMATION: La15020R primer

<400> SEQUENCE: 71
ggagcctatt aatatgtgat tttcgttaag agtcacagtt actgt 45

<210> SEQ ID NO 72
<211> LENGTH: 25
<212> TYPE: DNA
<213> ORGANISM: Artificial Sequence
<220> FEATURE:
<223> OTHER INFORMATION: S7-R primer

<400> SEQUENCE: 72
gatccgtacg aatgctgctg aactc 25

<210> SEQ ID NO 73
<211> LENGTH: 20
<212> TYPE: DNA
<213> ORGANISM: Artificial Sequence
<220> FEATURE:
<223> OTHER INFORMATION: NDV-Pt-R primer

<400> SEQUENCE: 73
tgccactgmt agttgygata 20

<210> SEQ ID NO 74
<211> LENGTH: 20
<212> TYPE: DNA
<213> ORGANISM: Artificial Sequence
<220> FEATURE:
<223> OTHER INFORMATION: NDcomF156 primer

<400> SEQUENCE: 74
atacacctcr tcycagacag 20

<210> SEQ ID NO 75
<211> LENGTH: 26
<212> TYPE: DNA
<213> ORGANISM: Artificial Sequence
<220> FEATURE:
<223> OTHER INFORMATION: La-8892R primer

<400> SEQUENCE: 75
gagccatgca aacttggctg tggacc 26

<210> SEQ ID NO 76
<211> LENGTH: 20
<212> TYPE: DNA
<213> ORGANISM: Artificial Sequence
<220> FEATURE:
<223> OTHER INFORMATION: La-14708 primer

<400> SEQUENCE: 76
acagtgcacg agacagatcc 20

<210> SEQ ID NO 77
<211> LENGTH: 20
<212> TYPE: DNA
<213> ORGANISM: Artificial Sequence
<220> FEATURE:
<223> OTHER INFORMATION: La-15092R primer

<400> SEQUENCE: 77
gtcctaagga gtcagggttc 20

<210> SEQ ID NO 78
<211> LENGTH: 31
<212> TYPE: DNA
<213> ORGANISM: Artificial Sequence
<220> FEATURE:
<223> OTHER INFORMATION: NDV-NP-F primer

<400> SEQUENCE: 78
gagcggccgc accatgagta cgagcagctc c 31

<210> SEQ ID NO 79
<211> LENGTH: 29
<212> TYPE: DNA
<213> ORGANISM: Artificial Sequence
<220> FEATURE:
<223> OTHER INFORMATION: NDV-NP-R primer

<400> SEQUENCE: 79

-continued gagcggccgc tcagtacccc cagtcggtg 29

<210> SEQ ID NO 80
<211> LENGTH: 32
<212> TYPE: DNA
<213> ORGANISM: Artificial Sequence
<220> FEATURE:
<223> OTHER INFORMATION: NDV-P-F primer

<400> SEQUENCE: 80
gagcggccgc accatggcca cctttacaga tg 32

<210> SEQ ID NO 81
<211> LENGTH: 30
<212> TYPE: DNA
<213> ORGANISM: Artificial Sequence
<220> FEATURE:
<223> OTHER INFORMATION: NDV-P-R primer

<400> SEQUENCE: 81
gagcggccgc ttagccattt agagcaaggc 30

<210> SEQ ID NO 82
<211> LENGTH: 36
<212> TYPE: DNA
<213> ORGANISM: Artificial Sequence
<220> FEATURE:
<223> OTHER INFORMATION: NDV-L-F primer

<400> SEQUENCE: 82
gagcggccgc accatggcga gcctccgatc ctgaaa 36

<210> SEQ ID NO 83
<211> LENGTH: 37
<212> TYPE: DNA
<213> ORGANISM: Artificial Sequence
<220> FEATURE:
<223> OTHER INFORMATION: NDV-L-R primer

<400> SEQUENCE: 83
gagcggccgc ttaagagtca cagttactgt aatatcc 37

<210> SEQ ID NO 84
<211> LENGTH: 2357
<212> TYPE: DNA
<213> ORGANISM: Artificial Sequence
<220> FEATURE:
<223> OTHER INFORMATION: Nucleotide sequence of pTMH vector

<400> SEQUENCE: 84
gaattctaat acgactcact ataggaccaa gagacgggcc catatcgatt cgcgaccgcg 60
ggatactagt cgtacgccta ggggtctctt ggtgggtcgg catggcatct ccacctcctc 120
gcggtccgac ctgggcatcc gaaggaggac gtcgtccact cggatggcta agggagagct 180
cggatccggc tgctaacaaa gcccgaaagg aagctgagtt ggctgctgcc accgctgagc 240
aataactagc ataacccctt ggggcctcta aacgggtctt gaggggtttt ttgcatatgc 300
ggtgtgaaat accgcacaga tgcgtaagga gaaaataccg catcaggcgc tcttccgctt 360
cctcgctcac tgactcgctg cgctcggtcg ttcggctgcg gcgagcggta tcagctcact 420
caaaggcggt aatacggtta tccacagaat caggggataa cgcaggaaag aacatgtgag 480
caaaaggcca gcaaaaggcc aggaaccgta aaaaggccgc gttgctggcg tttttccata 540
ggctccgccc ccctgacgag catcacaaaa atcgacgctc aagtcagagg tggcgaaacc 600

-continued cgacaggact ataaagatac caggcgtttc cccctggaag ctccctcgtg cgctctcctg 660
ttccgaccct gccgcttacc ggatacctgt ccgcctttct cccttcggga agcgtggcgc 720
tttctcatag ctcacgctgt aggtatctca gttcggtgta ggtcgttcgc tccaagctgg 780
gctgtgtgca cgaacccccc gttcagcccg accgctgcgc cttatccggt aactatcgtc 840
ttgagtccaa cccggtaaga cacgacttat cgccactggc agcagccact ggtaacagga 900
ttagcagagc gaggtatgta ggcggtgcta cagagttctt gaagtggtgg cctaactacg 960
gctacactag aaggacagta tttggtatct gcgctctgct gaagccagtt accttcggaa 1020
aaagagttgg tagctcttga tccggcaaac aaaccaccgc tggtagcggt ggtttttttg 1080
tttgcaagca gcagattacg cgcagaaaaa aaggatctca agaagatcct ttgatctttt 1140
ctacggggtc tgacgctcag tggaacgaaa actcacgtta agggattttg gtcatgagat 1200
tatcaaaaag gatcttcacc tagatccttt taaattaaaa atgaagtttt aaatcaatct 1260
aaagtatata tgagtaaact tggtctgaca gttaccaatg cttaatcagt gaggcaccta 1320
tctcagcgat ctgtctattt cgttcatcca tagttgcctg actccccgtc gtgtagataa 1380
ctacgatacg ggagggctta ccatctggcc ccagtgctgc aatgataccg cgagacccac 1440
gctcaccggc tccagattta tcagcaataa accagccagc cggaagggcc gagcgcagaa 1500
gtggtcctgc aactttatcc gcctccatcc agtctattaa ttgttgccgg gaagctagag 1560
taagtagttc gccagttaat agtttgcgca acgttgttgc cattgctgca ggcatcgtgg 1620
tgtcacgctc gtcgtttggt atggcttcat tcagctccgg ttcccaacga tcaaggcgag 1680
ttacatgatc ccccatgttg tgcaaaaaag cggttagctc cttcggtcct ccgatcgttg 1740
tcagaagtaa gttggccgca gtgttatcac tcatggttat ggcagcactg cataattctc 1800
ttactgtcat gccatccgta agatgctttt ctgtgactgg tgagtactca accaagtcat 1860
tctgagaata gtgtatgcgg cgaccgagtt gctcttgccc ggcgtcaaca cgggataata 1920
ccgcgccaca tagcagaact ttaaaagtgc tcatcattgg aaaacgttct tcggggcgaa 1980
aactctcaag gatcttaccg ctgttgagat ccagttcgat gtaacccact cgtgcaccca 2040
actgatcttc agcatctttt actttcacca gcgtttctgg gtgagcaaaa acaggaaggc 2100
aaaatgccgc aaaaaaggga ataagggcga cacggaaatg ttgaatactc atactcttcc 2160
tttttcaata ttattgaagc atttatcagg gttattgtct catgagcgga tacatatttg 2220
aatgtattta gaaaaataaa caaatagggg ttccgcgcac atttccccga aaagtgccac 2280
ctgacgtcta agaaaccatt attatcatga cattaaccta taaaaatagg cgtatcacga 2340
ggccctttcg tcttcaa 2357

<210> SEQ ID NO 85
<211> LENGTH: 300
<212> TYPE: DNA
<213> ORGANISM: Artificial Sequence
<220> FEATURE:
<223> OTHER INFORMATION: Nucleotide sequence of HN gene (1-569) of
KBNP-4152 and HN terminus (570-577) of Lasota stain

<400> SEQUENCE: 85
ccctttacta gttgagattc tcaaggatga tggggttagg gaggccaggg ctggccgctt 60
gagtcaattg cgagagggtt ggaaagatga cattgtatca cctatctttt gcgacgccaa 120
gaatcaaact gagtaccggc gtgagctcga gtcttacgct gccagctggc cataatcagc 180
tagcgctaat gtgattagat taaatcttgt cgatagtcac ttgattaaga aaaaatgtaa 240

```
gtggcaatga gatacaaggc aaaacagctc atggtaaata atacgggtag gacatggcga    300
```

<210> SEQ ID NO 86
<211> LENGTH: 33
<212> TYPE: DNA
<213> ORGANISM: Artificial Sequence
<220> FEATURE:
<223> OTHER INFORMATION: La-MR

<400> SEQUENCE: 86

```
ccgcggacgc gtgttttttc taacttgata gac                                  33
```

<210> SEQ ID NO 87
<211> LENGTH: 28
<212> TYPE: DNA
<213> ORGANISM: Artificial Sequence
<220> FEATURE:
<223> OTHER INFORMATION: ND-F1S

<400> SEQUENCE: 87

```
acgcgtacgg gtagaagagt ctggatcc                                        28
```

<210> SEQ ID NO 88
<211> LENGTH: 29
<212> TYPE: DNA
<213> ORGANISM: Artificial Sequence
<220> FEATURE:
<223> OTHER INFORMATION: ND-F1R

<400> SEQUENCE: 88

```
actagtgcgg ccgctgctgt tatctgtgc                                       29
```

<210> SEQ ID NO 89
<211> LENGTH: 27
<212> TYPE: DNA
<213> ORGANISM: Artificial Sequence
<220> FEATURE:
<223> OTHER INFORMATION: ND-F2F

<400> SEQUENCE: 89

```
gcggccgccc taatacaagc caaccag                                         27
```

<210> SEQ ID NO 90
<211> LENGTH: 29
<212> TYPE: DNA
<213> ORGANISM: Artificial Sequence
<220> FEATURE:
<223> OTHER INFORMATION: La-L1F

<400> SEQUENCE: 90

```
ttcgtacgga tccggcattc tggtttcac                                       29
```

<210> SEQ ID NO 91
<211> LENGTH: 32
<212> TYPE: DNA
<213> ORGANISM: Artificial Sequence
<220> FEATURE:
<223> OTHER INFORMATION: La-L1R

<400> SEQUENCE: 91

```
cctaggttat cgattcgatt agagataaac cc                                   32
```

<210> SEQ ID NO 92
<211> LENGTH: 32
<212> TYPE: DNA
<213> ORGANISM: Artificial Sequence
<220> FEATURE:

<223> OTHER INFORMATION: La-L2F

<400> SEQUENCE: 92
gagaatcgat atttccaatg acaacaacca gg 32

<210> SEQ ID NO 93
<211> LENGTH: 26
<212> TYPE: DNA
<213> ORGANISM: Artificial Sequence
<220> FEATURE:
<223> OTHER INFORMATION: La-L2R

<400> SEQUENCE: 93
cctaggacag ccttcaaata tttagg 26

<210> SEQ ID NO 94
<211> LENGTH: 40
<212> TYPE: DNA
<213> ORGANISM: Artificial Sequence
<220> FEATURE:
<223> OTHER INFORMATION: TM p1(linker)

<400> SEQUENCE: 94
gaattcttaa tacgactcac tataggacca agagacgggc 40

<210> SEQ ID NO 95
<211> LENGTH: 40
<212> TYPE: DNA
<213> ORGANISM: Artificial Sequence
<220> FEATURE:
<223> OTHER INFORMATION: TM p2(linker)

<400> SEQUENCE: 95
ccatatcgat tcgcgaccgc gggatactag tcgtacgcct 40

<210> SEQ ID NO 96
<211> LENGTH: 40
<212> TYPE: DNA
<213> ORGANISM: Artificial Sequence
<220> FEATURE:
<223> OTHER INFORMATION: TM p3(linker)

<400> SEQUENCE: 96
gcggtcgcga atcgatatgg gcccgtctct tggtcctata 40

<210> SEQ ID NO 97
<211> LENGTH: 44
<212> TYPE: DNA
<213> ORGANISM: Artificial Sequence
<220> FEATURE:
<223> OTHER INFORMATION: TM p4(linker)

<400> SEQUENCE: 97
catatgctct accaagagac ccctaggcgt acgactagta tccc 44

<210> SEQ ID NO 98
<211> LENGTH: 31
<212> TYPE: DNA
<213> ORGANISM: Artificial Sequence
<220> FEATURE:
<223> OTHER INFORMATION: HDV F

<400> SEQUENCE: 98
ggtctcttgg tgggtcggca tggcatctcc a 31

<210> SEQ ID NO 99

<211> LENGTH: 28
<212> TYPE: DNA
<213> ORGANISM: Artificial Sequence
<220> FEATURE:
<223> OTHER INFORMATION: HDV R

<400> SEQUENCE: 99
catatgcaaa aaacccctca agacccgt 28

<210> SEQ ID NO 100
<211> LENGTH: 43
<212> TYPE: DNA
<213> ORGANISM: Artificial Sequence
<220> FEATURE:
<223> OTHER INFORMATION: S41-P1

<400> SEQUENCE: 100
tacaatcctt ttaagaaata agctgcgtct ctgagattgc gct 43

<210> SEQ ID NO 101
<211> LENGTH: 48
<212> TYPE: DNA
<213> ORGANISM: Artificial Sequence
<220> FEATURE:
<223> OTHER INFORMATION: S41-P3

<400> SEQUENCE: 101
ccgcccactc acccagatca tcatgacaca aaaaactaat ctgtcttg 48

<210> SEQ ID NO 102
<211> LENGTH: 48
<212> TYPE: DNA
<213> ORGANISM: Artificial Sequence
<220> FEATURE:
<223> OTHER INFORMATION: S41-P5

<400> SEQUENCE: 102
attatttaca gttagtttac ctgtctatca agttagaaaa aacacggg 48

<210> SEQ ID NO 103
<211> LENGTH: 45
<212> TYPE: DNA
<213> ORGANISM: Artificial Sequence
<220> FEATURE:
<223> OTHER INFORMATION: S41-P7

<400> SEQUENCE: 103
agaagagtct ggatcccgac cggcacattc aggacgcaat atggg 45

<210> SEQ ID NO 104
<211> LENGTH: 49
<212> TYPE: DNA
<213> ORGANISM: Artificial Sequence
<220> FEATURE:
<223> OTHER INFORMATION: S41-P9

<400> SEQUENCE: 104
gataaagagg cgtgtgcaaa agccccatta gaggcatata acagaacac 49

<210> SEQ ID NO 105
<211> LENGTH: 49
<212> TYPE: DNA
<213> ORGANISM: Artificial Sequence
<220> FEATURE:
<223> OTHER INFORMATION: S41-P11

<400> SEQUENCE: 105

-continued tgactacttt gctaactcct cttggcgact ccatccgcaa gatccaagg 49

<210> SEQ ID NO 106
<211> LENGTH: 46
<212> TYPE: DNA
<213> ORGANISM: Artificial Sequence
<220> FEATURE:
<223> OTHER INFORMATION: S41-P13(1)

<400> SEQUENCE: 106
gtctgtgtcc acgtctggag gaaggagaca aaaacgcttt ataggt 46

<210> SEQ ID NO 107
<211> LENGTH: 46
<212> TYPE: DNA
<213> ORGANISM: Artificial Sequence
<220> FEATURE:
<223> OTHER INFORMATION: S41-P13(2)

<400> SEQUENCE: 107
gtctgtgtcc acgtctggag gaggcagaca agcacgcctg ataggt 46

<210> SEQ ID NO 108
<211> LENGTH: 46
<212> TYPE: DNA
<213> ORGANISM: Artificial Sequence
<220> FEATURE:
<223> OTHER INFORMATION: S41-P13(3)

<400> SEQUENCE: 108
gtctgtgtcc acgtctggag gaggcggcca agcacgcctg ataggt 46

<210> SEQ ID NO 109
<211> LENGTH: 45
<212> TYPE: DNA
<213> ORGANISM: Artificial Sequence
<220> FEATURE:
<223> OTHER INFORMATION: S41-P15

<400> SEQUENCE: 109
gctgttattg gcagtgtagc tcttggggtt gcaacagcgg cacag 45

<210> SEQ ID NO 110
<211> LENGTH: 45
<212> TYPE: DNA
<213> ORGANISM: Artificial Sequence
<220> FEATURE:
<223> OTHER INFORMATION: S41-P2

<400> SEQUENCE: 110
tcgacgcaga gactctaacg cgaggcgggt gagtgggtct agtag 45

<210> SEQ ID NO 111
<211> LENGTH: 48
<212> TYPE: DNA
<213> ORGANISM: Artificial Sequence
<220> FEATURE:
<223> OTHER INFORMATION: S41-P4

<400> SEQUENCE: 111
ctgtgttttt tgattagaca gaactaataa atgtcaatca aatggaca 48

<210> SEQ ID NO 112
<211> LENGTH: 47
<212> TYPE: DNA
<213> ORGANISM: Artificial Sequence
<220> FEATURE:

```
<223> OTHER INFORMATION: S41-P6

<400> SEQUENCE: 112

gatagttcaa tcttttttgt gcccatcttc tcagacctag ggctggc                          47

<210> SEQ ID NO 113
<211> LENGTH: 49
<212> TYPE: DNA
<213> ORGANISM: Artificial Sequence
<220> FEATURE:
<223> OTHER INFORMATION: S41-P8

<400> SEQUENCE: 113

cgtgtaagtc ctgcgttata cccgaggttt gaaagatggt cctaaggtc                       49

<210> SEQ ID NO 114
<211> LENGTH: 48
<212> TYPE: DNA
<213> ORGANISM: Artificial Sequence
<220> FEATURE:
<223> OTHER INFORMATION: S41-P10

<400> SEQUENCE: 114

gtaatctccg tatattgtct tgtgactgat gaaacgattg aggagaac                        48

<210> SEQ ID NO 115
<211> LENGTH: 45
<212> TYPE: DNA
<213> ORGANISM: Artificial Sequence
<220> FEATURE:
<223> OTHER INFORMATION: S41-P12

<400> SEQUENCE: 115

ctgaggtagg cgttctaggt tcccagacac aggtgcagac ctcct                           45

<210> SEQ ID NO 116
<211> LENGTH: 47
<212> TYPE: DNA
<213> ORGANISM: Artificial Sequence
<220> FEATURE:
<223> OTHER INFORMATION: S41-P14(1)

<400> SEQUENCE: 116

tcctctgttt ttgcgaaata tccacgacaa taaccgtcac atcgaga                         47

<210> SEQ ID NO 117
<211> LENGTH: 45
<212> TYPE: DNA
<213> ORGANISM: Artificial Sequence
<220> FEATURE:
<223> OTHER INFORMATION: S41-P14(2)

<400> SEQUENCE: 117

gtctgttcgt gcggactatc cacgacaata accgtcacat cgaga                           45

<210> SEQ ID NO 118
<211> LENGTH: 45
<212> TYPE: DNA
<213> ORGANISM: Artificial Sequence
<220> FEATURE:
<223> OTHER INFORMATION: S41-P14(3)

<400> SEQUENCE: 118

gccggttcgt gcggactatc cacgacaata accgtcacat cgaga                           45

<210> SEQ ID NO 119
```

-continued

```
<211> LENGTH: 49
<212> TYPE: DNA
<213> ORGANISM: Artificial Sequence
<220> FEATURE:
<223> OTHER INFORMATION: S41-P16

<400> SEQUENCE: 119

accccaacgt tgtcgccgtg tctattgtcg tcgccggcgg gattatgtt              49


<210> SEQ ID NO 120
<211> LENGTH: 39
<212> TYPE: DNA
<213> ORGANISM: Artificial Sequence
<220> FEATURE:
<221> NAME/KEY: CDS
<222> LOCATION: (1)..(39)
<223> OTHER INFORMATION: furin-like enzyme recognition site of the F
      protein of KBNP-C4152R2L

<400> SEQUENCE: 120

gga gga ggc aga caa gca cgc ctg ata ggt gct gtt att                39
Gly Gly Gly Arg Gln Ala Arg Leu Ile Gly Ala Val Ile
  1               5                  10


<210> SEQ ID NO 121
<211> LENGTH: 13
<212> TYPE: PRT
<213> ORGANISM: Artificial Sequence
<220> FEATURE:
<223> OTHER INFORMATION: furin-like enzyme recognition site of the F
      protein of KBNP-C4152R2L

<400> SEQUENCE: 121

Gly Gly Gly Arg Gln Ala Arg Leu Ile Gly Ala Val Ile
  1               5                  10


<210> SEQ ID NO 122
<211> LENGTH: 39
<212> TYPE: DNA
<213> ORGANISM: Artificial Sequence
<220> FEATURE:
<221> NAME/KEY: CDS
<222> LOCATION: (1)..(39)
<223> OTHER INFORMATION: furin-like enzyme recognition site of the F
      protein of KBNP-4152

<400> SEQUENCE: 122

gga gga agg aga caa aaa cgc ttt ata ggt gct gtt att                39
Gly Gly Arg Arg Gln Lys Arg Phe Ile Gly Ala Val Ile
  1               5                  10


<210> SEQ ID NO 123
<211> LENGTH: 13
<212> TYPE: PRT
<213> ORGANISM: Artificial Sequence
<220> FEATURE:
<223> OTHER INFORMATION: furin-like enzyme recognition site of the F
      protein of KBNP-4152

<400> SEQUENCE: 123

Gly Gly Arg Arg Gln Lys Arg Phe Ile Gly Ala Val Ile
  1               5                  10
```

ATTENUATED RECOMBINANT NEWCASTLE DISEASE VIRUS AND VACCINE CONTAINING THE SAME

CROSS-REFERENCE TO RELATED APPLICATION

This application claims priority to and the benefit of Korean Patent Application No. 10-2006-0093260 filed in the Korean Intellectual Property Office on Sep. 26, 2006, the entire content of which is incorporated herein by reference.

BACKGROUND OF THE INVENTION (a) Field of the Invention

The present invention relates to a recombinant vector for transcription of the Newcastle disease virus (NDV) genome, a strain of attenuated recombinant NDV with a surface antigen of pathogenic NDV prepared by the vector, a method of preparing a recombinant NDV having low pathogenicity and high protective efficiency against Newcastle disease (ND) using the vector, and a vaccine against ND containing the recombinant NDV.

(b) Description of the Related Art

Newcastle Disease (ND), which is known as one of the most important internationally known kinds of livestock disease, is an acute thermal respiratory disease, and is the first communicable disease by law in Korea. If an unimmunized fowl is infected, the mortality is 100%. Because the Newcastle disease virus (NDV) commonly exists in Korea, many difficulties are expected for eradicating the disease. Also, because various Newcastle disease viruses are widespread in Southeast Asia, China, and Taiwan, all of which actively trade with Korea, and because these viruses are potentially very dangerous factor, an urgent need to develop an Asia-type Newcastle disease vaccine exists.

The Newcastle disease virus (NDV) is a single-stranded RNA virus belonging to the *Avulavirus* genus. The envelope of the Newcastle disease virus includes the Haemagglutinin-Neuraminidase (HN) protein which makes the virus bind to a host, and the Fusion (F) protein which makes the envelope fuse with the host cell. F and HN proteins are glycoproteins and are distributed on the surface of the viral envelope.

The F protein belongs to the type I membrane glycoprotein group and forms a trimeric structure (trimer). The F protein is made as a non-active precursor form (F0), and is divided into the disulfide linked subunits F1 and F2 when the precursor F0 molecule passes through Golgi membranes. This process exposes a hydrophobic domain at the amino terminus of the F1 subunit, wherein the domain performs important role in the biological activity of mature protein. The hydrophobic domain, called a fusion peptide, is well conserved in the F protein of paramyxovirus, and is directly involved in membrane fusion. The F protein of paramyxovirus includes common structure characteristics such as heptad repeats, and two regions being capable of forming an alpha helix structure. The longest heptad repeat A of the repeats is adjacent to the N-terminal hydrophobic fusion peptide of F1, and heptad repeat B is close to the upper part of transmembrane region. Heptad repeat B consists of a series of well-conserved Leucine or Isoleusine at every 7 residues.

HN protein belongs to the type II membrane glycoprotein and forms a tetramer on the surface of the viral envelope, to penetrate into a cell membrane (Gorman et al., 1988; Ng et al., 1989). The HN protein causes virion to locate on the host cell surface via binding to sialic acids of glycoconjugates. The HN protein is divided into the three regions of a transmembrane domain, a stalk domain and a globular domain. Both a binding site of an antigenic receptor and an active site of neuraminidase locate on the globular domain. An active site of fusion induction locates on the stalk domain, and interacts with the F protein (Sergei et al., 1993). The expected structure of the stalk domain is an alpha-helix structure, with two heptad repeats including the heptad repeat A (at the $74^{th}$-$88^{th}$ positions) and the heptad repeat B (at the $96^{th}$-$110^{th}$ position). Also, it has been reported that any mutation breaking the structure reduces the receptor binding and the neuraminidase activity. Moreover, it has been reported that a mutation capable of destroying a structure causes decrease of the receptor binding and neuraminidase activities.

According to the level of disease in chicken, NDV is classified with the following pathogenic types (pathotypes): 1) viscerotropic velogenic (high-pathogenic) NDV showing digestive organ lesions and high mortality; and neurotropic velogenic NDV mainly showing respiratory and neurological symptom, and high mortality; 2) mesogenic NDV showing low mortality, but acute respiratory and neurological symptoms in some of the poultry; 3) lentogenic (low-pathogenic) and apathogenic NDV causing slight illness or asymptomatic respiratory infection.

In order for the NDV to infect a cell, it is necessary for the precursor glycoprotein F0 to be cleaved into F1 and F2. This post-translational cleavage is intervened by proteases of a host cell. If the cleavage does not occur, non-infectious virions are generated, and the virus replication cannot progress. The F0 protein of a virulent virus can be cleaved by various proteases, but the F0 protein of a low toxicity virus is restricted in terms of susceptibilities, and particularly the low toxicity virus is only capable of growing in a specific host cell type.

Whereas the lentogenic virus is only reproduced in a region that has trypsin-like enzymes, including respiratory organs or intestinal tract, because the virulent viruses are reproduced in various regions including tissues and organs, and therefore the virulent viruses cause a fetal systemic infection.

By the amino acid inspection of the Fo precursor, it is identified that the lentogenic viruses have a single arginine (R) connecting F2 and F1 subunit, whereas strains with toxicity of more than the mesogenic have additional basic amino acids forming two pairs such as K/R-X-K/R-R-F on the cleavage region. Moreover, the F2 chain of the strains with pathogenicity of more than the mesogenic is generally is disclosed by Phenylalanine residue, whereas the F2 chain of the strains with pathogenicity of less than the lentogenic is generally disclosed by Leucine.

In the U.S., a killed vaccine has been used for the identification of the Newcastle disease (Hofstad, 1953). By observation that a part of the enzootic disease virus only generates mild disease, for the first time, the mesogenic live vaccine Roakin was developed, and subsequently, milder Hitchner B1 and LaSota (Goldhaft, 1980) was developed.

One of the main advantages of live vaccines is the capability of administering by using a mass application method of a low-cost. A conventional application method is to administer the vaccine through drinking water.

The mass application of a live vaccine through spray and aerosols is very useful, because many birds can be more quickly administered with the vaccine and thereby vaccinated. It is important to control nozzles wherein particles are generated, to achieve an exacting particle size.

Recently used live vaccines have some problems. Because these vaccines still have a little pathogenicity, occasionally side effects of the vaccine can occur. Moreover, because antibodies inherited from the maternal line neutralize live vaccine viruses, successful immunity formation can be interfered with. Therefore, it is important to use an exceedingly mild virus, to perform the first vaccination, and a vaccine that is able to overcome the maternal antibody is required.

A killed vaccine is usually produced from infectious allantoic fluid mixed with appropriate supplements, and it is treated with formalin or beta-propiolactone, to kill the virus. The vaccine is administered to muscles or through subcutaneous injection, but it has a disadvantage due to a high-cost for its production and application.

Recently, the antigenicity of velogenic NDV generated both domestically and in foreign countries has been presumed to show many differences compared with the vaccine strain. For this reason, it can be concluded that the discovery of an outdoor strain with many differences with a genotype of the vaccine strain may occur, and if the vaccine antibody titer is not high enough, it is able to prevent mortality, but it is unable to prevent from decreasing in egg-laying rate, etc.

Depending on a phylogenic analysis based on the partial sequence of the F gene, the genotype of NDV is classified as genotype I to genotype IX. Molecular epidemiologically, most Newcastle disease viruses distributed in Korea belong to genotype VI and genotype VII. In the case of genotype VI, even though a variant strain may occur because of intensive vaccination, relatively lowly isolated than the genotype VII, and primarily only the genotype VII has been isolated after 2000, the possibility of its extermination is considered. Consequently, sequencing analysis, a determination of recent NDV gene sequences through genome project, and a molecular epidemiological research through gene comparison with world-wide NDV that is registered in the GenBank are very important for developing an optimal vaccine strain.

At present, conventionally used killed oil vaccine of Newcastle disease (ND) is produced by using lentogenic NDV such as Clone 30 or a LaSota strain, and the production of a killed vaccine using velogenic NDV is prohibited because of safety problems. Therefore, the necessity for technology for producing an ND vaccine that is safer, more economical, and in which the antigen is similar to the field strain is increased, and the development of a vaccine using reverse genetics technology is mostly closed technology to this demand.

The reverse genetics technology of a negative strand RNA virus is proposed as a technology for a rescue of infectious virus from the virus genome (U.S. Pat. No. 5,166,057). Even though this technology was originally proposed to manipulate the influenza virus genome, it can be successfully applied to various segment and non-segment negative strand RNA viruses, including Rabies virus, Respiratory Syncytial virus, and Sendai virus.

The present inventors developed a novel vaccine strain using the reverse genetics technology as described above, and as a result; the technology of producing safe ND vaccine strain with antigenicity similar to that of the field strain is developed.

SUMMARY OF THE INVENTION

An object of the present invention is to provide a recombinant vector for transcription of the NDV genome.

Another object of the present invention is to provide a strain of attenuated recombinant NDV with a surface antigen of pathogenic NDV.

Another object of the present invention is to provide a method of preparing a recombinant NDV having low pathogenicity and high protective efficiency against Newcastle disease (ND) using the vector.

Another object of the present invention is to provide a method of attenuating NDV to be able to increase immunogenicity and decrease pathogenicity of NDV using reverse genetics technology.

Still another object of the present invention is to provide a vaccine against ND containing the recombinant NDV.

BRIEF DESCRIPTION OF THE DRAWINGS

FIG. 4 shows a linker sequence used for manufacturing the parental vector, pTMH that is used for cloning the genomic DNA of NDV and a primer sequence used for manufacturing the linker.

FIG. 7 shows the whole nucleotide sequence of the pTMH vector.

FIGS. 10A and 10B show a process of cloning the genomic DNA of NDV into a pBR322 vector.

FIG. 13 shows a nucleotide sequence of the furin-like enzyme recognition site of the F protein and the linker of M and F genes of the recombinant virus.

FIG. 14 shows a synthesis process of a gene wherein a mutation is caused in the furin-like enzyme recognition site of the F protein using PTDS and site-directed mutagenesis.

FIG. 15 shows a design drawing of PTDS primer for connecting HN (1-566) gene of KBNP-4152 with HN terminus (567-577) gene of La Sota strain.

DETAILED DESCRIPTION OF THE PREFERRED EMBODIMENTS

The present invention relates to a recombinant vector for transcription of a Newcastle disease virus (NDV) genome, a strain of attenuated recombinant NDV with a surface antigen of pathogenic Newcastle disease virus prepared by the vector, a method of preparing a recombinant NDV having low pathogenicity and high preventive efficiency against Newcastle disease (ND) using the vector, and a vaccine against Newcastle disease containing the recombinant Newcastle disease virus.

Figure 24:
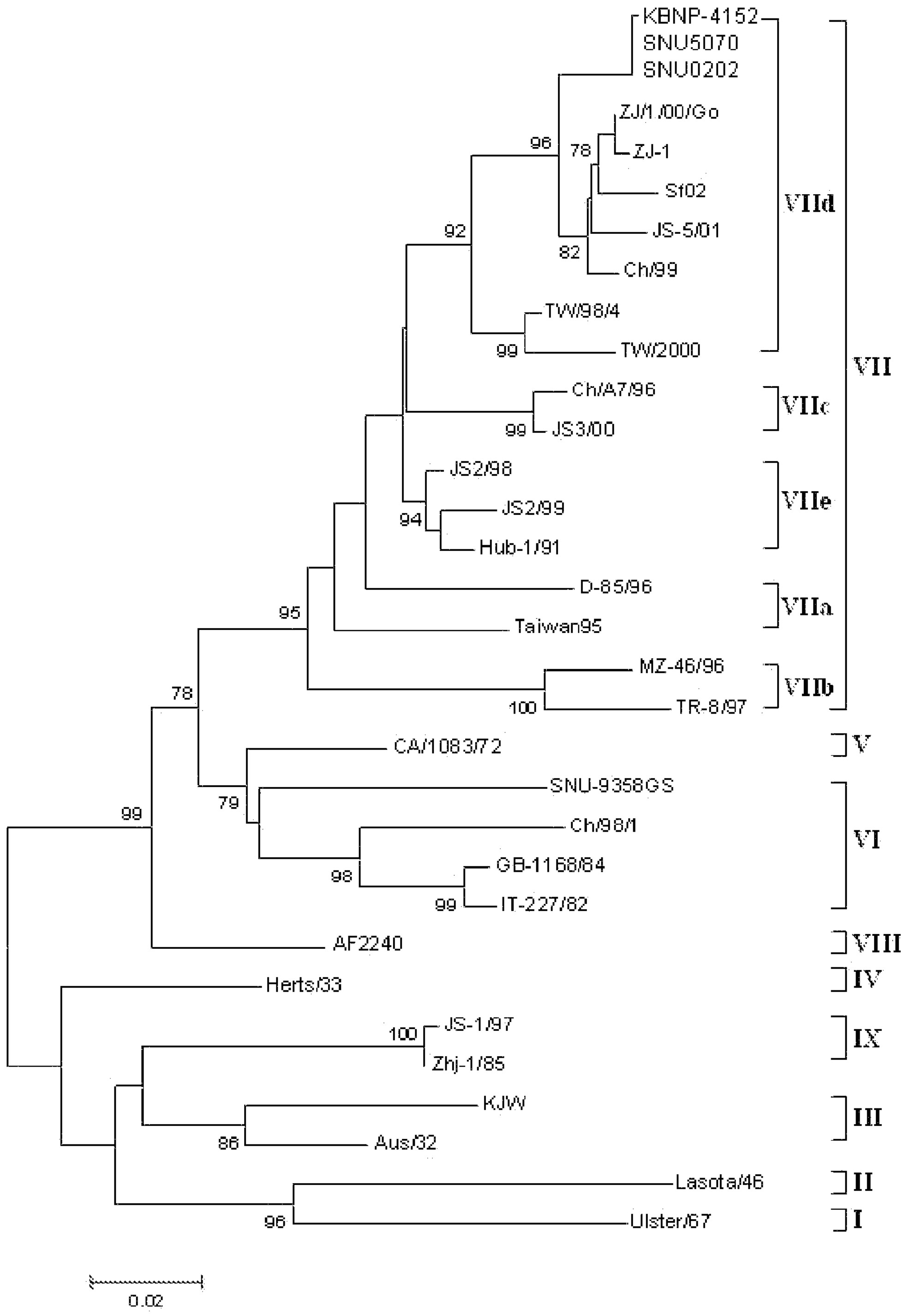
FIG. 24 shows an F gene of the present invention and a phylogenic analysis result of Newcastle virus using neighbor-joining method.

An F gene (384 bp; positioned at the $1^{st}$ to $384^{th}$ nucleotides in the F gene) of the present invention and a phylogenic analysis result of Newcastle virus using neighbor-joining method is shown in FIG. 24.

Strains shown in FIG. 24 are only examples, and currently numerous kinds of Newcastle disease virus strains are classified with genotype I to IX. Further, it has been much reported that the Newcastle virus is classified by molecular epidemiological analysis. Therefore, the classification of strains each genotype as described in FIG. 24 can be readily recognized by persons skilled in the art of the technical field to which this invention belongs. In this specification, the standard of the strain classification thereof quote a content written in reference as follows, the entire content of which is incorporated herein by reference:

1. Kwon H. J. PhD Thesis. Seoul National University, 2000.
2. Lomniczi B., Wehmann E., Herczeg J., Ballagi-Pord Ȣny A., Kaleta E. F., Werner O., Meulemans G., Jorgensen P. H., Mante A. P., Gielkens A. L. J., Capua I., and Damoser J., Arch Virol 143, 49-64, 1998.
3. Herczeg J., Wehmann E., Bragg R. R., Travassos Dias P. M., Hadjiev G., Werner O., and Lomniczi, B. Arch Virol 144, 2087-2099, 1999.
4. Yang C. Y., Shieh H. K., Lin Y. L., Chang P. C., Avian Dis 43, 125-130, 1999.
5. Kwon H. J., Cho S. H., Ahn Y. J., Seo S. H., Choi K. S., and Kim S. J. Vet Microbiol 95, 39-48, 2003.
6. Liu X. F., Wan H. Q., Ni X. X., Wu Y. T., and Liu W. B. (2003). Pathotypical and genotypical characterization of strains of Newcastle disease virus isolated from outbreaks in chicken and goose flocks in some regions of China during 1985-2001. Arch Virol, 148, 1387-1403.
7. Tsai H. J., Chang K. H., Tseng C. H., Frost K. M., Manvell R. J., and Alexander D. J. Vet Microbiol, 104, 19-30, 2004.

At present, La Sota/46 used as vaccine strain is genotype II, whereas most of strains identified as field strains belong to genotypes VI to VII, which are genetically distant from the vaccine strain La Sota/46. For example, in the HN protein of NDV, the 345-PDEQDYQIR-353 site on the HN protein has been known as an important linear epitope forming a neutralizing antibody. As domestic pathogenic NDV, genotype VI (95-98, 99-70, 99-71) of the virus and genotype VII of the virus have coexisted, and particularly, the genotype VI of NDV was isolated in 1999, but was not isolated from 2000 to 2006 at all. For the first time, genotype VIIa of NDV was isolated from fowls in 1995, and thereafter the virus was not isolated, and only genotype VIId of NDV isolated. In the case of genotype VI of virus, the first variant strain of linear epitope (E347K) was observed in strains (SNU9358GG, SNU9444) isolated in 1993 and 1994, and continuously observed in the 95-98, 99-70, and 99-71. Therefore, it is considered that these variant strains could avoid immunity and survive a long time, and is considered that the variant strains nearly are replaced with emerging genotype VII in Korea since 2000. In the case of genotype VII of the virus, all viruses isolated from 1995 to 2001 are similar to the linear epitope of the La Sota strain. However, variant strain of the linear epitope (E347K) was firstly observed in 2002, and predominantly NDV having additional mutation was observed in 2005 (refer to below Table).

| Year | Classical epitope 346DEQDYQIRM354 | Variant epitope 346-K ------ M/K-354 |
|---|---|---|
| 1995 | 1 | — |
| 2000 | 16 | — |
| 2001 | 1 | — |
| 2002 | 15 (79%) | 4 (10.5%) |
| 2003 | 1 | 1 |
| 2004 | — | 1 |
| 2005 | 1 (6.25%) | 15 (93.75%) |
| 2006 | — | 2 |

Considering this point, because the previous vaccine strain, La Sota/46 cannot used for effective prevention against antigenically different Newcastle disease virus emerging in current, therefore, it is very significant that the present invention provides the technology for developing a vaccine strain having almost similar antigenicity against field strain.

As used herein, the term "high-pathogenic (velogenic) Newcastle disease virus" includes pathogenic Newcastle disease viruses having pathogenicity equal to or higher than that of the mesogenic strain as well as conventionally classified high-pathogenic Newcastle disease viruses, unless it is differently defined. In the present invention, the high-pathogenic Newcastle disease virus shows its pathogenicity by producing infectious viruses in all cells of the body when infected into an animal. When the case of an amino acid sequence at the $113^{th}$ to $116^{th}$ positions of the F protein is represented by following Formula 1, the F protein is cleaved by furin or furin-like protease (hereinafter referred to as 'furin') existing in almost all cells in the body, thereby being converted into an active structure, and obtaining infectious ability. Therefore, a pathogenic Newcastle disease virus is defined as one having nucleotide sequence encoding an amino acid sequence represented by following Formula 1 at the $113^{th}$ to $116^{th}$ positions of the F protein:

$$113\text{-}X_1X_2X_3X_4\text{-}116 \qquad \text{Formula 1}$$

wherein $X_1$, $X_3$ and $X_4$ are independently arginine (R) or lysine (K), and $X_2$ is selected from the group consisting of alanine, isoleucine, leucine, methionine, phenylalanine, proline, tryptophan, valine, asparagine, cysteine, glutamine, glycine, serine, theronine, tyrosine, aspartic acid, glutamic acid, arginine, histidine, and lysine.

In this case, when an amino acid at the $112^{th}$ position of the F protein is a basic amino acid such as arginine or lysine, the pathogenic Newcastle disease virus has higher pathogenicity.

Also, as used herein, the term "low-pathogenic (lentogenic) Newcastle disease virus" includes apathogenic Newcastle disease viruses having no pathogenicity as well as conventionally classified lentogenic Newcastle disease viruses, unless differently defined. In the present invention, the low-pathogenic Newcastle disease virus having nucleotide sequence encoding an amino acid sequence represented by following Formula 2 at the $113^{th}$ to $116^{th}$ positions of the F protein, and when infected into animals, the virus is activated only by some specific extracellular protease in digestive organs and respiratory organs, thereby being merely locally infected to show low pathogenicity. Therefore, the low-pathogenic Newcastle disease virus is defined as having nucleotide sequence encoding an amino acid sequence represented by following Formula 2 at the $113^{th}$ to $116^{th}$ positions of the F protein:

$113\text{-}X_4X_5X_7X_8\text{-}116$ Formula 2 wherein $X_5$, $X_6$ and $X_7$ are independently selected from the group consisting of alanine, isoleucine, leucine, methionine, phenylalanine, proline, tryptophan, valine, asparagine, cysteine, glutamine, glycine, serine, theronine, tyrosine, aspartic acid, glutamic acid, arginine, histidine and lysine, and $X_5$ and $X_7$ are not both arginine (R) or lysine (K) at the same time, and $X_8$ is arginine (R) or lysine (K).

The Newcastle disease virus obtains pathogenicity when a cleavage site positioned in F protein of the virus is cleaved by furin and a fusion region where the F protein is fused with a cellular membrane is exposed. furin is an enzyme distributed in the whole body of an animal, and thus, the activation of the infectious ability of the virus by furin can be generated in the whole body of animal, whereby the virus has pathogenicity. Therefore, the level of pathogenicity of the Newcastle disease virus may depend on the extent of recognition and cleavage by furin at the cleaved site in F protein.

When the furin recognition site (amino acids at $113^{th}$ to $116^{th}$ positions) of F protein of the Newcastle disease virus has at least three basic amino acids (113-R-X-K/R-R-116) as shown in Formula 1, the virus can be systemically infected, and obtain pathogenicity. However, as shown in Formula 2, if one or more basic amino acids are replaced with a non-basic amino acid, the cleavage and recognition are conducted by not furin but locally existing extracellular protease, and mortal systemic infection of the virus does not occur, thereby showing low pathogenicity.

The present invention relates to a technique to prepare a genetically stable and attenuated recombinant Newcastle disease virus based on a low-pathogenic Newcastle disease virus, by substituting coding regions for the F protein and HN protein with those of high-pathogenic viruses prevailing domestically and in Asia, to enhance the protective effect of the virus against the high-pathogenic viruses, and by substituting a codon encoding the $115^{th}$ amino acid of a high-pathogenic Newcastle disease virus with a codon for a non-basic amino acid, wherein the codon for a non-basic amino acid can be converted into a codon for a basic amino acid when at least two point mutations occur. As described above, the recombinant Newcastle disease virus according to the present invention has an identical or similar surface antigen with field strains thereby showing high antigenicity against the field strains and being effectively attenuated. In addition, the recombinant Newcastle disease virus according to the present invention cannot be converted into a high-pathogenic strain until at least two point mutations occur at the codon for the $115^{th}$ amino acid of the F protein, thereby showing excellent stability and safety.

Pathogenic Newcastle disease viruses can be classified into a syncytial type forming syncytia and a granular type forming granules depending on their cytopathic effects, and it is generally known that the syncytial type is more highly pathogenic than the granular type. The present invention may be characterized by remarkably decreasing the pathogenicity by using the granular type virus clone as a high-velogenic Newcastle disease virus for providing the region encoding the F and HN proteins. In addition, in an HN protein of the Newcastle disease virus, the HN protein of a high-pathogenic Newcastle disease virus has 571 amino acids, which is a relatively short length, whereas the HN protein of a low-pathogenic Newcastle disease virus has 577 or 616 amino acids, which is longer than that of the high-pathogenic virus, and thus the high-pathogenic and the low-pathogenic strains may be classified by a C-terminal amino acid sequence of HN. Therefore, in the present invention, the C-terminus of HN protein is modified identically with that of a low-pathogenic strain (577 amino acids), thereby preparing a more attenuated recombinant Newcastle disease virus.

As used herein, the nucleotide sequences encoding P, M, F, HN and L proteins contained in a vector for transcription of the Newcastle disease virus genome and a recombinant Newcastle disease virus should be understood to include all non-coding nucleotide sequences existing in P, M, F, HN and L genes as long as they have no affectations on the expressed proteins, as well as the nucleotide sequences directly encoding the proteins.

In more detail, the present invention relates to a vector for transcription of the Newcastle disease virus genome, including a gene fragment consisting of nucleotide sequences encoding NP, P, M, F, HN, and L proteins of the Newcastle disease virus; and a promoter and a terminator, that are operably linked to the gene fragment, wherein the NP, P, M, and L genes are derived from the genome of a low-pathogenic Newcastle disease virus, the La Sota strain, and the F and HN genes are derived from the genome of a high-pathogenic Newcastle disease virus, KBNP-4152, wherein the F protein coding sequence contained in the vector is characterized in that the codon encoding basic amino acid at the $115^{th}$ position of the F protein of the velogenic Newcastle disease virus including KBNP-4152 is substituted with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU.

The HN gene of the vector may be additionally mutated so that the codons for the $1^{st}$ to $569^{th}$ amino acids of HN protein encodes those of a high-pathogenic Newcastle disease virus and the codons for the amino acids after $570^{th}$ position encode those of a low-pathogenic Newcastle disease virus including the La Sota strain.

In addition, the promoter and terminator may be used without particular limits, as long as they can be operably linked to the Newcastle disease virus genome in the plasmid. Such promoters and terminators may be readily selected and used by persons skilled in the art of the technical field to which this invention belongs. In an embodiment of the present invention, the promoter and terminator may be a T7 promoter and a T7 terminator, respectively.

Figure 23:
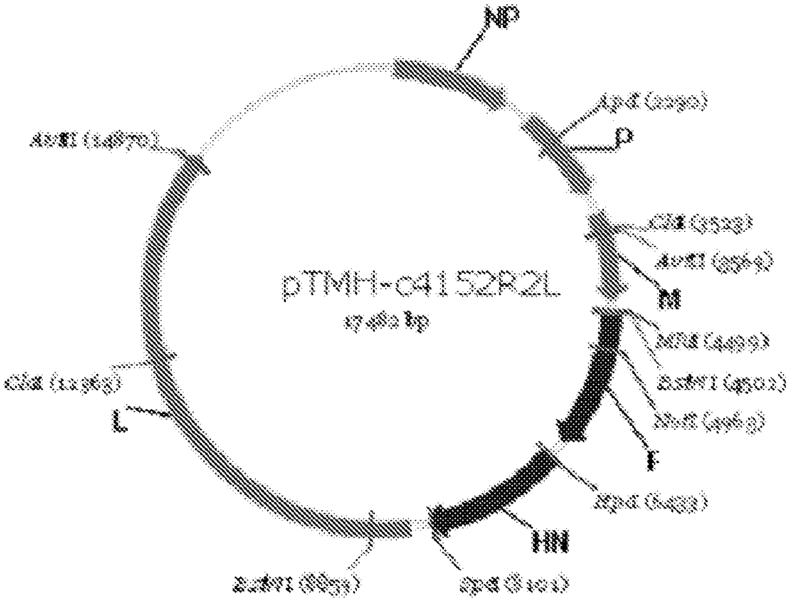
FIG. 23 shows a map of the KBNP-C4251R2L genome cloned into a pTMH vector and a nucleotide sequence of the genome.

In the preferred embodiment of the present invention, the vector for transcription of the virus genome may include nucleotide sequences encoding amino acid sequences of SEQ ID NO: 2 to 7 or nucleotide sequence of following SEQ ID NO: 1 (refer to FIG. 23, hereinafter, called pTNH-c4152R2L).

```
                                                               Gene-
   start
   1 accaaacagagaatccgtgagttacgataaaaggcgaaggagcaattgaagtcgcacggg

  61 tagaaggtgtgaatctcgagtgcgagcccgaagcacaaactcgagaaagccttctgccaa
       M  S  S  V  F  D  E  Y  E  Q  L  L  A  A  Q  T  R  P  N  G•

 121 cATGTCTTCCGTATTTGATGAGTACGAACAGCTCCTCGCGGCTCAGACTCGCCCCAATGG
      •A  H  G  G  G  E  K  G  S  T  L  K  V  D  V  P  V  F  T  L•

 181 AGCTCATGGAGGGGGAGAAAAAGGGAGTACCTTAAAAGTAGACGTCCCGGTATTCACTCT
      •N  S  D  D  P  E  D  R  W  S  F  V  V  F  C  L  R  I  A  V•

 241 TAACAGTGATGACCCAGAAGATAGATGGAGCTTTGTGGTATTCTGCCTCCGGATTGCTGT
      •S  E  D  A  N  K  P  L  R  Q  G  A  L  I  S  L  L  C  S  H•

 301 TAGCGAAGATGCCAACAAACCACTCAGGCAAGGTGCTCTCATATCTCTTTTATGCTCCCA
      •S  Q  V  M  R  N  H  V  A  I  A  G  K  Q  N  E  A  T  L  A•

 361 CTCACAGGTAATGAGGAACCATGTTGCCATTGCAGGGAAACAGAATGAAGCCACATTGGC
      •V  L  E  I  D  G  F  A  N  G  T  P  Q  F  N  N  R  S  G  V•

 421 CGTGCTTGAGATTGATGGCTTTGCCAACGGCACGCCCCAGTTCAACAATAGGAGTGGAGT
      •S  E  E  R  A  Q  R  F  A  M  I  A  G  S  L  P  R  A  C  S•

 481 GTCTGAAGAGAGAGCACAGAGATTTGCGATGATAGCAGGATCTCTCCCTCGGGCATGCAG
      •N  G  T  P  F  V  T  A  G  A  E  D  D  A  P  E  D  I  T  D•

 541 CAACGGAACCCCGTTCGTCACAGCCGGGGCAGAAGATGATGCACCAGAAGACATCACCGA
      •T  L  E  R  I  L  S  I  Q  A  Q  V  W  V  T  V  A  K  A  M•

 601 TACCCTGGAGAGGATCCTCTCTATCCAGGCTCAAGTATGGGTCACAGTAGCAAAAGCCAT
      •T  A  Y  E  T  A  D  E  S  E  T  R  R  I  N  K  Y  M  Q  Q•

 661 GACTGCGTATGAGACTGCAGATGAGTCGGAAACAAGGCGAATCAATAAGTATATGCAGCA
      •G  R  V  Q  K  K  Y  I  L  Y  P  V  C  R  S  T  I  Q  L  T•

 721 AGGCAGGGTCCAAAAGAAATACATCCTCTACCCCGTATGCAGGAGCACAATCCAACTCAC
      •I  R  Q  S  L  A  V  R  I  F  L  V  S  E  L  K  R  G  R  N•

 781 GATCAGACAGTCTCTTGCAGTCCGCATCTTTTTGGTTAGCGAGCTCAAGAGAGGCCGCAA
      •T  A  G  G  T  S  T  Y  Y  N  L  V  G  D  V  D  S  Y  I  R•

 841 CACGGCAGGTGGTACCTCTACTTATTATAACCTGGTAGGGGACGTAGACTCATACATCAG
      •N  T  G  L  T  A  F  F  L  T  L  K  Y  G  I  N  T  K  T  S•

 901 GAATACCGGGCTTACTGCATTCTTCTTGACACTCAAGTACGGAATCAACACCAAGACATC
      •A  L  A  L  S  S  L  S  G  D  I  Q  K  M  K  Q  L  M  R  L•

 961 AGCCCTTGCACTTAGTAGCCTCTCAGGCGACATCCAGAAGATGAAGCAGCTCATGCGTTT
      •Y  R  M  K  G  D  N  A  P  Y  M  T  L  L  G  D  S  D  Q  M•

1021 GTATCGGATGAAAGGAGATAATGCGCCGTACATGACATTACTTGGTGATAGTGACCAGAT
      •S  F  A  P  A  E  Y  A  Q  L  Y  S  F  A  M  G  M  A  S  V•

1081 GAGCTTTGCGCCTGCCGAGTATGCACAACTTTACTCCTTTGCCATGGGTATGGCATCAGT
      •L  D  K  G  T  G  K  Y  Q  F  A  R  D  F  M  S  T  S  F  W•

1141 CCTAGATAAAGGTACTGGGAAATACCAATTTGCCAGGGACTTTATGAGCACATCATTCTG
      •R  L  G  V  E  Y  A  Q  A  Q  G  S  S  I  N  E  D  M  A  A•

1201 GAGACTTGGAGTAGAGTACGCTCAGGCTCAGGGAAGTAGCATTAACGAGGATATGGCTGC
      •E  L  K  L  T  P  A  A  M  K  G  L  A  A  A  A  Q  R  V  S•

1261 CGAGCTAAAGCTAACCCCAGCAGCAATGAAGGGCCTGGCAGCTGCTGCCCAACGGGTCTC
      •D  D  T  S  S  I  Y  M  P  T  Q  Q  V  G  V  L  T  G  L  S•

1321 CGACGATACCAGCAGCATATACATGCCTACTCAACAAGTCGGAGTCCTCACTGGGCTTAG
      •E  G  G  S  Q  A  L  Q  G  G  S  N  R  S  Q  G  Q  P  E  A•

1381 CGAGGGGGGGTCCCAAGCTCTACAAGGCGGATCGAATAGATCGCAAGGGCAACCAGAAGC
      •G  D  G  E  T  Q  F  L  D  L  M  R  A  V  A  N  S  M  R  E•

1441 CGGGGATGGGGAGACCCAATTCCTGGATCTGATGAGAGCGGTAGCAAATAGCATGAGGGA
      •A  P  N  S  A  Q  G  T  P  Q  S  G  P  P  P  T  P  G  P  S•
```

-continued

```
1501 GGCGCCAAACTCTGCACAGGGCACTCCCCAATCGGGGCCTCCCCCAACTCCTGGGCCATC
     •Q  D  N  D  T  D  W  G  Y

1561 CCAAGATAACGACACCGACTGGGGGTATTGAtggacaaaacccagcctgcttccacaaaa

1621 acatcccaatgccctcacccgtagtcgacccctcgatttgcggctctatatgaccacacc

1681 ctcaaacaaacatccccctctttcctccctcccccctgctgtacaactccgcacgccctag
                                                         gene End

1741 ataccacaggcacaatgcggctcactaacaatcaaaacagagccgagggaattagaaaaa
       gene start

1801 agtacgggtagaagagggatattcagagatcagggcaagtctcccgagtctctgctctct
                                        M  A  T  F  T  D  A  E  I  D  E  L

1861 cctctacctgatagaccaggacaaacATGGCCACCTTTACAGATGCAGAGATCGACGAGC
      • F  E  T  S  G  T  V  I  D  N  I  I  T  A  Q  G  K  P  A  E•

1921 TATTTGAGACAAGTGGAACTGTCATTGACAACATAATTACAGCCCAGGGTAAACCAGCAG
      • T  V  G  R  S  A  I  P  Q  G  K  T  K  V  L  S  A  A  W  E•

1981 AGACTGTTGGAAGGAGTGCAATCCCACAAGGCAAGACCAAGGTGCTGAGCGCAGCATGGG
      • K  H  G  S  I  Q  P  P  A  S  Q  D  N  P  D  R  Q  D  R  S•

2041 AGAAGCATGGGAGCATCCAGCCACCGGCCAGTCAAGACAACCCCGATCGACAGGACAGAT
      • D  K  Q  P  S  T  P  E  Q  T  T  P  H  D  S  P  P  A  T  S•

2101 CTGACAAACAACCATCCACACCCGAGCAAACGACCCCGCATGACAGCCCGCCGGCCACAT
      • A  D  Q  P  P  T  Q  A  T  D  E  A  V  D  T  Q  F  R  T  G•

2161 CCGCCGACCAGCCCCCCACCCAGGCCACAGACGAAGCCGTCGACACACAGTTCAGGACCG
      • A  S  N  S  L  L  L  M  L  D  K  L  S  N  K  S  S  N  A  K•

2221 GAGCAAGCAACTCTCTGCTGTTGATGCTTGACAAGCTCAGCAATAAATCGTCCAATGCTA
        ApaI
      • K  G  P  W  S  S  P  Q  E  G  N  H  Q  R  P  T  Q  Q  Q  G•

2281 AAAAGGGCCCATGGTCGAGCCCCCAAGAGGGGAATCACCAACGTCCGACTCAACAGCAGG
      • S  Q  P  S  R  G  N  S  Q  E  R  P  Q  N  Q  V  K  A  A  P•

2341 GGAGTCAACCCAGTCGCGGAAACAGTCAGGAAAGACCGCAGAACCAAGTCAAGGCCGCCC
      • G  N  Q  G  T  D  V  N  T  A  Y  H  G  Q  W  E  E  S  Q  L•

2401 CTGGAAACCAGGGCACAGACGTGAACACAGCATATCATGGACAATGGGAGGAGTCACAAC
      • S  A  G  A  T  P  H  A  L  R  S  R  Q  S  Q  D  N  T  L  V•

2461 TATCAGCTGGTGCAACCCCTCATGCTCTCCGATCAAGGCAGAGCCAAGACAATACCCTTG
      • S  A  D  H  V  Q  P  P  V  D  F  V  Q  A  M  M  S  M  M  E•

2521 TATCTGCGGATCATGTCCAGCCGCCTGTAGACTTTGTGCAAGCGATGATGTCTATGATGG
      • A  I  S  Q  R  V  S  K  V  D  Y  Q  L  D  L  V  L  K  Q  T•

2581 AGGCGATATCACAGAGAGTAAGTAAGGTTGACTATCAGCTAGATCTTGTCTTGAAACAGA
      • S  S  I  P  M  M  R  S  E  I  Q  Q  L  K  T  S  V  A  V  M•

2641 CATCCTCCATCCCTATGATGCGGTCCGAAATCCAACAGCTGAAAACATCTGTTGCAGTCA
      • E  A  N  L  G  M  M  K  I  L  D  P  G  C  A  N  I  S  S  L•

2701 TGGAAGCCAACTTGGGAATGATGAAGATTCTGGATCCCGGTTGTGCCAACATTTCATCTC
      • S  D  L  R  A  V  A  R  S  H  P  V  L  V  S  G  P  G  D  P•

2761 TGAGTGATCTACGGGCAGTTGCCCGATCTCACCCGGTTTTAGTTTCAGGCCCTGGAGACC
      • S  P  Y  V  T  Q  G  G  E  M  A  L  N  K  L  S  Q  P  V  P•

2821 CCTCTCCCTATGTGACACAAGGAGGCGAAATGGCACTTAATAAACTTTCGCAACCAGTGC
      • H  P  S  E  L  I  K  P  A  T  A  C  G  P  D  I  G  V  E  K•

2881 CACATCCATCTGAATTGATTAAACCCGCCACTGCATGCGGGCCTGATATAGGAGTGGAAA
      • D  T  V  R  A  L  I  M  S  R  P  M  H  P  S  S  S  A  K  L•

2941 AGGACACTGTCCGTGCATTGATCATGTCACGCCCAATGCACCCGAGTTCTTCAGCCAAGC
      • L  S  K  L  D  A  A  G  S  I  E  E  I  R  K  I  K  R  L  A•

3001 TCCTAAGCAAGTTAGATGCAGCCGGGTCGATCGAGGAAATCAGGAAAATCAAGCGCCTTG
      • L  N  G

3061 CTCTAAATGGCTAAttactactgccacacgtagcgggtccctgtccactcggcatcacac

3121 ggaatctgcaccgagttcccccccgcagacccaaggtccaactctccaagcggcaatcct
```

-continued

```
3181 ctctcgcttcctcagccccactgaatgatcgcgtaaccgtaattaatctagctacattta
         Gene End    Gene start                             M  D  S  S•

3241 agattaagaaaaaatacgggtagaattggagtgccccaattgtgccaagATGGACTCATC
      •R  T  I  G  L  Y  F  D  S  A  H  S  S  S  N  L  L  A  F  P•

3301 TAGGACAATTGGGCTGTACTTTGATTCTGCCCATTCTTCTAGCAACCTGTTAGCATTTCC
      •I  V  L  Q  D  T  G  D  G  K  K  Q  I  A  P  Q  Y  R  I  Q•

3361 GATCGTCCTACAAGACACAGGAGATGGGAAGAAGCAAATCGCCCCGCAATATAGGATCCA
      •R  L  D  L  W  T  D  S  K  E  D  S  V  F  I  T  T  Y  G  F•

3421 GCGCCTTGACTTGTGGACTGATAGTAAGGAGGACTCAGTATTCATCACCACCTATGGATT
      •I  F  Q  V  G  N  E  E  A  T  V  G  M  I  D  D  K  P  K  R•

3481 CATCTTTCAAGTTGGGAATGAAGAAGCCACTGTCGGCATGATCGATGATAAACCCAAGCG
                                                   AvrII
      •E  L  L  S  A  A  M  L  C  L  G  S  V  P  N  T  G  D  L  I•

3541 CGAGTTACTTTCCGCTGCGATGCTCTGCCTAGGAAGCGTCCCAAATACCGGAGACCTTAT
      •E  L  A  R  A  C  L  T  M  I  V  T  C  K  K  S  A  T  N  T•

3601 TGAGCTGGCAAGGGCCTGTCTCACTATGATAGTCACATGCAAGAAGAGTGCAACTAATAC
      •E  R  M  V  F  S  V  V  Q  A  P  Q  V  L  Q  S  C  R  V  V•

3661 TGAGAGAATGGTTTTCTCAGTAGTGCAGGCACCCCAAGTGCTGCAAAGCTGTAGGGTTGT
      •A  N  K  Y  S  S  V  N  A  V  K  H  V  K  A  P  E  K  I  P•

3721 GGCAAACAAATACTCATCAGTGAATGCAGTCAAGCACGTGAAAGCGCCAGAGAAGATTCC
      •G  S  G  T  L  E  Y  K  V  N  F  V  S  L  T  V  V  P  K  K•

3781 CGGGAGTGGAACCCTAGAATACAAGGTGAACTTTGTCTCCTTGACTGTGGTACCGAAGAA
      •D  V  Y  K  I  P  A  A  V  L  K  V  S  G  S  S  L  Y  N  L•

3841 GGATGTCTACAAGATCCCAGCTGCAGTATTGAAGGTTTCTGGCTCGAGTCTGTACAATCT
      •A  L  N  V  T  I  N  V  E  V  D  P  R  S  P  L  V  K  S  L•

3901 TGCGCTCAATGTCACTATTAATGTGGAGGTAGACCCGAGGAGTCCTTTGGTTAAATCTCT
      •S  K  S  D  S  G  Y  Y  A  N  L  F  L  H  I  G  L  M  T  T•

3961 GTCTAAGTCTGACAGCGGATACTATGCTAACCTCTTCTTGCATATTGGACTTATGACCAC
      •V  D  R  K  G  K  K  V  T  F  D  K  L  E  K  K  I  R  S  L•

4021 CGTAGATAGGAAGGGGAAGAAAGTGACATTTGACAAGCTGGAAAAGAAAATAAGGAGCCT
      •D  L  S  V  G  L  S  D  V  L  G  P  S  V  L  V  K  A  R  G•

4081 TGATCTATCTGTCGGGCTCAGTGATGTGCTCGGGCCTTCCGTGTTGGTAAAAGCAAGAGG
      •A  R  T  K  L  L  A  P  F  F  S  S  S  G  T  A  C  Y  P  I•

4141 TGCACGGACTAAGCTTTTGGCACCTTTCTTCTCTAGCAGTGGGACAGCCTGCTATCCCAT
      •A  N  A  S  P  Q  V  A  K  I  L  W  S  Q  T  A  C  L  R  S•

4201 AGCAAATGCTTCTCCTCAGGTGGCCAAGATACTCTGGAGTCAAACCGCGTGCCTGCGGAG
      •V  K  I  I  I  Q  A  G  T  Q  R  A  V  A  V  T  A  D  H  E•

4261 CGTTAAAATCATTATCCAAGCAGGTACCCAACGCGCTGTCGCAGTGACCGCCGACCACGA
      •V  T  S  T  K  L  E  K  G  H  T  L  A  K  Y  N  P  F  K  K•

4321 GGTTACCTCTACTAAGCTGGAGAAGGGGCACACCCTTGCCAAATACAATCCTTTTAAGAA
      •

4381 ATAAgctgcgtctctgagattgcgctccgcccactcacccagatcatcatgacacaaaaa

                                                      Gene End   MluI
4441 actaatctgtcttgattatttacagttagtttacctgtctatcaagttagaaaaaacacg
                                                         M  G  S  K•

       Gene start
4501 cgtacgggtagaagagtctggatcccgaccggcacattcaggacgcaatATGGGCTCCAA
      •L  S  T  R  I  P  A  P  L  M  L  T  T  R  I  T  L  I  L  S•

4561 ACTTTCTACCAGGATTCCAGCACCTCTGATGCTGACCACCCGGATTACGCTGATATTGAG
      •C  I  R  P  T  S  S  L  D  G  R  P  L  A  A  A  G  I  V  V•

4621 CTGTATCCGTCCGACAAGCTCTCTTGACGGCAGGCCTCTTGCAGCTGCAGGAATTGTAGT
      •T  G  D  K  A  V  N  V  Y  T  S  S  Q  T  G  S  I  I  V  K•

4681 AACAGGAGATAAGGCAGTCAATGTATACACCTCGTCTCAGACAGGGTCAATCATAGTCAA
      •L  L  P  N  M  P  R  D  K  E  A  C  A  K  A  P  L  E  A  Y•
```

-continued

4741 GTTGCTCCCGAATATGCCCAGGGATAAAGAGGCGTGTGCAAAAGCCCCATTAGAGGCATA
•N R T L T T L L T P L G D S I R K I Q G•

4801 TAACAGAACACTGACTACTTTGCTAACTCCTCTTGGCGACTCCATCCGCAAGATCCAAGG
Cleavage site
•S V S T S G G G R Q A R L I G A V I G S•

4861 GTCTGTGTCCACGTCTGGAGGAGGCAGACAAGCACGCCTGATAGGTGCTGTTATTGGCAG
NotI
•V A L G V A T A A Q I T A A A A L I Q A•

4921 TGTAGCTCTTGGGGTTGCAACAGCGGCACAGATAACAGCA*GCGGCCGC*CCTAATACAAGC
•N Q N A A N I L R L K E S I A A T N E A•

4981 CAACCAGAATGCCGCCAACATCCTCCGGCTTAAGGAGAGCATTGCTGCAACCAATGAAGC
•V H E V T D G L S Q L S V A V G K M Q Q•

5041 TGTGCATGAAGTCACCGACGGATTATCACAACTATCAGTGGCAGTTGGGAAGATGCAGCA
•F V N D Q F N N T A R E L D C I K I T Q•

5101 GTTCGTCAATGACCAGTTTAATAATACAGCACGAGAATTGGACTGTATAAAAATCACACA
•Q V G V E L N L Y L T E L T T V F G P Q•

5161 ACAGGTTGGTGTAGAGCTAAACCTATACCTAACTGAATTGACTACAGTATTCGGGCCACA
•I T S P A L T Q L T I Q A L Y N L A G G•

5221 GATCACTTCCCCTGCATTAACTCAGTTGACCATCCAAGCACTTTATAATTTAGCTGGTGG
•N M N Y L L T K L G I G N N Q L S S L I•

5281 CAATATGAATTACTTATTAACTAAGTTAGGTATAGGGAACAATCAACTCAGCTCATTAAT
•G S G L I T G Y P I L Y D S Q T Q L L G•

5341 TGGTAGCGGCCTGATCACTGGTTACCCTATACTGTATGATTCACAGACTCAACTCTTGGG
•I Q V N L P S V G N L N N M R A T Y L E•

5401 CATACAAGTGAATTTGCCCTCAGTCGGGAACTTAAATAATATGCGTGCCACCTATTTGGA
•T L S V S T T K G Y A S A L V P K V V T•

5461 GACCTTATCTGTAAGTACAACCAAAGGATATGCCTCAGCACTTGTCCCGAAAGTAGTGAC
•Q V G S V I E E L D T S Y C I E S D L D•

5521 ACAGGTCGGTTCTGTGATAGAAGAGCTCGACACCTCATACTGCATAGAGTCCGATCTGGA
•L Y C T R I V T F P M S P G I Y S C L S•

5581 TTTATATTGTACTAGAATAGTGACATTCCCCATGTCCCCAGGTATTTATTCCTGCTTGAG
•G N T S A C M Y S K T E G A L T T P Y M•

5641 CGGCAACACATCAGCTTGCATGTATTCAAAGACTGAAGGCGCACTCACTACGCCGTATAT
•A L K G S V I A N C K I T T C R C T D P•

5701 GGCCCTTAAAGGCTCGGTTATTGCCAATTGTAAGATAACAACATGTAGATGTACAGACCC
•P G I I S Q N Y G E A V S L I D R H S C•

5761 TCCTGGTATCATATCGCAAAATTATGGAGAAGCCGTATCCCTGATAGATAGACATTCGTG
•N V L S L D G I T L R L S G E F D A T Y•

5821 CAATGTCTTATCATTAGACGGGATAACTCTGAGGCTCAGTGGGGAATTTGATGCAACTTA
•Q K N I S I L D S Q V I V T G N L D I S•

5881 TCAAAAGAACATCTCAATACTAGATTCTCAAGTCATCGTGACAGGCAATCTTGATATCTC
•T E L G N V N N S I S N A L D S L A E S•

5941 AACTGAACTTGGAAACGTCAACAATTCAATCAGCAATGCCTTGGATAGTTTGGCAGAAAG
•N S K L E K I N V R L T S T S A L I T Y•

6001 CAACAGGAAGCTGGAAAAAATCAATGTCAGACTAACCAGCACATCTGCTCTCATTACCTA
•I V L T V I S L V F G A F S L G L A C Y•

6061 TATTGTTCTAACTGTCATTTCTCTAGTTTTCGGTGCATTTAGTTTGGGTTTAGCGTGTTA
•L M Y K Q K A Q Q K T L L W L G N N T L•

6121 CCTGATGTACAAACAGAAGGCACAACAAAAGACCTTGCTATGGCTTGGGAATAATACCCT
•D Q M R A T T R A

6181 CGATCAGATGAGAGCCACTACAAGAGCATGAatgcagataagaggtgggtatatacccaa

Gene End
6241 cagcagcctgtgtatcaattccgataacctgtcaagtagaagact*taagaaaaaa*ctact

Gene start
6301 gggaataagcaaccaaagagcactac*acgggtagaa*cgatcagaggagccacccttcaat
M -continued

```
6361 cggaaattaggcttcacaacatccgttctaccgcatcaccaacaacaagagtcaatcATG
               HpaI
      D  R  A  V  N  R  V  V  L  E  N  E  E  R  E  A  K  N  T  W

6421 GACCGCGCGGTTAACAGAGTCGTGCTGGAGAATGAGGAAAGAGAAGCAAAGAACACATGG
      R  L  V  F  R  I  A  V  L  L  L  M  V  M  T  L  A  I  S  S

6481 CGCCTGGTTTTCCGGATCGCAGTTTTACTTTTAATGGTAATGACTCTAGCTATCTCCTCA
      A  A  L  A  Y  S  T  G  A  S  T  P  H  D  L  A  S  I  L  T

6541 GCTGCCCTGGCATACAGCACGGGGGCCAGTACGCCGCACGACCTCGCAAGCATATTGACT
      V  I  S  K  T  E  D  K  V  T  S  L  L  S  S  S  Q  D  V  I

6601 GTGATCTCCAAGACAGAAGATAAGGTTACGTCTTTACTCAGTTCAAGTCAAGACGTGATA
      D  R  I  Y  K  Q  V  A  L  E  S  P  L  A  L  L  N  T  E  S

6661 GATAGGATATACAAGCAGGTGGCTCTTGAATCCCCGCTGGCACTACTAAACACTGAATCT
      V  I  M  N  A  I  T  S  L  S  Y  Q  I  N  G  A  A  N  N  S

6721 GTAATTATGAATGCAATAACCTCTCTTTCTTATCAAATTAACGGGGCTGCGAACAATAGC
      G  C  G  A  P  V  H  D  P  D  Y  I  G  G  I  G  K  E  L  I

6781 GGATGTGGGGCGCCTGTTCATGACCCAGATTATATCGGGGGGATAGGCAAAGAACTCATA
      V  D  D  I  S  D  V  T  S  F  Y  P  S  A  Y  Q  E  H  L  N

6841 GTGGACGACATCAGTGATGTTACATCATTTTATCCTTCTGCATATCAAGAACACTTGAAT
      F  I  P  A  P  T  T  G  S  G  C  T  R  I  P  S  F  D  M  S

6901 TTCATCCCGGCACCTACTACAGGATCCGGTTGCACTCGGATACCCTCGTTTGACATGAGC
      T  T  H  Y  C  Y  T  H  N  V  I  L  S  G  C  R  D  H  S  H

6961 ACCACCCATTATTGTTATACTCACAATGTGATACTATCCGGTTGCAGAGATCACTCACAC
      S  H  Q  Y  L  A  L  G  V  L  R  T  S  A  T  G  R  V  F  F

7021 TCACATCAATACTTAGCACTTGGTGTGCTTCGGACATCTGCAACAGGGAGGGTATTCTTT
      S  T  L  R  S  I  N  L  D  D  T  Q  N  R  K  S  C  S  V  S

7081 TCTACTCTGCGCTCTATCAATTTAGATGACACCCAAAATCGGAAGTCCTGCAGTGTGAGT
      A  T  P  L  G  C  D  M  L  C  S  K  V  T  G  T  E  E  E  D

7141 GCAACCCCTTTAGGTTGTGATATGCTGTGCTCCAAGGTCACAGGGACTGAAGAGGAGGAT
     Y  K  S  V  A  P  T  S  M  V  H  G  R  L  G  F  D  G  Q  Y

7201 TACAAGTCAGTTGCCCCCACATCAATGGTGCACGGAAGGCTAGGGTTTGACGGTCAATAC
     H  E  K  D  L  D  T  T  V  L  F  K  D  W  V  A  N  Y  P  G

7261 CATGAAAAGGACTTAGACACCACGGTCTTATTTAAGGATTGGGTGGCAAATTACCCAGGA
      A  G  G  G  S  F  I  D  D  R  V  W  F  P  V  Y  G  G  L  K

7321 GCGGGAGGAGGGTCTTTTATTGACGACCGTGTATGGTTCCCAGTTTACGGAGGGCTCAAA
      P  D  S  P  S  D  T  A  Q  E  G  K  Y  V  I  Y  K  R  H  N

7381 CCCGATTCACCCAGTGACACTGCACAAGAAGGGAAATACGTAATATACAAGCGCCATAAC
      N  T  C  P  D  K  Q  D  Y  Q  I  R  K  A  K  S  S  Y  K  P

7441 AACACATGCCCCGATAAACAAGATTACCAAATTCGGAAGGCTAAGTCTTCATATAAACCC
      G  R  F  G  G  K  R  V  Q  Q  A  I  L  S  I  K  V  S  T  S

7501 GGGCGATTTGGTGGGAAGCGCGTACAGCAAGCCATCTTATCCATCAAAGTGTCAACATCT
      L  G  K  D  P  V  L  T  I  P  P  N  T  I  T  L  M  G  A  E

7561 TTGGGTAAGGACCCGGTGCTGACTATTCCACCTAATACAATCACACTCATGGGAGCCGAA
      G  R  I  L  T  V  G  T  S  H  F  L  Y  Q  R  G  S  S  Y  F

7621 GGCAGAATTCTCACAGTGGGGACATCTCACTTCTTGTACCAACGAGGGTCTTCATATTTC
      S  P  A  L  L  Y  P  M  T  V  N  N  K  T  A  T  L  H  S  P

7681 TCCCCTGCCTTATTATATCCCATGACAGTAAATAACAAAACGGCTACACTCCATAGTCCT
      Y  T  F  N  A  F  T  R  P  G  S  V  P  C  Q  A  S  A  R  C

7741 TATACGTTTAATGCTTTCACTCGGCCAGGTAGTGTCCCTTGCCAGGCATCAGCAAGATGC
      P  N  S  C  I  T  G  V  Y  T  D  P  Y  P  L  I  F  H  R  N

7801 CCCAACTCATGCATTACTGGAGTCTATACTGATCCATATCCCTTAATCTTCCATAGGAAT
      H  T  L  R  G  V  F  G  T  M  L  D  D  E  Q  A  R  L  N  P

7861 CATACTCTACGAGGGGTCTTCGGAACGATGCTTGATGATGAACAAGCGAGACTTAACCCC
      V  S  A  V  F  D  N  V  S  R  S  R  V  T  R  V  S  S  S  S
```

-continued

```
7921 GTATCCGCAGTATTCGACAACGTATCCCGCAGTCGTGTCACCCGGGTGAGTTCAAGCAGC
      T  K  A  A  Y  T  T  S  T  C  F  K  V  V  K  T  N  K  T  Y

7981 ACCAAGGCAGCATACACGACATCGACATGTTTCAAAGTTGTCAAGACCAATAAAACTTAT
      C  L  S  I  A  E  I  S  N  T  L  F  G  E  F  R  I  V  P  L

8041 TGTCTTAGTATTGCAGAAATATCCAATACCCTGTTCGGGGAAATTTAGGATCGTTCCCTTA
     SpeI
      L  V  E  I  L  K  D  D  G  V  R  E  A  R  S  G

8101 CTAGTTGAGATCCTCAAGGATGACGGGGTTAGAGAAGCCAGGTCTGGCTAGttgagtcaa

8161 ttataaaggagttggaaagatggcattgtatcacctatcttctgtgacatcaagaatcaa

8221 accgaatgccggcgcgtgctcgaattccatgttgccagttgaccacaatcagccagtgct

                                                Gene End

8281 catgcgatcagattaagccttgtcaatagtctcttgattaagaaaaaaatgtaagtggcaa
                                              Gene start M  A  S  S  G

8341 tgagatacaaggcaaaacagctcatggtaaataatacgggtaggacATGGCGAGCTCCGG
     •P  E  R  A  E  H  Q  I  I  L  P  E  S  H  L  S  S  P  L  V•

8401 TCCTGAAAGGGCAGAGCATCAGATTATCCTACCAGAGTCACACCTGTCTTCACCATTGGT
     •K  H  K  L  L  Y  Y  W  K  L  T  G  L  P  L  P  D  E  C  D•

8461 CAAGCACAAACTACTCTATTACTGGAAATTAACTGGGCTACCGCTTCCTGATGAATGTGA
     •F  D  H  L  I  L  S  R  Q  W  K  K  I  L  E  S  A  S  P  D•

8521 CTTCGACCACCTCATTCTCAGCCGACAATGGAAAAAAATACTTGAATCGGCCTCTCCTGA
     •T  E  R  M  I  K  L  G  R  A  V  H  Q  T  L  N  H  N  S  R•

8581 TACTGAGAGAATGATAAAACTCGGAAGGGCAGTACACCAAACTCTTAACCACAATTCCAG
     •I  T  G  V  L  H  P  R  C  L  E  E  L  A  N  I  E  V  P  D•

8641 AATAACCGGAGTGCTCCACCCCAGGTGTTTAGAAGAACTGGCTAATATTGAGGTCCCAGA
     •S  T  N  K  F  R  K  I  E  K  K  I  Q  I  H  N  T  R  Y  G•

8701 TTCAACCAACAAATTTCGGAAGATTGAGAAGAAGATCCAAATTCACAACACGAGATATGG
     •E  L  F  T  R  L  C  T  H  I  E  K  K  L  L  G  S  S  W  S•

8761 AGAACTGTTCACAAGGCTGTGTACGCATATAGAGAAGAAACTGCTGGGGTCATCTTGGTC
                                                   BsiWI
     •N  N  V  P  R  S  E  E  F  S  S  I  R  T  D  P  A  F  W  F•

8821 TAACAATGTCCCCCGGTCAGAGGAGTTCAGCAGCATTCGTACGGATCCGGCATTCTGGTT
     •H  S  K  W  S  T  A  K  F  A  W  L  H  I  K  Q  I  Q  R  H•

8881 TCACTCAAAATGGTCCACAGCCAAGTTTGCATGGCTCCATATAAAACAGATCCAGAGGCA
     •L  M  V  A  A  R  T  R  S  A  A  N  K  L  V  M  L  T  H  K•

8941 TCTGATGGTGGCAGCTAGGACAAGGTCTGCGGCCAACAAATTGGTGATGCTAACCCATAA
     •V  G  Q  V  F  V  T  P  E  L  V  V  V  T  H  T  N  E  N  K•

9001 GGTAGGCCAAGTCTTTGTCACTCCTGAACTTGTCGTTGTGACGCATACGAATGAGAACAA
     •F  T  C  L  T  Q  E  L  V  L  M  Y  A  D  M  M  E  G  R  D•

9061 GTTCACATGTCTTACCCAGGAACTTGTATTGATGTATGCAGATATGATGGAGGGCAGAGA
     •M  V  N  I  I  S  T  T  A  V  H  L  R  S  L  S  E  K  I  D•

9121 TATGGTCAACATAATATCAACCACGGCGGTGCATCTCAGAAGCTTATCAGAGAAAATTGA
     •D  I  L  R  L  I  D  A  L  A  K  D  L  G  N  Q  V  Y  D  V•

9181 TGACATTTTGCGGTTAATAGACGCTCTGGCAAAAGACTTGGGTAATCAAGTCTACGATGT
     •V  S  L  M  E  G  F  A  Y  G  A  V  Q  L  L  E  P  S  G  T•

9241 CGTATCACTAATGGAGGGATTTGCATACGGAGCTGTCCAGCTACTCGAGCCGTCAGGTAC
     •F  A  G  D  F  F  A  F  N  L  Q  E  L  K  D  I  L  I  G  L•

9301 ATTTGCAGGAGATTTCTTCGCATTCAACCTGCAGGAGCTTAAAGACATTCTAATTGGCCT
     •L  P  N  D  I  A  E  S  V  T  H  A  I  A  T  V  F  S  G  L•

9361 CCTCCCCAATGATATAGCAGAATCCGTGACTCATGCAATCGCTACTGTATTCTCTGGTTT
     •E  Q  N  Q  A  A  E  M  L  C  L  L  R  L  W  G  H  P  L  L•

9421 AGAACAGAATCAAGCAGCTGAGATGTTGTGTCTGTTGCGTCTGTGGGGTCACCCACTGCT
     •E  S  R  I  A  A  K  A  V  R  S  Q  M  C  A  P  K  M  V  D•

9481 TGAGTCCCGTATTGCAGCAAAGGCAGTCAGGAGCCAAATGTGCGCACCGAAAATGGTAGA
     •F  D  M  I  L  Q  V  L  S  F  F  K  G  T  I  I  N  G  Y  R•
```

-continued

```
 9541 CTTTGATATGATCCTTCAGGTACTGTCTTTCTTCAAGGGAACAATCATCAACGGGTACAG
       •K  K  N  A  G  V  W  P  R  V  K  V  D  T  I  Y  G  K  V  I•
 9601 AAAGAAGAATGCAGGTGTGTGGCCGCGAGTCAAAGTGGATACAATATATGGGAAGGTCAT
       •G  Q  L  H  A  D  S  A  E  I  S  H  D  I  M  L  R  E  Y  K•

 9661 TGGGCAACTACATGCAGATTCAGCAGAGATTTCACACGATATCATGTTAAGAGAGTATAA
       •S  L  S  A  L  E  F  E  P  C  I  E  Y  D  P  V  T  N  L  S•

 9721 GAGTTTATCTGCACTTGAATTTGAGCCATGTATAGAATATGACCCTGTCACCAACCTGAG
       •M  F  L  K  D  K  A  I  A  H  P  N  D  N  W  L  A  S  F  R•

 9781 CATGTTCCTAAAAGACAAGGCAATCGCACACCCCAACGATAATTGGCTTGCCTCGTTTAG
       •R  N  L  L  S  E  D  Q  K  K  H  V  K  E  A  T  S  T  N  R•

 9841 GCGGAACCTTCTCTCCGAAGACCAGAAGAAACATGTAAAAGAAGCAACTTCGACTAATCG
       •L  L  I  E  F  L  E  S  N  D  F  D  P  Y  K  E  M  E  Y  L•

 9901 CCTCTTGATAGAGTTTTTAGAGTCAAATGATTTTGATCCATATAAAGAGATGGAATATCT
       •T  T  L  E  Y  L  R  D  D  N  V  A  V  S  Y  S  L  K  E  K•

 9961 GACGACCCTTGAGTACCTTAGAGATGACAATGTGGCAGTATCATACTCGCTCAAGGAGAA
       •E  V  K  V  N  G  R  I  F  A  K  L  T  K  K  L  R  N  C  Q•

10021 GGAAGTGAAAGTTAATGGACGGATCTTCGCTAAGCTGACAAAGAAGTTAAGGAACTGTCA
        •V  M  A  E  G  I  L  A  D  Q  I  A  P  F  F  Q  G  N  G V•

10081 GGTGATGGCGGAAGGGATCCTAGCCGATCAGATTGCACCTTTCTTTCAGGGAAATGGAGT
        •I  Q  D  S  I  S  L  T  K  S  M  L  A  M  S  Q  L  S  F N•

10141 CATTCAGGATAGCATATCCTTGACCAAGAGTATGCTAGCGATGAGTCAACTGTCTTTTAA
        •S  N  K  K  R  I  T  D  C  K  E  R  V  S  S  N  R  N  H D•

10201 CAGCAATAAGAAACGTATCACTGACTGTAAAGAAAGAGTATCTTCAAACCGCAATCATGA
        •P  K  S  K  N  R  R  R  V  A  T  F  I  T  T  D  L  Q  K Y•

10261 TCCGAAAAGCAAGAACCGTCGGAGAGTTGCAACCTTCATAACAACTGACCTGCAAAAGTA
        •C  L  N  W  R  Y  Q  T  I  K  L  F  A  H  A  I  N  Q  L M•

10321 CTGTCTTAATTGGAGATATCAGACAATCAAATTGTTCGCTCATGCCATCAATCAGTTGAT
        •G  L  P  H  F  F  E  W  I  H  L  R  L  M  D  T  T  M  F V•

10381 GGGCCTACCTCACTTCTTCGAATGGATTCACCTAAGACTGATGGACACTACGATGTTCGT
        •G  D  P  F  N  P  P  S  D  P  T  D  C  D  L  S  R  V  P N•

10441 AGGAGACCCTTTCAATCCTCCAAGTGACCCTACTGACTGTGACCTCTCAAGAGTCCCTAA
        •D  D  I  Y  I  V  S  A  R  G  G  I  E  G  L  C  Q  K  L W•

10501 TGATGACATATATATTGTCAGTGCCAGAGGGGGTATCGAAGGATTATGCCAGAAGCTATG
        •T  M  I  S  I  A  A  I  Q  L  A  A  A  R  S  H  C  R  V A•

10561 GACAATGATCTCAATTGCTGCAATCCAACTTGCTGCAGCTAGATCGCATTGTCGTGTTGC
        •C  M  V  Q  G  D  N  Q  V  I  A  V  T  R  E  V  R  S  D D•

10621 CTGTATGGTACAGGGTGATAATCAAGTAATAGCAGTAACGAGAGAGGTAAGATCAGACGA
        •S  P  E  M  V  L  T  Q  L  H  Q  A  S  D  N  F  F  K  E L•

10681 CTCTCCGGAGATGGTGTTGACACAGTTGCATCAAGCCAGTGATAATTTCTTCAAGGAATT
        •I  H  V  N  H  L  I  G  H  N  L  K  D  R  E  T  I  R  S D•

10741 AATTCATGTCAATCATTTGATTGGCCATAATTTGAAGGATCGTGAAACCATCAGGTCAGA
        •T  F  F  I  Y  S  K  R  I  F  K  D  G  A  I  L  S  Q  V L•

10801 CACATTCTTCATATACAGCAAACGAATCTTCAAAGATGGAGCAATCCTCAGTCAAGTCCT
        •K  N  S  S  K  L  V  L  V  S  G  D  L  S  E  N  T  V  M S•

10861 CAAAAATTCATCTAAATTAGTGCTAGTGTCAGGTGATCTCAGTGAAAACACCGTAATGTC
        •C  A  N  I  A  S  T  V  A  R  L  C  E  N  G  L  P  K  D F•

10921 CTGTGCCAACATTGCCTCTACTGTAGCACGGCTATGCGAGAACGGGCTTCCCAAAGACTT
        •C  Y  Y  L  N  Y  I  M  S  C  V  Q  T  Y  F  D  S  E  F S•

10981 CTGTTACTATTTAAACTATATAATGAGTTGTGTGCAGACATACTTTGACTCTGAGTTCTC
        •I  T  N  N  S  H  P  D  L  N  Q  S  W  I  E  D  I  S  F V•

11041 CATCACCAACAATTCGCACCCCGATCTTAATCAGTCGTGGATTGAGGACATCTCTTTTGT
        •H  S  Y  V  L  T  P  A  Q  L  G  G  L  S  N  L  Q  Y  S R•

11101 GCACTCATATGTTCTGACTCCTGCCCAATTAGGGGGACTGAGTAACCTTCAATACTCAAG
        •L  Y  T  R  N  I  G  D  P  G  T  T  A  F  A  E  I  K  R L•
```

-continued

```
11161 GCTCTACACTAGAAATATCGGTGACCCGGGGACTACTGCTTTTGCAGAGATCAAGCGACT
       •E  A  V  G  L  L  S  P  N  I  M  T  N  I  L  T  R  P  P  G•

11221 AGAAGCAGTGGGATTACTGAGTCCTAACATTATGACTAATATCTTAACTAGGCCGCCTGG
       •N  G  D  W  A  S  L  C  N  D  P  Y  S  F  N  F  E  T  V  A•

11281 GAATGGAGATTGGGCCAGTCTGTGCAACGACCCATACTCTTTCAATTTTGAGACTGTTGC
       •S  P  N  I  V  L  K  K  H  T  Q  R  V  L  F  E  T  C  S  N•

11341 AAGCCCAAATATTGTTCTTAAGAAACATACGCAAAGAGTCCTATTTGAAACTTGTTCAAA
       •P  L  L  S  G  V  H  T  E  D  N  E  A  E  E  K  A  L  A  E•

11401 TCCCTTATTGTCTGGAGTGCACACAGAGGATAATGAGGCAGAAGAGAAGGCATTGGCTGA
       •F  L  L  N  Q  E  V  I  H  P  R  V  A  H  A  I  M  E  A  S•

11461 ATTCTTGCTTAATCAAGAGGTGATTCATCCCCGCGTTGCGCATGCCATCATGGAGGCAAG
       •S  V  G  R  R  K  Q  I  Q  G  L  V  D  T  T  N  T  V  I  K•

11521 CTCTGTAGGTAGGAGAAAGCAAATTCAAGGGCTTGTTGACACAACAAACACCGTAATTAA
       •I  A  L  T  R  R  P  L  G  I  K  R  L  M  R  I  V  N  Y  S•

11581 GATTGCGCTTACTAGGAGGCCATTAGGCATCAAGAGGCTGATGCGGATAGTCAATTATTC
       •S  M  H  A  M  L  F  R  D  D  V  F  S  S  S  R  S  N  H  P•

11641 TAGCATGCATGCAATGCTGTTTAGAGACGATGTTTTTTCCTCCAGTAGATCCAACCACCC
       •L  V  S  S  N  M  C  S  L  T  L  A  D  Y  A  R  N  R  S  W•

11701 CTTAGTCTCTTCTAATATGTGTTCTCTGACACTGGCAGACTATGCACGGAATAGAAGCTG
       •S  P  L  T  G  G  R  K  I  L  G  V  S  N  P  D  T  I  E  L•

11761 GTCACCTTTGACGGGAGGCAGGAAAATACTGGGTGTATCTAATCCTGATACGATAGAACT
       •V  E  G  E  I  L  S  V  S  G  G  C  T  R  C  D  S  G  D  E•

11821 CGTAGAGGGTGAGATTCTTAGTGTAAGCGGAGGGTGTACAAGATGTGACAGCGGAGATGA
       •Q  F  T  W  F  H  L  P  S  N  I  E  L  T  D  D  T  S  K  N•

11881 ACAATTTACTTGGTTCCATCTTCCAAGCAATATAGAATTGACCGATGACACCAGCAAGAA
       •P  P  M  R  V  P  Y  L  G  S  K  T  Q  E  R  R  A  A  S  L•

11941 TCCTCCGATGAGGGTACCATATCTCGGGTCAAAGACACAGGAGAGGAGAGCTGCCTCACT
       •A  K  I  A  H  M  S  P  H  V  K  A  A  L  R  A  S  S  V  L•

12001 TGCAAAAATAGCTCATATGTCGCCACATGTAAAGGCTGCCCTAAGGGCATCATCCGTGTT
       •I  W  A  Y  G  D  N  E  V  N  W  T  A  A  L  T  I  A  K  S•

12061 GATCTGGGCTTATGGGGATAATGAAGTAAATTGGACTGCTGCTCTTACGATTGCAAAATC
       •R  C  N  V  N  L  E  Y  L  R  L  L  S  P  L  P  T  A  G  N•

12121 TCGGTGTAATGTAAACTTAGAGTATCTTCGGTTACTGTCCCCTTTACCCACGGCTGGGAA
       •L  Q  H  R  L  D  D  G  I  T  Q  M  T  F  T  P  A  S  L  Y•

12181 TCTTCAACATAGACTAGATGATGGTATAACTCAGATGACATTCACCCCTGCATCTCTCTA
       •R  V  S  P  Y  I  H  I  S  N  D  S  Q  R  L  F  T  E  E  G•

12241 CAGGGTGTCACCTTACATTCACATATCCAATGATTCTCAAAGGCTGTTCACTGAAGAAGG
       •V  K  E  G  N  V  V  Y  Q  Q  I  M  L  L  G  L  S  L  I  E•

12301 AGTCAAAGAGGGGAATGTGGTTTACCAACAGATCATGCTCTTGGGTTTATCTCTAATCGA
      ClaI
       •S  I  F  P  M  T  T  T  R  T  Y  D  E  I  T  L  H  L  H  S•

12361 ATCGATATTTCCAATGACAACAACCAGGACATATGATGAGATCACACTGCACCTACATAG
       •K  F  S  C  C  I  R  E  A  P  V  A  V  P  F  E  L  L  G  V•

12421 TAAATTTAGTTGCTGTATCAGAGAAGCACCTGTTGCGGTTCCTTTCGAGCTACTTGGGGT
       •V  P  E  L  R  T  V  T  S  N  K  F  M  Y  D  P  S  P  V  S•

12481 GGTACCGGAACTGAGGACAGTGACCTCAAATAAGTTTATGTATGATCCTAGCCCTGTATC
       •E  G  D  F  A  R  L  D  L  A  I  F  K  S  Y  E  L  N  L  E•

12541 GGAGGGAGACTTTGCGAGACTTGACTTAGCTATCTTCAAGAGTTATGAGCTTAATCTGGA
       •S  Y  P  T  I  E  L  M  N  I  L  S  I  S  S  G  K  L  I  G•

12601 GTCATATCCCACGATAGAGCTAATGAACATTCTTTCAATATCCAGCGGGAAGTTGATTGG
       •Q  S  V  V  S  Y  D  E  D  T  S  I  K  N  D  A  I  I  V  Y•

12661 CCAGTCTGTGGTTTCTTATGATGAAGATACCTCCATAAAGAATGACGCCATAATAGTGTA
       •D  N  T  R  N  W  I  S  E  A  Q  N  S  D  V  V  R  L  F  E•

12721 TGACAATACCCGAAATTGGATCAGTGAAGCTCAGAATTCAGATGTGGTCCGCCTATTTGA
       •Y  A  A  L  E  V  L  L  D  C  S  Y  Q  L  Y  Y  L  R  V  R•
```

-continued

```
12781 ATATGCAGCACTTGAAGTGCTCCTCGACTGTTCTTACCAACTCTATTACCTGAGAGTAAG
       •G  L  D  N  I  V  L  Y  M  G  D  L  Y  K  N  M  P  G  I  L•

12841 AGGCCTAGACAATATTGTCTTATATATGGGTGATTTATACAAGAATATGCCAGGAATTCT
       •L  S  N  I  A  A  T  I  S  H  P  V  I  H  S  R  L  H  A  V•

12901 ACTTTCCAACATTGCAGCTACAATATCTCATCCCGTCATTCATTCAAGGTTACATGCAGT
       •G  L  V  N  H  D  G  S  H  Q  L  A  D  T  D  F  I  E  M  S•

12961 GGGCCTGGTCAACCATGACGGATCACACCAACTTGCAGATACGGATTTTATCGAAATGTC
       •A  K  L  L  V  S  C  T  R  R  V  I  S  G  L  Y  S  G  N  K•

13021 TGCAAAACTATTAGTATCTTGCACCCGACGTGTGATCTCCGGCTTATATTCAGGAAATAA
       •Y  D  L  L  F  P  S  V  L  D  D  N  L  N  E  K  M  L  Q  L•

13081 GTATGATCTGCTGTTCCCATCTGTCTTAGATGATAACCTGAATGAGAAGATGCTTCAGCT
       •I  S  R  L  C  C  L  Y  T  V  L  F  A  T  T  R  E  I  P  K•

13141 GATATCCCGGTTATGCTGTCTGTACACGGTACTCTTTGCTACAACAAGAGAAATCCCGAA
       •I  R  G  L  T  A  E  E  K  C  S  I  L  T  E  Y  L  L  S  D•

13201 AATAAGAGGCTTAACTGCAGAAGAGAAATGTTCAATACTCACTGAGTATTTACTGTCGGA
       •A  V  K  P  L  L  S  P  D  Q  V  S  S  I  M  S  P  N  I  I•

13261 TGCTGTGAAACCATTACTTAGCCCCGATCAAGTGAGCTCTATCATGTCTCCTAACATAAT
       •T  F  P  A  N  L  Y  Y  M  S  R  K  S  L  N  L  I  R  E  R•

13321 TACATTCCCAGCTAATCTGTACTACATGTCTCGGAAGAGCCTCAATTTGATCAGGGAAAG
       •E  D  R  D  T  I  L  A  L  L  F  P  Q  E  P  L  L  E  F  P•

13381 GGAGGACAGGGATACTATCCTGGCGTTGTTGTTCCCCCAAGAGCCATTATTAGAGTTCCC
       •S  V  Q  D  I  G  A  R  V  K  D  P  F  T  R  Q  P  A  A  F•

13441 TTCTGTGCAAGATATTGGTGCTCGAGTGAAAGATCCATTCACCCGACAACCTGCGGCATT
       •L  Q  E  L  D  L  S  A  P  A  R  Y  D  A  F  T  L  S  Q  I•

13501 TTTGCAAGAGTTAGATTTGAGTGCTCCAGCAAGGTATGACGCATTCACACTTAGTCAGAT
       •H  P  E  L  T  S  P  N  P  E  E  D  Y  L  V  R  Y  L  F  R•

13561 TCATCCTGAACTCACATCTCCAAATCCGGAGGAAGACTACTTAGTACGATACTTGTTCAG
       •G  I  G  T  A  S  S  S  W  Y  K  A  S  H  L  L  S  V  P  E•

13621 AGGGATAGGGACTGCATCTTCCTCTTGGTATAAGGCATCCCATCTCCTTTCTGTACCCGA
       •V  R  C  A  R  H  G  N  S  L  Y  L  A  E  G  S  G  A  I  M•

13681 GGTAAGATGTGCAAGACACGGGAACTCCTTATACTTAGCTGAAGGGAGCGGAGCCATCAT
       •S  L  L  E  L  H  V  P  H  E  T  I  Y  Y  N  T  L  F  S  N•

13741 GAGTCTTCTCGAACTGCATGTACCACATGAAACTATCTATTACAATACGCTCTTTTCAAA
       •E  M  N  P  P  Q  R  H  F  G  P  T  P  T  Q  F  L  N  S  V•

13801 TGAGATGAACCCCCCGCAACGACATTTCGGGCCGACCCCAACTCAGTTTTTGAATTCGGT
       •V  Y  R  N  L  Q  A  E  V  T  C  K  D  G  F  V  Q  E  F  R•

13861 TGTTTATAGGAATCTACAGGCGGAGGTAACATGCAAAGATGGATTTGTCCAAGAGTTCCG
       •P  L  W  R  E  N  T  E  E  S  D  L  T  S  D  K  A  V  G  Y•

13921 TCCATTATGGAGAGAAAATACAGAGGAAAGTGACCTGACCTCAGATAAAGCAGTGGGGTA
       •I  T  S  A  V  P  Y  R  S  V  S  L  L  H  C  D  I  E  I  P•

13981 TATTACATCTGCAGTGCCCTACAGATCTGTATCATTGCTGCATTGTGACATTGAAATTCC
       •P  G  S  N  Q  S  L  L  D  Q  L  A  I  N  L  S  L  I  A  M•

14041 TCCAGGGTCCAATCAAAGCTTACTAGATCAACTAGCTATCAATTTATCTCTGATTGCCAT
       •H  S  V  R  E  G  G  V  V  I  I  K  V  L  Y  A  M  G  Y  Y•

14101 GCATTCTGTAAGGGAGGGCGGGGTAGTAATCATCAAAGTGTTGTATGCAATGGGATACTA
       •F  H  L  L  M  N  L  F  A  P  C  S  T  K  G  Y  I  L  S  N•

14161 CTTTCATCTACTCATGAACTTGTTTGCTCCGTGTTCCACAAAAGGATATATTCTCTCTAA
       •G  Y  A  C  R  G  D  M  E  C  Y  L  V  F  V  M  G  Y  L  G•

14221 TGGTTATGCATGTCGAGGAGATATGGAGTGTTACCTGGTATTTGTCATGGGTTACCTGGG
       •G  P  T  F  V  H  E  V  V  R  M  A  K  T  L  V  Q  R  H  G•

14281 CGGGCCTACATTTGTACATGAGGTGGTGAGGATGGCAAAAACTCTGGTGCAGCGGCACGG
       •T  L  L  S  K  S  D  E  I  T  L  T  R  L  F  T  S  Q  R  Q•

14341 TACGCTTTTGTCTAAATCAGATGAGATCACACTGACCAGGTTATTCACCTCACAGCGGCA
       •R  V  T  D  I  L  S  S  P  L  P  R  L  I  K  Y  L  R  K  N•
```

-continued

```
14401 GCGTGTGACAGACATCCTATCCAGTCCTTTACCAAGATTAATAAAGTACTTGAGGAAGAA
       •I  D  T  A  L  I  E  A  G  G  Q  P  V  R  P  F  C  A  E  S•

14461 TATTGACACTGCGCTGATTGAAGCCGGGGGACAGCCCGTCCGTCCATTCTGTGCGGAGAG
       •L  V  S  T  L  A  N  I  T  Q  I  T  Q  I  I  A  S  H  I  D•

14521 TCTGGTGAGCACGCTAGCGAACATAACTCAGATAACCCAGATCATCGCTAGTCACATTGA
       •T  V  I  R  S  V  I  Y  M  E  A  E  G  D  L  A  D  T  V  F•

14581 CACAGTTATCCGGTCTGTGATATATATGGAAGCTGAGGGTGATCTCGCTGACACAGTATT
       •L  F  T  P  Y  N  L  S  T  D  G  K  K  R  T  S  L  K  Q  C•

14641 TCTATTTACCCCTTACAATCTCTCTACTGACGGGAAAAAGAGGACATCACTTAAACAGTG
       •T  R  Q  I  L  E  V  T  I  L  G  L  R  V  E  N  L  N  K  I•

14701 CACGAGACAGATCCTAGAGGTTACAATACTAGGTCTTAGAGTCGAAAATCTCAATAAAAT
       •G  D  I  I  S  L  V  L  K  G  M  I  S  M  E  D  L  I  P  L•

14761 AGGCGATATAATCAGCCTAGTGCTTAAAGGCATGATCTCCATGGAGGACCTTATCCCACT
                                                         AvrII
       •R  T  Y  L  K  H  S  T  C  P  K  Y  L  K  A  V  L  G  I  T•

14821 AAGGACATACTTGAAGCATAGTACCTGCCCTAAATATTTGAAGGCTGTCCTAGGTATTAC
       •K  L  K  E  M  F  T  D  T  S  V  L  Y  L  T  R  A  Q  Q  K•

14881 CAAACTCAAAGAAATGTTTACAGACACTTCTGTACTGTACTTGACTCGTGCTCAACAAAA
       •F  Y  M  K  T  I  G  N  A  V  K  G  Y  Y  S  N  C  D  S

14941 ATTCTACATGAAAACTATAGGCAATGCAGTCAAAGGATATTACAGTAACTGTGACTCTTA

15001 Acgaaaatcacatattaataggctcctttttggccaattgtattcttgttgatttaatc

               Gene End
15061 atattatgttagaaaaaagttgaaccctgactccttaggactcgaattcgaactcaaata

15121 aatgtcttaaaaaaaggttgcgcacaattattcttgagtgtagtctcgtcattcaccaaa
               HDV ribozyme sequences

15181 tctttgtttggtGGGTCGGCATGGCATCTCCACCTCCTCGCGGTCCGACCTGGGCATCCG

15241 AAGGAGGACGTCGTCCACTCGGATGGCTAAGGGAGAGCtcggatccggctgctaacaaag
                                          T7 terminator

15301 cccgaaaggaagctgagttggctgctgccaccgctgagcaataaCTAGCATAACCCCTTG

15361 GGGCCTCTAAACGGGTCTTGAGGGGTTTTTTGcatatgcggtgtgaaataccgcacagat

15421 gcgtaaggagaaaataccgcatcaggcgctcttccgcttcctcgctcactgactcgctgc

15481 gctcggtcgttcggctgcggcgagcggtatcagctcactcaaaggcggtaatacggttat

15541 ccacagaatcaggggataacgcaggaaagaacatgtgagcaaaaggccagcaaaaggcca

15601 ggaaccgtaaaaaggccgcgttgctggcgtttttccataggctccgcccccctgacgagc

15661 atcacaaaaatcgacgctcaagtcagaggtggcgaaacccgacaggactataaagatacc

15721 aggcgtttccccctggaagctccctcgtgcgctctcctgttccgaccctgccgcttaccg

15781 gatacctgtccgcctttctcccttcgggaagcgtggcgctttctcatagctcacgctgta

15841 ggtatctcagttcggtgtaggtcgttcgctccaagctgggctgtgtgcacgaaccccccg

15901 ttcagcccgaccgctgcgccttatccggtaactatcgtcttgagtccaacccggtaagac

15961 acgacttatcgccactggcagcagccactggtaacaggattagcagagcgaggtatgtag

16021 gcggtgctacagagttcttgaagtggtggcctaactacggctacactagaaggacagtat

16081 ttggtatctgcgctctgctgaagccagttaccttcggaaaaagagttggtagctcttgat

16141 ccggcaaacaaaccaccgctggtagcggtggtttttttgtttgcaagcagcagattacgc

16201 gcagaaaaaaaggatctcaagaagatcctttgatcttttctacggggtctgacgctcagt

16261 ggaacgaaaactcacgttaagggattttggtcatgagattatcaaaaaggatcttcacct

16321 agatccttttaaattaaaaatgaagttttaaatcaatctaaagtatatatgagtaaactt

16381 ggtctgacagttaccaatgcttaatcagtgaggcacctatctcagcgatctgtctatttc
```

-continued

```
16441 gttcatccatagttgcctgactccccgtcgtgtagataactacgatacgggagggcttac

16501 catctggccccagtgctgcaatgataccgcgagacccacgctcaccggctccagatttat

16561 cagcaataaaccagccagccggaagggccgagcgcagaagtggtcctgcaactttatccg

16621 cctccatccagtctattaattgttgccgggaagctagagtaagtagttcgccagttaata

16681 gtttgcgcaacgttgttgccattgctgcaggcatcgtggtgtcacgctcgtcgtttggta

16741 tggcttcattcagctccggttcccaacgatcaaggcgagttacatgatcccccatgttgt

16801 gcaaaaaagcggttagctccttcggtcctccgatcgttgtcagaagtaagttggccgcag

16861 tgttatcactcatggttatggcagcactgcataattctcttactgtcatgccatccgtaa

16921 gatgcttttctgtgactggtgagtactcaaccaagtcattctgagaatagtgtatgcggc

16981 gaccgagttgctcttgcccggcgtcaacacgggataataccgcgccacatagcagaactt

17041 taaaagtgctcatcattggaaaacgttcttcggggcgaaaactctcaaggatcttaccgc

17101 tgttgagatccagttcgatgtaacccactcgtgcacccaactgatcttcagcatctttta

17161 ctttcaccagcgtttctgggtgagcaaaaacaggaaggcaaaatgccgcaaaaaagggaa

17221 taagggcgacacggaaatgttgaatactcatactcttcctttttcaatattattgaagca

17281 tttatcagggttattgtctcatgagcggatacatatttgaatgtatttagaaaaataaac

17341 aaataggggttccgcgcacatttccccgaaaagtgccacctgacgtctaagaaaccatta

17401 ttatcatgacattaacctataaaaataggcgtatcacgaggccctttcgtcttcaagaat
             T7 Promoter

17461 TCTAATACGACTCACTATAGG
```

The amino acid sequences of NP, P, M, F, HN and L proteins expressed by the vector for transcription of the genome (pTNH-c4152R2L) are shown in SEQ ID NO: 2 to 7, respectively.

In another aspect, the present invention relates to a recombinant Newcastle disease virus including coding regions of P, M, F, HM and L gene, wherein the coding regions of the NP, P, M and L genes are derived from a low-pathogenic Newcastle disease virus, and the coding regions of the F and HN genes are derived from a high-pathogenic Newcastle disease virus, wherein the F protein coding sequence is characterized by substitution of the codon for the $115^{th}$ amino acid of the F protein of the high-pathogenic Newcastle disease virus with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU.

The HN gene of the recombinant Newcastle disease virus may be additionally mutated, so that the codons for the $1^{st}$ to $569^{th}$ amino acids of the HN protein encodes those of a high-pathogenic Newcastle disease virus and the codons for the amino acids after the $570^{th}$ position encode those of a low-pathogenic Newcastle disease virus including the La Sota strain.

In a preferred embodiment of the present invention, the recombinant Newcastle disease virus may be KCTC10984BP.

The recombinant Newcastle disease virus according to the present invention is characterized in that the surface antigen and antigenicity are identical or similar to those of high-pathogenic field strains, and the pathogenicity is lower than that of existing low-pathogenic vaccine strains. The pathogenic Newcastle disease virus has the furin recognizing cleavage region in the F protein, and when the cleavage region is cleaved by furin, the fusion peptide region where the F protein is fused with cellular membrane is exposed, thereby obtaining infectivity. Since furin is distributed in most cells in the body, the Newcastle disease virus can be systemically infected in the body, thereby showing high pathogenicity.

In the vector for transcription of the virus genome of the present invention, the low-pathogenic Newcastle disease virus is the same as defined above, for example, the low-pathogenic Newcastle disease virus may be selected from the group consisting of Newcastle disease viruses belonging to Type I or Type II, and preferably may be the La Sota/46 strain (AY845400) belonging to the Type II. The high-pathogenic Newcastle disease virus is the same as defined above, it may be any one selected from the group consisting of Newcastle disease viruses belonging to Type V, Type VI, Type VII, Type VIII, and Type XI, which are field strains prevailing throughout the world, and is preferably selected from the group consisting of Newcastle disease viruses belonging to Type VI and Type VII. In a preferred embodiment of the present invention, the high-pathogenic Newcastle disease virus may be KBNP-4152 (deposition No, KCTC10919BP). A method of preparing the KBNP-4152 strain and characteristics thereof are the same as described in Korean Patent Application No. 2006-0026667 and 'Cho S H, Aim Y J, Kim S J, Kwon H J. Characterization of a Newcastle disease virus with variation in the major Hemagglutinin-Neuraminidase (HN) linear epitope. The 49th Annual Meeting of the Korean Society of Veterinary Science 2005, 45 (3, suppl), 199', which are incorporated herein by reference). As used herein, the high-pathogenic Newcastle disease viruses and the low-pathogenic Newcastle disease viruses are defined as described above, as long as they are differently defined.

In the attenuation of the Newcastle disease virus using conventional reverse genetics, there is an example of substituting the $115^{th}$ amino acid with glycine, but any mutation at only one base of the codon for the substituted glycine can lead to the alteration of the $115^{th}$ amino acid to a basic amino acid such as lysine or arginine, and the virus may recover its pathogenicity again.

However, in the recombinant Newcastle disease virus according to the present invention, the codon encoding the $115^{th}$ amino acid of the F protein is substituted with the codon encoding a non-basic amino acid, wherein the codon encoding the non-basic amino acid cannot be converted into one encoding a basic amino acid until at least two point mutations occur therein. Therefore, the probability of the recombinant virus recovers its pathogenicity is very low, and the stability of the virus is significantly increased compared with existing other attenuated strains. When the cleavage site of the F protein is mutated according to the present invention, the cleavage site of the F protein is cleaved by not furin, whereby a systemic infection cannot occur, but trypsin or trypsin-like enzymes distributed in only a few organs in the body, respiratory organs and digestive organs, resulting in a localized infection.

In order to achieve such effect, the codon for the $115^{th}$ amino acid of the F protein of the present invention is substituted with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU.

In another aspect, the present invention relates to a method of preparing a recombinant Newcastle disease virus, including the steps of:

substituting nucleotide sequences encoding the F and HN protein of a low-pathogenic Newcastle disease virus with those of a high-pathogenic Newcastle disease virus; and substituting the codon for the $115^{th}$ amino acid of F protein of the high-pathogenic Newcastle disease virus with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU, wherein the virus is characterized by having antigenicity equal or similar to the high-pathogenic Newcastle disease virus and decreased pathogenicity.

In preparing the recombinant Newcastle disease virus, the HN gene may be additionally mutated so that the codons for the $1^{st}$ to $569^{th}$ amino acids of the HN protein encodes those of a high-pathogenic Newcastle disease virus and the codons for the amino acids after the $570^{th}$ position encode those of a low-pathogenic Newcastle disease virus including the La Sota strain.

In addition, the method includes the steps of: transfecting the above-described vector for transcription of the Newcastle disease virus genome according to the present invention into a host cell; and rescuing the recombinant Newcastle disease virus. The host cell used in the transfection is not particularly limited, and preferably may be an animal cell selected from the group consisting of Hep2 and BHK21.

In another aspect, the present invention relates to a method of attenuating the pathogenicity and improving the antigenicity and stability of the Newcastle disease virus, including the steps of:

substituting nucleotide sequences encoding the F and HN protein of a low-pathogenic Newcastle disease virus with those of a high-pathogenic Newcastle disease virus; and substituting the codon encoding the $115^{th}$ amino acid of F protein of the high-pathogenic Newcastle disease virus with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU.

In the method, the HN gene of the vector may be additionally mutated so that the codons for the $1^{st}$ to $569^{th}$ amino acids of the HN protein encodes those of a high-pathogenic Newcastle disease virus and the codons for the amino acids after $570^{th}$ position encode those of a low-pathogenic Newcastle disease virus including the La Sota strain.

In another aspect, the present invention relates to a Newcastle disease vaccine containing the recombining Newcastle disease virus with an increased antigenicity and a decreased pathogenicity as described above. The Newcastle disease vaccine may be an inactivated vaccine obtained by inactivating the recombining Newcastle disease virus. The inactivation may be performed by using any conventional means known to the technical field to which this invention belongs, for example, using formaldehyde or bromomethyl amine hydrobromide, etc. Alternatively, it is also possible to use the Newcastle disease vaccine in the form of a live vaccine, or an in ovo vaccine applicable directly to a fertilized egg, due to the low pathogenicity, high stability and high safety of the recombining Newcastle disease virus. When the vaccine of the present invention is used in the form of a live vaccine, its administration pathway is not limited, and for example, it may be administered through subcutaneous or muscular pathway, or by means of spray or drinking water, appropriately for symptoms and purposes. The dose of the vaccine of the present invention may depend on the administration method, and the condition of subject to be administered, and for example, the dose of the vaccine may be from $10^1$ $EID_{50}$ (50% egg-infectious dose) to $10^{12}$ $EID_{50}$ strain/individual. More specifically, in the case of the inactivated vaccine, the vaccine may be preferably used in the amount of $10^{6.0\sim12}$ $EID_{50}$/individual, and more preferably $10^{8.0\sim10}$ $EID_{50}$/individual. In the case of the in ovo vaccine, it may be used in the amount of $10^{1\sim9.0}$ $EID_{50}$/egg according to the level of maternal antibodies in the egg to be administered, and more preferably, in the amount of $10^{3.0\sim7.0}$ $EID_{50}$/egg.

As described above, the pathogenicity of the Newcastle disease virus is determined by the amino acid sequence of the furin recognizing cleavage region of the F protein. That is, when the amino acid sequence of the furin recognizing cleavage region of the F protein is R-X-K/R-R (positioning from $113^{th}$ to $116^{th}$ positions; hereinafter, the position range is applied to all amino acid tetramers, unless differently defined), the F protein is cleaved and activated by furin existing in all cells of whole body, resulting in a systemic infection, thereby showing high pathogenicity. On the contrary, when there is only one basic amino acid, or discontinuous basic amino acids, such as R-Q-G-R or G-Q-G-R, the F protein is activated by trypsin or analogs thereof existing in parts of the epithelial cells of the digestive tract and trachea only, resulting in a localized infection, thereby showing low pathogenicity. As to HN, a highly pathogenic virus consists of 571 amino acids, which is a relatively short amino acid length. On the contrary, a low pathogenic virus consists of 577 or 616 amino acids, which is a relatively long amino acid length, wherein the additional C-terminal region makes it possible to distinguish the low pathogenic virus from the high pathogenic virus. Therefore, it is possible to prepare viruses with various levels of pathogenicities by preparing recombinant viruses with various combinations of the cleavage site of the F protein and the additional C-terminal region of HN.

Particularly, the present invention is characterized in that the amino acid sequence of the cleavage site of the F protein is substituted by a safer amino acid sequence, in order to inhibit the recombinant virus from obtaining pathogenicity by any possible genetic variations. As described above, the amino acid sequence of the cleavage site of the F protein of a low pathogenic virus is R-Q-G-R or K-Q-G-R. In order for the low pathogenic virus to be modified into a high pathogenic virus, the above amino acid sequence should be changed into R-X-K/R-R, and thus, the glycine (G) located at the third position has to be changed into arginine (R) or lysine (K). Such change from G to R or K may readily occur by only one point mutation. That is, considering that the codon for glycine is GGA, GGC, GGG or GGU, and the codon for arginine or lysine is AGA, AGG, CGA, CGC, CGG, CGU, AAA or AAG, glycine may be easily modified to arginine or lysine even if only one point mutation occur in any of the glycine codons, resulting converting a low pathogenic virus into a high pathogenic one. In fact, it has been reported in Australia in 2001 that a non-pathogenic Newcastle disease virus, Ulster like strain, became pathogenic through a similar mechanism to the above, thereby causing Newcastle disease.

Therefore, in order to remarkably decrease the probability of the increase of pathogenicity caused by any point mutation in the vaccine strain compared with the existing strain, the present invention provides a technique to prepare a recombinant virus using any conventional method, such as a PTDS (PCR-based-two-steps DNA synthesis) method, wherein the recombinant virus shows a low probability of such amino acid change into lysine or arginine caused by point mutation. That is, in the present invention, an amino acid, glycine, located at the $115^{th}$ position of the F protein of a conventional low-pathogenic virus is substituted by any one selected from the group consisting of alanine, aspartic acid, phenylalanine, isoleucine, leucine, serine, theronine, valine and tyrosine, for example resulting in R-Q-A-R or G-Q-A-R, wherein the amino acid that is substituted for the $115^{th}$ glycine can be changed to lysine or arginine only when all or at least two bases are mutated in the codon for the amino acid to be substituted for the $115^{th}$ glycine, allowing preparation of a safer vaccine strain.

The level of pathogenicity of the recombinant Newcastle disease virus is determined by measuring mean death time (MDT), and intracerebral pathogenicity index (ICPI). The biological properties of the recombinant Newcastle disease virus is confirmed by $EID_{50}$ (50% egg-infectious dose), hemagglutination dissociation rate, and the like. As a result, the recombinant Newcastle disease virus according to the present invention has remarkably lower pathogenicity than the existing low pathogenic strains.

The present invention is further explained in more detail with reference to the following examples. These examples, however, should not be interpreted as limiting the scope of the present invention in any manner.

EXAMPLE

Example 1

Cloning of a Virus Gene 1.1. Synthesis of a Virus cDNA

Recently, as a virus representing the Newcastle disease viruses, a velogenic and antigenic variant strain that is domestically prevalent, the SNU4152 strain that was isolated in the Avian Disease & Laboratory, College of Veterinary Medicine of Seoul National University, was selected. The virus was cloned after plaque-purifying 3 times on chicken embryonic fibroblast (CEF), and was sub-cultivated twice in an SPF embryonated egg. The cloned strain was named KBNP-4152 and deposited with the Korean Collection for Type Culture (Korea Research Institute of Bioscience and Biotechnology, Taejon, Republic of Korea) on Mar. 10, 2006, and assigned deposition No. KCTC10919BP.

RNA manipulation was performed in a glass and a plastic ware without RNase, and all solutions were used to triple distilled water (DEPC-DW) that was autoclaved and treated with 1% diethyl-pyrocarbonate (DEPC). Then, the virus was centrifuged at 21,000 rpm for 70 min in a Beckman SW40 rotor, and an obtained pellet was re-suspended in a buffer solution (50 mM Tris HCl pH7.5, 50 mM EDTA, 0.5% SDS). After treating with protease K (200 μg/ml, Invitrogen Co.) at 37° C. for 90 min, RNA was extracted by acidic phenol extraction. Then, after precipitating the RNA by ethanol precipitation, the obtained precipitate was washed with 75% ethanol, dried, and re-suspended in DEPC-treated water.

1 μℓ of the extracted RNA quantified by ultraviolet spectrometer (Eppendorf, Biophotometer), 1 μℓ of primer (10 pmol/μℓ) shown in Table 1, and 10 μℓ of DEPC-water were mixed, and the mixture was denaturated at 70° C. for 10 min. After adding 4 μℓ of 5×RT buffer solution (250 mM Tris-HCl, pH 8.3, 375 mM KCl, 15 mM $MgCl_2$; GibcoBRL/Life Technologies), 2 μℓ of 0.1 M DTT, and 2 μℓ of 10 mM dNTPs (each 2.5 mM) to the mixture, the mixture was reacted at 42° C. for 2 min. Then, 1 μℓ of reverse transcriptase (200 unit, Invitrogen co.) was added to the reacted mixture, which was then reacted at 42° C. for 60 min.

TABLE 1

Primers used for synthesis of KBNP-4152 cDNA

| Primer | Primer sequence (5'->3') |
|---|---|
| ND-ZJ-1F | cgtctcgaccaaacagagaatctgtgaggtac (SEQ ID NO: 8) |
| ND-ZJ-1746F | gacaacacaggcacagctcg (SEQ ID NO: 9) |

TABLE 1-continued

| Primers used for synthesis of KBNP-4152 cDNA | |
|---|---|
| Primer | Primer sequence (5'->3') |
| ND-ZJ-2827F | catctccttacgtgacacaagg (SEQ ID NO: 10) |
| ND-ZJ-F-F | **tcgcga**cgcaatatgg ctccaaactt tc (SEQ ID NO: 11) |
| ND-ZJ-HN-F | **ccgcgg**caccgacaac aagagtcaat catg (SEQ ID NO: 12) |
| ND-ZJ-8100F | actagttgagatcctcaaggatgatag (SEQ ID NO: 13) |
| ND-ZJ-11648F | catgcaatgttgtccagagatg (SEQ ID NO: 14) |
| ND-ZJ-12539F | tcagagagagatttcgcgagac (SEQ ID NO: 15) |
| ND-ZJ-14021F | cattgtgacattgagattcctcc (SEQ ID NO: 16) |

1.2. Cloning of a Virus Gene

Based on previous GenBank data, the 9 kinds of synthesized virus cDNA corresponding to 15,192 bp nucleotide sequences were amplified by PCR reaction using 9 primer sets shown in Table 2, and cloned. The obtained clones were named Z1 to Z9.

TABLE 2

| Primers used for cloning of KBNP-4152 viral gene | |
|---|---|
| Primer | Primer sequence (5'->3') |
| ND-ZJ-1F | cgtctcgaccaaacagagaatctgtgaggtac (SEQ ID NO: 8) |
| ND-ZJ-1844R | tcgtcttggtctctggatgtctc (SEQ ID NO: 17) |
| ND-ZJ-1746F | gacaacacaggcacagctcg (SEQ ID NO: 9) |
| ND-ZJ-2948R | cttctccactcccatgtcagg (SEQ ID NO: 18) |
| ND-ZJ-2827F | catctccttacgtgacacaagg (SEQ ID NO: 10) |
| ND-ZJ-4612R | cagcataatccgggtgatcagc (SEQ ID NO: 19) |
| ND-ZJ-F-F | **tcgcga**cgcaatatggctccaaactttc (SEQ ID NO: 11) |
| ND-ZJ-F-R | **ccgcgg**tagaacggatgttgtgaagcctaa (SEQ ID NO: 20) |
| ND-ZJ-HN-F | **ccgcgg**caccgacaacaagagtcaatcatg (SEQ ID NO: 12) |
| ND-ZJ-HN-R | ctca**actagt**aagggaacgatcctaaattcc (SEQ ID NO: 21) |
| ND-ZJ-8100F | actagttgagatcctcaaggatgatag (SEQ ID NO: 13) |
| ND-ZJ-11815R | tatggtatcagggttggatacacc (SEQ ID NO: 22) |
| ND-ZJ-11648F | catgcaatgttgtccagagatg (SEQ ID NO: 14) |
| ND-ZJ-12591R | agctcataactcttgaagatagc (SEQ ID NO: 23) |
| ND-ZJ-12539F | tcagagagagatttcgcgagac (SEQ ID NO: 15) |
| ND-ZJ-14110R | cacagaatgcatggcaatcagg (SEQ ID NO: 24) |
| ND-ZJ-14021F | cattgtgacattgagattcctcc (SEQ ID NO: 16) |
| ND-ZJ-15118R | actgaatccgaatacgacttcc (SEQ ID NO: 25) |

In order to decrease an artificial mutation during PCR reaction, Pwo polymerase (Invitrogen co.) with a DNA repairing function was used. Further, the PCR product was purified by a soluble purification kit (Boehringer Mannheim Co.) or by an agarose gel purification kit (Qiagen Co.).

Figure 1:
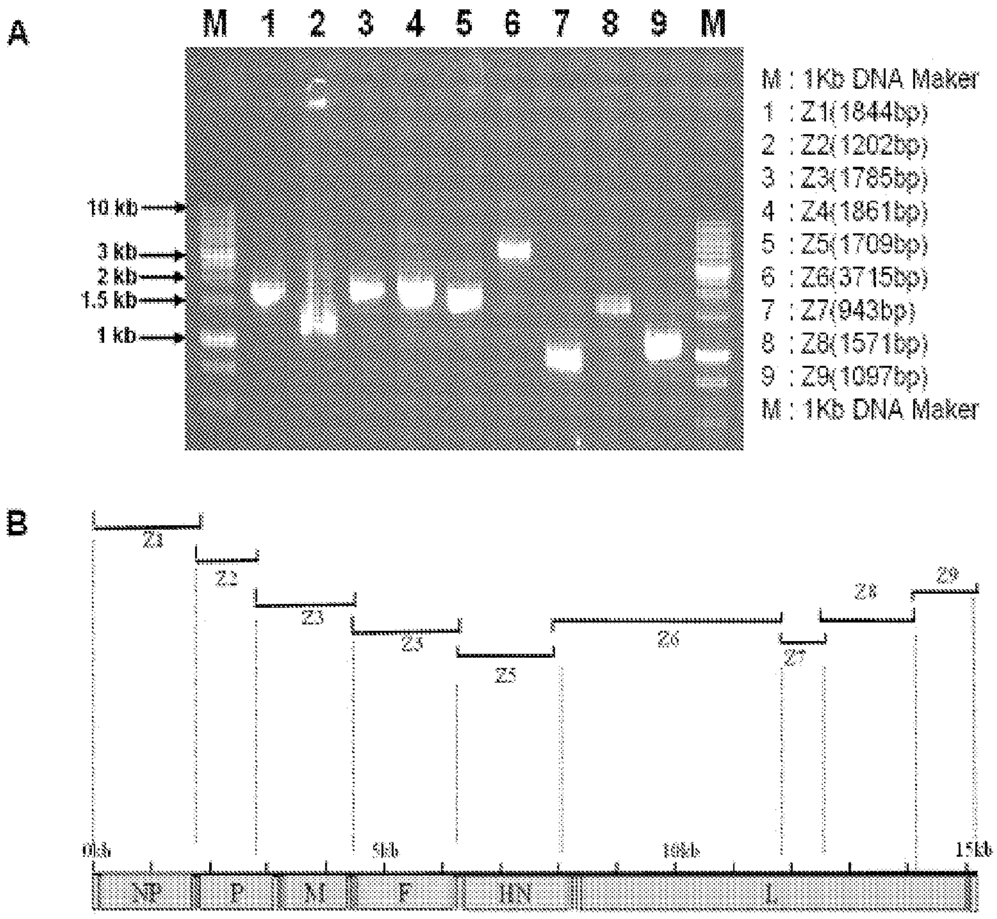
FIG. 1 shows a RT-PCT result, and the name and the location of the amplified RT-PCR products using genome RNA of the domestic velogenic Newcastle disease virus, KBNP-4152.

The location of the products obtained by RT-PCR for the KBNP-4152 viral gene is shown in FIG. 1.

The 9 kinds of purified products were cloned into TA vector such as XL-Topo, pCR8/GW/Topo or pcDNA3.1V5 Topo vector (Invitrogen co.), and more than three clones were obtained, respectively. Then, the plasmid of the clones was prepared, and the nucleotide sequence of the plasmid was determined.

All nucleotide sequences were determined using a cyclic sequencing kit (PRISM Ready Reaction Dye terminator kit) and an automated DNA sequencer (ABI310, Applied Biosystems Co.).

The primer used for the nucleotide sequence analysis was an M13 forward primer and an M13 reverse primer, respectively. In the case of fragments that were not read by the primer, the nucleotide sequence was analyzed using primer shown in Table 3 according to a primer walking method.

TABLE 3

Primers used for analyzing a nucleotide sequence of KBNP-4152 virus

| Primer | Primer sequence (5'->3') |
|---|---|
| ND-ZJ-597F | ctgacactctggaaagaatcc (SEQ ID NO: 26) |
| ND-ZJ-3421F | gatccagcgc cttgattcgt (SEQ ID NO: 27) |
| ND-ZJ-8662F | caggtgtttagaagaactggc (SEQ ID NO: 28) |
| ND-ZJ-5759F | cctcctggtatcatatcgca (SEQ ID NO: 29) |
| ND-ZJ-4679 | gtaacaggagataaggcagtc (SEQ ID NO: 30) |
| ND-ZJ-7670 | ttcttgtaccaacgagggtc (SEQ ID NO: 31) |
| ND-ZJ-9328F | cctacaggagctcaaagacac (SEQ ID NO: 32) |
| ND-ZJ-9977F | ctaagagatgacagtgtggc (SEQ ID NO: 33) |
| ND-ZJ-10588F | acttgctgcagcaagatctc (SEQ ID NO: 34) |
| ND-ZJ-13052F | gtggtctcaggcttatatgc (SEQ ID NO: 35) |

Figure 2:
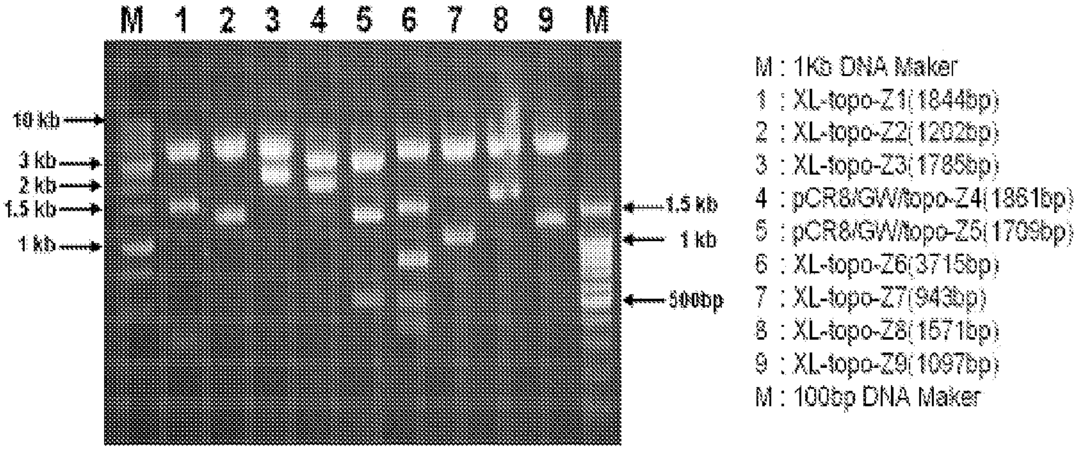
FIG. 2 shows a result of cloning the amplified product of FIG. 1 into a TA-cloning vector.
Figure 3:
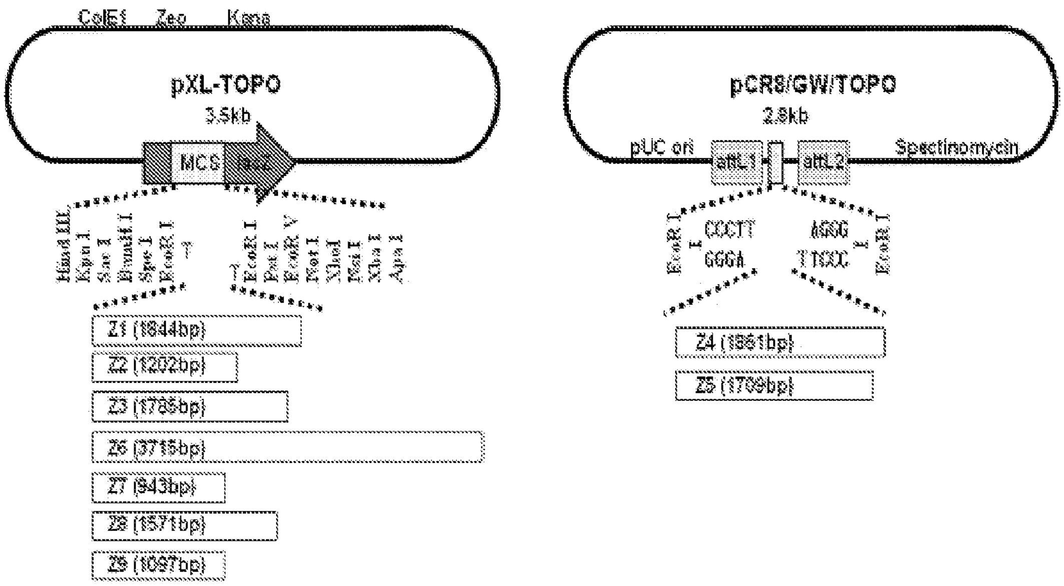
FIG. 3 shows a result of cloning the amplified product of FIG. 1 into a TA-cloning vector.

The TA-cloning vectors as described above are shown in FIG. 2B, and the size of fragments inserted in the vector that was treated with EcoRI is shown in FIG. 2A using PCR.

The KBNP-4152 strain showed the highest nucleotide sequence homology and amino acid sequence homology against SF02 derived from geese in China, and particularly in the case of NP, P, M, and L among the viral protein, the homology was more high than about 98%, but in the case of P, V, and HN, relatively low homology of about 97.6% and 95.0% was shown. The sequence homology results are shown in Table 4.

TABLE 4

Sequence homology between the KBNP-4152 strain and other stains

| KBNP-4152 | NP aa[a] (nt[b]) | P aa (nt) | V aa (nt) | M aa (nt) | F aa (nt) | HN aa (nt) | L aa (nt) |
|---|---|---|---|---|---|---|---|
| VII(SF02) (AF473851) | 99.2 (97.1) | 96.2 (97.6) | 95.0 (96.8) | 98.6 (98.0) | 98.4 (97.6) | 97.6 (97.6) | 98.9 (98.0) |
| VII(ZJ-1) (AF431744) | 99.0 (97.0) | 94.7 (97.1) | 92.9 (95.7) | 98.1 (97.4) | 97.7 (97.5) | 97.9 (97.7) | 98.9 (98.0) |
| Ulster (AY562991) | 94.1 (87.2) | 81.6 (83.1) | 75.5 (79.0) | 89.1 (86.6) | 90.3 (86.2) | 89.9 (84.4) | 94.3 (87.2) |
| La Sota (AY845400) | 91.3 (84.5) | 80.9 (81.6) | 76.3 (78.6) | 87.4 (84.7) | 88.8 (84.2) | 88.5 (81.7) | 92.0 (85.9) |

[a]a percentage of amino acid sequence homology (%)

[b]a percentage of nucleotide sequence homology (%)

Particularly, it may be considered that mutation on the V protein hindering the expression of interferon in cells is large, because the mutation of amino acid is accumulated in the process of overcoming defense system in the cells. Further, it may be considered that mutation on the HN protein is relatively large, because viruses having the mutation of a specific amino acid are selected in the process of avoiding humoral immune response as known in the mutation of linear antigen. The amino acid sequences and the nucleotide sequences of the each gene of the KBNP-4152 strain were registered in GenBank (Accession No. DQ839397). Besides, the change of cysteine residues and N-linked glycosylation sites of HN and F proteins, the change of amino acids affecting the structure and polarity of the HN protein, and the change of amino acids affecting structure and polarity of the F protein were measured. The changes are shown in Table 5 to 7.

TABLE 5

The change of cystine residues and N-liked glycosylation sites of HN and F protein

| | HN | | | F |
|---|---|---|---|---|
| | C1 (123) | G5 (508) | G6 (538) | C2 (27) |
| La Sota | − (W) | − | + | + |
| SNU4152 | + | + | + | −(R) |
| SNU0202 | + | + | − | −(R) |

TABLE 6

| The change of amino acids affecting structure and polarity of HN protein | | | | | | | | | | | | | | | |
|---|---|---|---|---|---|---|---|---|---|---|---|---|---|---|---|
| | (508-510) | 60 | 128 | 256 | 269 | 293 | 310 | 323 | 340 | 347 | 354 | 384 | 479 | 494 | 495 |
| KBNP-4152 | NVS | L | C | G | S | K | D | D | H | K | K | K | H | D | E |
| VII(SL03) | NIS | S | — | — | — | — | — | N | — | — | M | — | — | — | — |
| VII(consensus) | NIS | S | — | — | — | — | — | N | — | E | M | — | — | — | — |
| Ulster | SIS | P | — | E | — | E | N | N | Y | E | M | E | Y | — | K |
| La Sota | STS | P | W | E | R | G | S | N | Y | E | M | E | Y | G | V |
| VGGA | STS | P | W | E | R | G | S | N | Y | E | M | E | Y | G | — |

[a]Not done.

TABLE 7

| The change of amino acids affecting structure and polarity of F protein | | | | | | | | | | | | | | | |
|---|---|---|---|---|---|---|---|---|---|---|---|---|---|---|---|
| | 27 | 76 | 104 | 112 | 115 | 145 | 192 | 195 | 232 | 247 | 403 | 422 | 430 | 480 | 486 |
| KBNP-4152 | R | C | G | R | K | N | N | R | Q | N | D | H | D | S | S |
| VII(consensus) | — | — | — | — | — | — | — | — | — | D | — | — | — | R | — |
| Ulster | C | F | E | G | G | — | K | Q | — | D | — | Q | — | K | — |
| La Sota | C | — | E | G | G | K | K | Q | K | D | N | Q | G | K | R |
| VGGA | C | — | E | G | G | K | K | Q | K | D | N | Q | G | K | R |

As shown in the results, it is confirmed that the KBNP-4152 strain used in the present invention has a genotype similar with genotype VII, and the strain has a genetic difference with other type of viruses including the previous vaccine strain, the La Sota strain.

Example 2

Preparation of a Recombinant Vector for Transcription of Newcastle Disease Virus (NDV) Genome Using La Sota Strain as a Backbone 2.1. Design and Construction of a Parental Vector (pTMH) of Expressing Newcastle Disease Virus (NDV)

For manufacturing a virus from NDV cDNA, the cDNA has to be transcribed as the same structure with the virus genome without adding an unnecessary base to both the 5'- and 3'-termini of the virus genome. To obtain this structure, a parental vector pTMH having features as follows was manufactured (SEQ ID NO: 84):

1) A T7 promoter was positioned in front of the transcriptional initiation site (refer to FIG. 1 and FIG. 4).

2) A hepatitis delta virus (HDV) ribozyme sequence was positioned at the back of NDV antigenomic sequence, to occur self cleavage.

3) A multi-cloning Site (MCS) used for cloning the NDV genome was finally positioned between the T7 promoter and the HDV ribozyme (refer to FIG. 4).

4) Used the origin of replication (ori) of pBR322, to make the cloning vector stablely exist in *Escherichia coli*, even though the whole NDV antigenome corresponding to about 15 kb nucleotide sequences was included.

5) two different restriction enzyme recognition sites, BsmB I and Bsa I were positioned between the T7 promoter and the 5'-terminus of the antigenome in which transcription of the NDV was initiated, and positioned between the HDV ribozyme and the 3'-terminus of the antigenome in which transcription of the NDV was terminated, specifically to make cause transcription of both terminals of the viral genome from the NDV antigenome.

As shown in FIG. 4, 1.5 pmol of each of the TM p2 primer and the TM p3 primer among the TM p1-p4 primers used for manufacturing the linker, 30 pmol of each of the TM p1 primer and the TM p4 primer, 5 μℓ of 10×PCR buffer, 5 μℓ of 2.5 mM dNTPs, and 2.5 U of Taq polymerase were mixed, and then DW was added to the mixture to make the total volume 50 μℓ. Then, the mixture was reacted at 94° C. for 1 min, followed by 25 cycles at 90° C. for 30 sec, at 55° C. for 45 sec, and at 72° C. for 15 sec, and then further reacted at 72° C. for 5 min. After confirming the PCR amplicon, it was cloned into a pCR8/GW/Topo TA cloning vector, and the obtained clone having complete nucleotide sequences was named a pCR-TM vector.

By the PCR method using F and R primers of the HDV, and a pTV vector (received from Ph. D Park M H of Mogam Biotechnology Research Institute) as a template, the fragments including HDV ribozyme and T7 terminator regions were amplified, the obtained fragments were also cloned into a pCR/GW/Topo TA cloning vector, and the obtained clone having complete nucleotide sequences was named pCR-HDV.

The HDV fragment obtained by cutting the pCR-HDV vector with restriction enzymes, Bsa I and Nde I and the pCR-TM vector by cutting with the same restriction enzymes was ligated with T4 DNA ligase, which was transformed into a Top 10F' competent cell. Then, the obtained transformed vector was name as pCR-TMH. For stablely cloning the vector to *Escherichia coli*, the T7 promoter-MCS-HDV ribozyme region of the pCR-TMH vector treated by restriction enzymes, EcoR I and Nde I was subcloned into a pBR322 vector (Promega Co., Cat. #D1511), and the obtained clone was named a pTMH vector (SEQ ID NO: 84).

Figure 5:
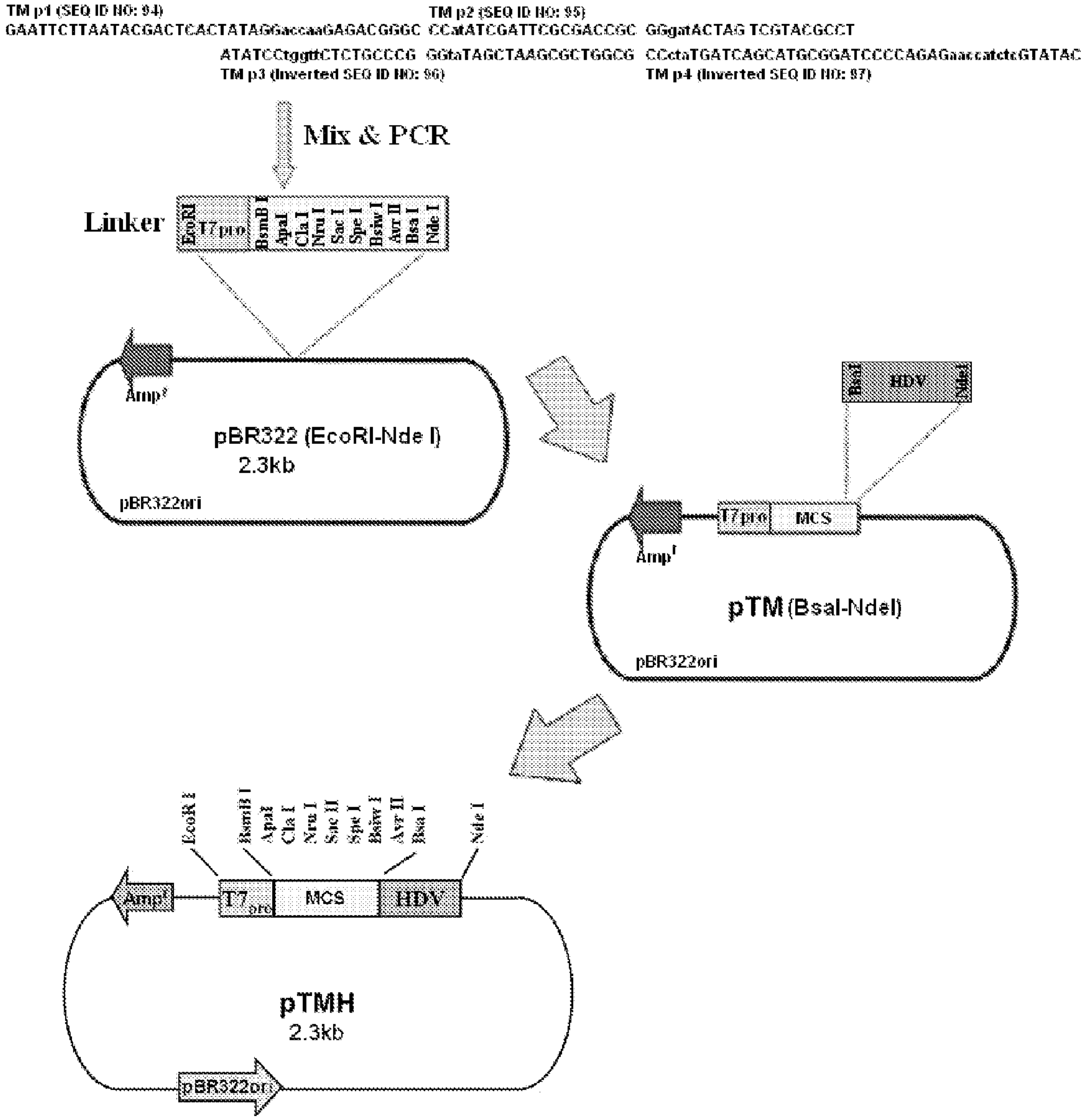
FIG. 5 shows a schematic diagram of a process of manufacturing the pTMH vector.
Figure 6:
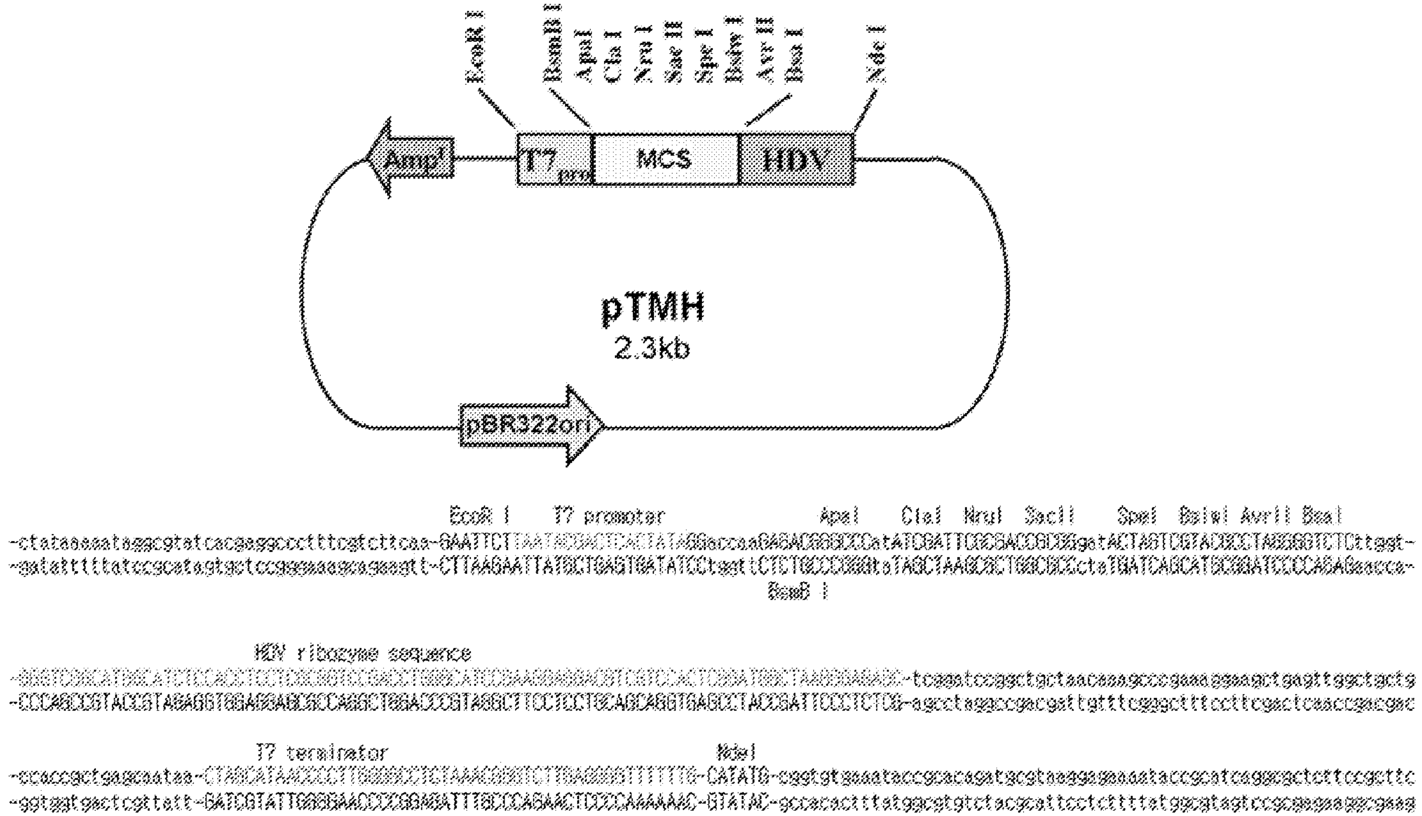
FIG. 6 shows nucleotide sequences of the main site in the pTMH vector.

A schematic diagram of a process of manufacturing the pTMH vector is shown in FIG. 5, a general cleavage map and nucleotide sequences of the parental vector pTMH are shown in FIG. 6, and nucleotide sequences of the manufactured pTMH vector are shown in FIG. 7.

In an embodiment of the present invention, the restriction enzyme recognition sites of the manufactured parental vector, pTMH are as follows:

| (No site found) |
|---|
| AccI AflII AgeI AvaI BclI BglII BsaAI BsaBI BsmF I BsmI BspMI BssHII BstBI BstEII Bsu36I EagI EcoRV HindIII HpaI KpnI Mfe I MluI NaeI NcoI NheI NotI NsiI PmeI PvuII SalI SfiI SmaI SphI XbaI Xcm I XhoI XmaI |

| (One site found) | | | | | |
|---|---|---|---|---|---|
| XmnI | 1959 | SspI | 2166 | SpeI | 64 |
| SacII | 55 | | | | |
| SacI | 175 | RsrI | 0 | PstI | 1605 |
| NspI | 471 | | | | |
| NruI | 49 | NdeI | 293 | HincII | 1903 |
| FspI | 1584 | | | | |
| EcoRI | 0 | EaeI | 1752 | ClaI | 43 |
| BstXI | 155 | | | | |
| BsmB I | 30 | BsiWI | 70 | Bmr I | 1404 |
| BglI | 1478 | | | | |

-continued

| | | | | | |
|---|---|---|---|---|---|
| BanI | 1312 | BamHI | 181 | AvrII | 76 |
| AseI | 1535 | | | | |
| Apo I | 0 | ApaI | 35 | AlwNI | 882 |
| AflIII | 471 | | | | |
| (Two sites found) | | | | | |
| StyI | 76, 256 | RsaI | 71, 1843 | HaeII | 345, 715 |
| ApaLI | 785, 2031 | AatII | 147, 2282 | Bsa I | 82, 1431* |

2.2. Cloning of the Whole cDNA of La Sota Strain

RNA extraction and cDNA synthesis for the La Sota/46 strain (AY845400) were performed by the method according to Example 1.

2.2.1. PCR of NDV Full-Length cDNA

Based on GenBank data, the whole NDV cDNA corresponding to 15,186 bp nucleotide sequences was amplified by PCR reaction using a primer set shown in Table 8 by the method according to Example 1, and cloned.

TABLE 8

Primers used for cloning the whole genomic gene of the La Sota strain

| Primer | Primer sequence (5'->3') |
|---|---|
| S1-F | cgtctcgaccaaacagagaatccgtgagttacg (SEQ ID NO: 36) |
| S1-R | ccat**gggccc** tttttagcat tggacg (SEQ ID NO: 37) |
| S2-F | aaaa**gggccc** atggtcgagc cc (SEQ ID NO: 38) |
| S2-R | tatc**atcgat** catgccgaca gtg (SEQ ID NO: 39) |
| S3-F | catg**atcgat** gataaaccca agc (SEQ ID NO: 40) |
| S3-R | **tcgcga**atgagccggt cgggatccag ac (SEQ ID NO: 41) |
| S4-F | **tcgcga**cgcaatatgg ctccaaactt tc (SEQ ID NO: 42) |
| S4-R | **ccgcgg**tagaacggat gttgtgaagc ctaa (SEQ ID NO: 43) |
| S5-F | **ccgcgg**caccgacaac aagagtcaat catg (SEQ ID NO: 44) |
| S5-R | ctca**actagt** aagggaacga tcctaaattc c (SEQ ID NO: 45) |
| S6-F | **actagt** tgagat cctcaaggat gatag (SEQ ID NO: 46) |
| S7-R | gatc**cgtacg** aatgcagctg aactc (SEQ ID NO: 47) |
| S9-F | **cctagg** tatt accaaactca aaga (SEQ ID NO: 48) |
| S9-R | **GGTCTC**aaccaaacaaa gatttggtga atg (SEQ ID NO: 49) |

Figure 8:
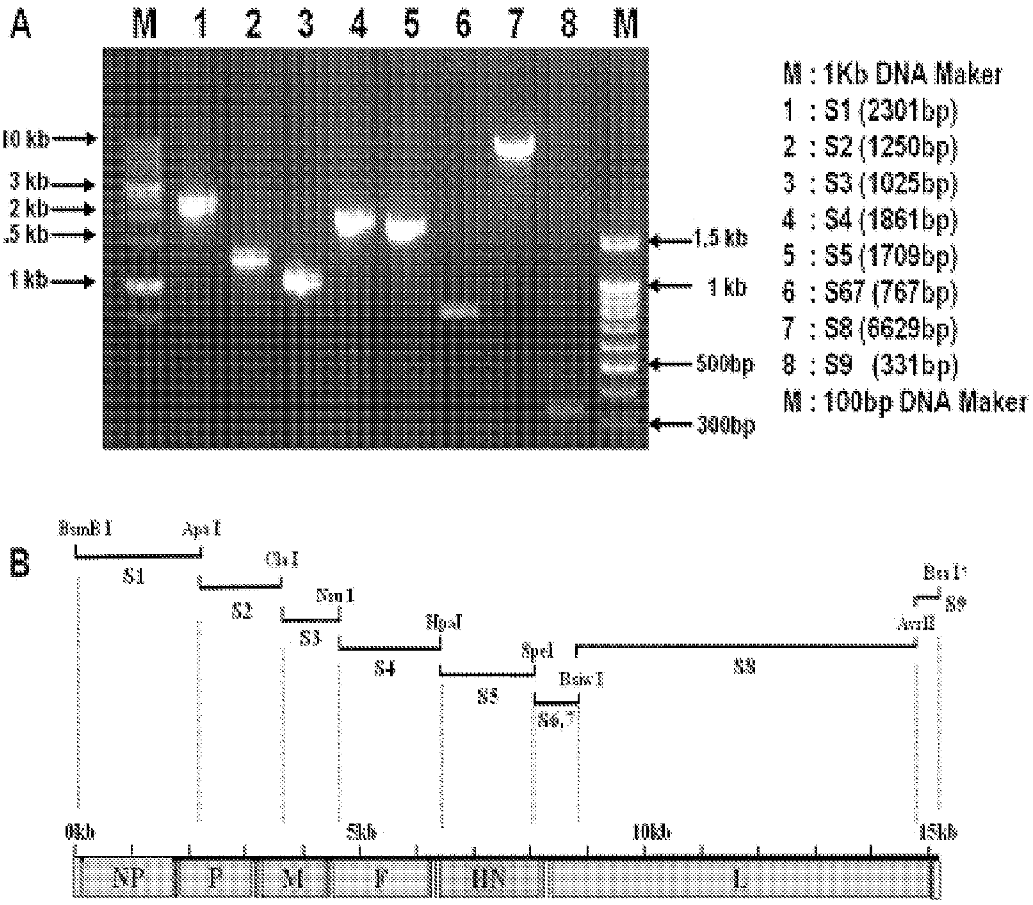
FIG. 8 shows a RT-PCT result, and the name and the location of the amplified RT-PCR products using genomic RNA of the La Sota strain.

The location of the products obtained by RT-PCR for the La Sota strain gene is shown in FIG. 8.

Figure 9A:
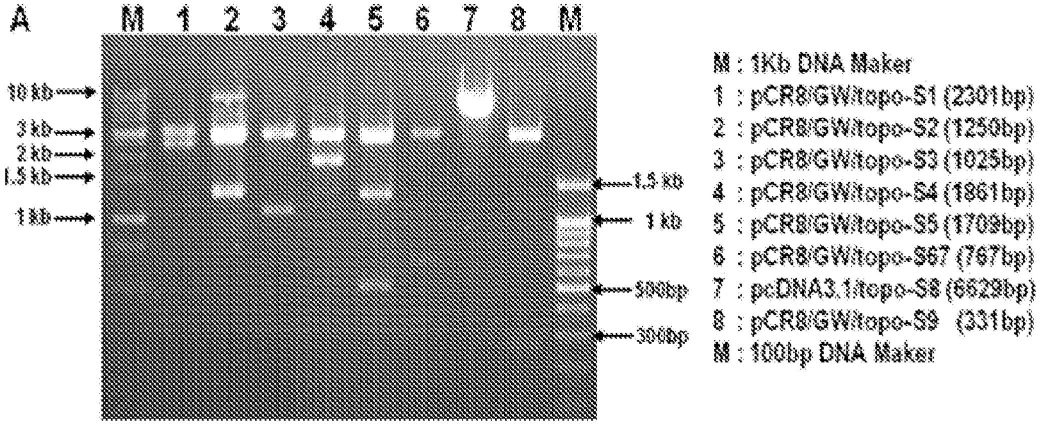
FIGS. 9A and 9B show a result of cloning the amplified product of FIG. 8 into a TA-cloning vector.
Figure 9B:
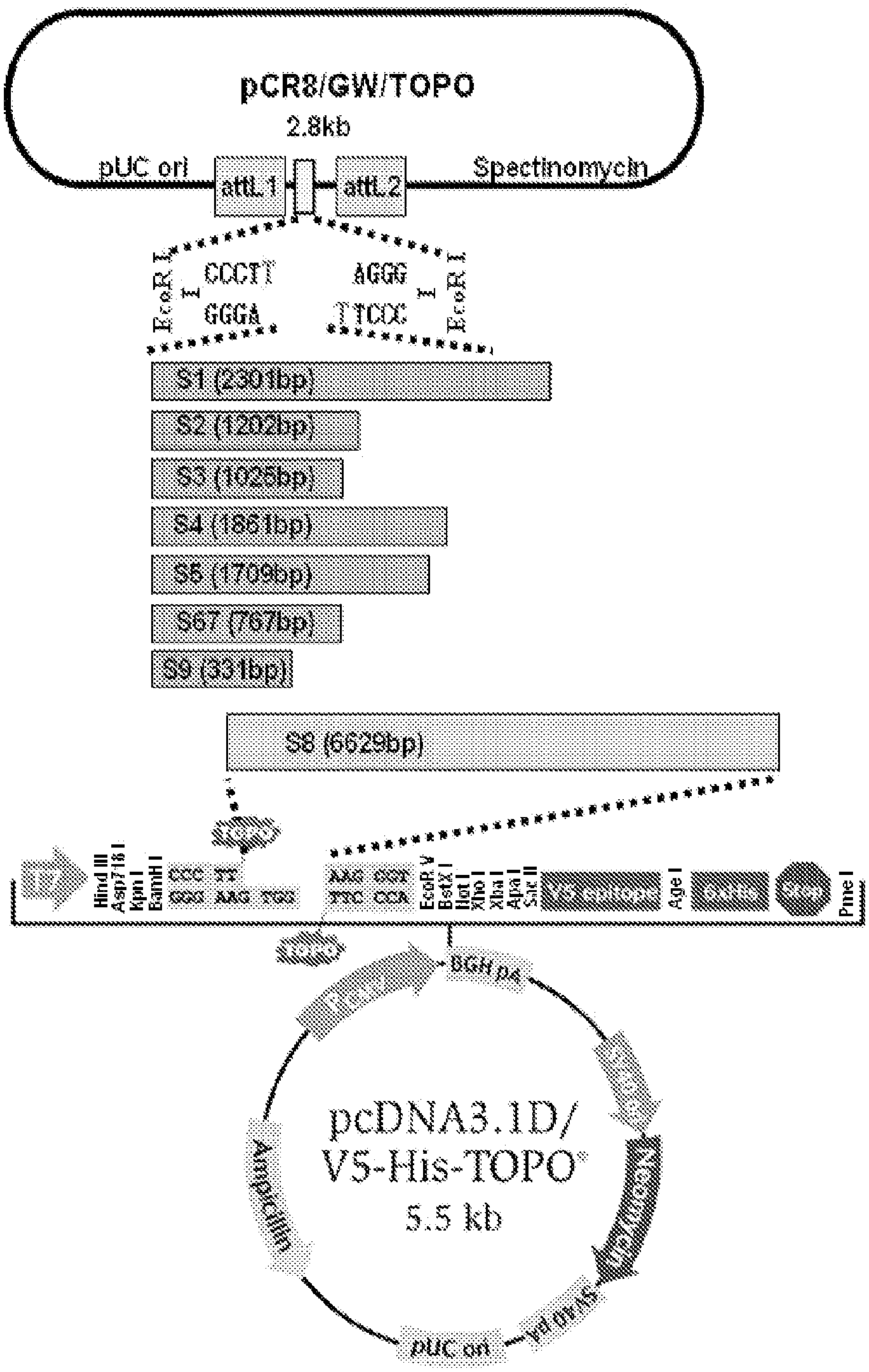

A diagram of vector inserted 8 parts of the La Sota strain gene into TA-cloning vector, respectively, is shown in FIG. 9A, and the size of fragments inserted in the vector that was treated with EcoRI is shown in FIG. 9A using PCR.

2.2.2. Cloning and Sequence Analysis of NDV Full-Length cDNA

After the amplified PCR product was assessed by electrophoresis on an agarose gel, the obtained gel was purified by GenClean III™ (Qbio Co.), and cloned with a Topo cloning kit (Invitrogen) or an XL-Topo cloning kit (Invitrogen). All nucleotide sequences of each obtained clone were analyzed using primers such as M13 forward, M13 reverse, etc. on the vector, or using primers shown in Table 9. As a result, clones having the same nucleotide sequence as the previous known La Sota strain, namely those in which no mutation occurred, were selected.

TABLE 9

| Primers used for analyzing a nucleotide sequence of La Sota strain genome | |
|---|---|
| Primer | Primer sequence (5'->3') |
| La-601 | taccctggagaggatcctc (SEQ ID NO: 50) |
| La-1261 | cgagctaaagctaaccccag (SEQ ID NO: 51) |
| La-1901 | agatgcagagatcgacgagc (SEQ ID NO: 52) |
| La-2581 | aggcgatatcacagagagta (SEQ ID NO: 53) |
| La-3271 | gtgccccaattgtgccaag (SEQ ID NO: 54) |
| S6-F-La | actagttgagatcctcaaagatgacgg (SEQ ID NO: 55) |
| S6-R-La | tgctctgccctttcaggaccggagctcgccatg (SEQ ID NO: 56) |
| S7-F-La | catggcgagctccggtcctgaaagggcagagca (SEQ ID NO: 57) |
| La-5121 | cagctcaggaattagactgc (SEQ ID NO: 58) |
| La-5711 | gtcatcgccaactgcaagat (SEQ ID NO: 59) |
| La-7042 | ctccggacatctgcaacag (SEQ ID NO: 60) |
| La-8591 | aaactcggaagggcagtac (SEQ ID NO: 61) |
| La-9311 | ttcgcattcaacctgcagg (SEQ ID NO: 62) |
| La-9971 | cttagagatgacaatgtggc (SEQ ID NO: 63) |
| La-10661 | gtaagatcagacgactctcc (SEQ ID NO: 64) |
| La-11321 | tttgagactgttgcaagcc (SEQ ID NO: 65) |
| La-12012 | tgtcgccacatgtaaaggc (SEQ ID NO: 66) |
| La-12721 | tacccgaaattggatcagtg (SEQ ID NO: 67) |
| La-13339 | catgtctcggaagagcctc (SEQ ID NO: 68) |
| La-13981 | atctgcagtgccctacaga (SEQ ID NO: 69) |
| La14976 | acagtaactgtgactcttaacgaaaatcacatattaataggctcc (SEQ ID NO: 70) |
| La15020R | ggagcctattaatatgtgattttcgttaagagtcacagttactgt (SEQ ID NO: 71) |
| S7-R | gatccgtacgaatgctgctgaactc (SEQ ID NO: 72) |
| NDV-Pt-R | tgccactgmtagttgygata (SEQ ID NO: 73) |
| NDcomF156 | atacacctcrtcycagacag (SEQ ID NO: 74) |
| La-8892R | gagccatgcaaacttggctgtggacc (SEQ ID NO: 75) |
| La-14708 | acagtgcacgagacagatcc (SEQ ID NO: 76) |
| La-15092R | gtcctaaggagtcagggttc (SEQ ID NO: 77) |

Figure 10B:
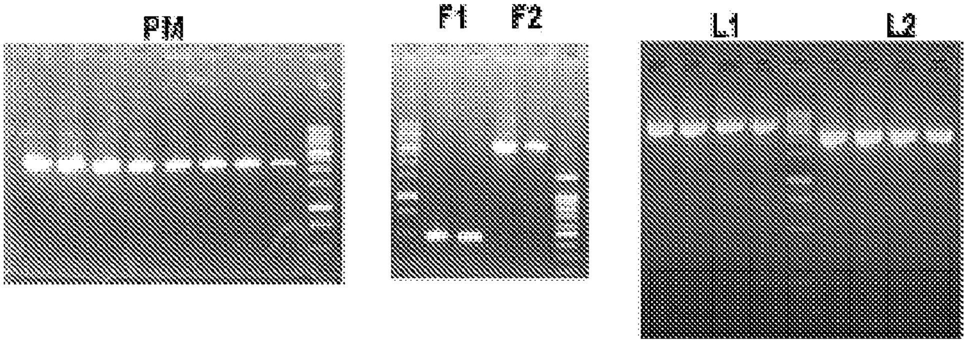

All clones in which no mutation occurred in the nucleotide sequence were sequentially cloned into multi-cloning sites of the parental vector pTMH, respectively, as shown in FIG. 10A and FIG. 10B. Also, a new restriction recognition site was introduced between L genes. The cloning process is shown in FIG. 10A.

2.2.3. Preparation of a Vector for Expression of NP, P and L Proteins Used for Forming RNP Complex To prepare a vector for expression of NP, P and L proteins of the Newcastle virus, the NP, P, and L genes of the La Sota strain were amplified by RT-PCR reaction using primers shown in Table 10, respectively, and the amplified product was cloned into TA-cloning vector. After sequencing analysis for the clones, only clones in which no mutation occurred in the nucleotide sequence were treated with NotI, and subcloned into the NotI site of the pcDNA6N5 vector.

TABLE 10

Primers used for amplifying and cloning of NP, P, and L genes of La Sota strain

| Primer | Primer sequence (5'->3') |
|---|---|
| NDV-NP-F | gagcggccgc-accatgagtacgagcagctcc (SEQ ID NO: 78) |
| NDV-NP-R | gagcggccgc-tcagtacccccagtcggtg (SEQ ID NO: 79) |
| NDV-P-F | gagcggccgc-accatggccacctttacagatg (SEQ ID NO: 80) |
| NDV-P-R | gagcggccgc-ttagccatttagagcaaggc (SEQ ID NO: 81) |
| NDV-L-F | gagcggccgc-accatggcgagcctccgatcctgaaa (SEQ ID NO: 82) |
| NDV-L-R | gagcggccgc-ttaagagtcacagttactgtaatatcc (SEQ ID NO: 83) |

Figure 11:
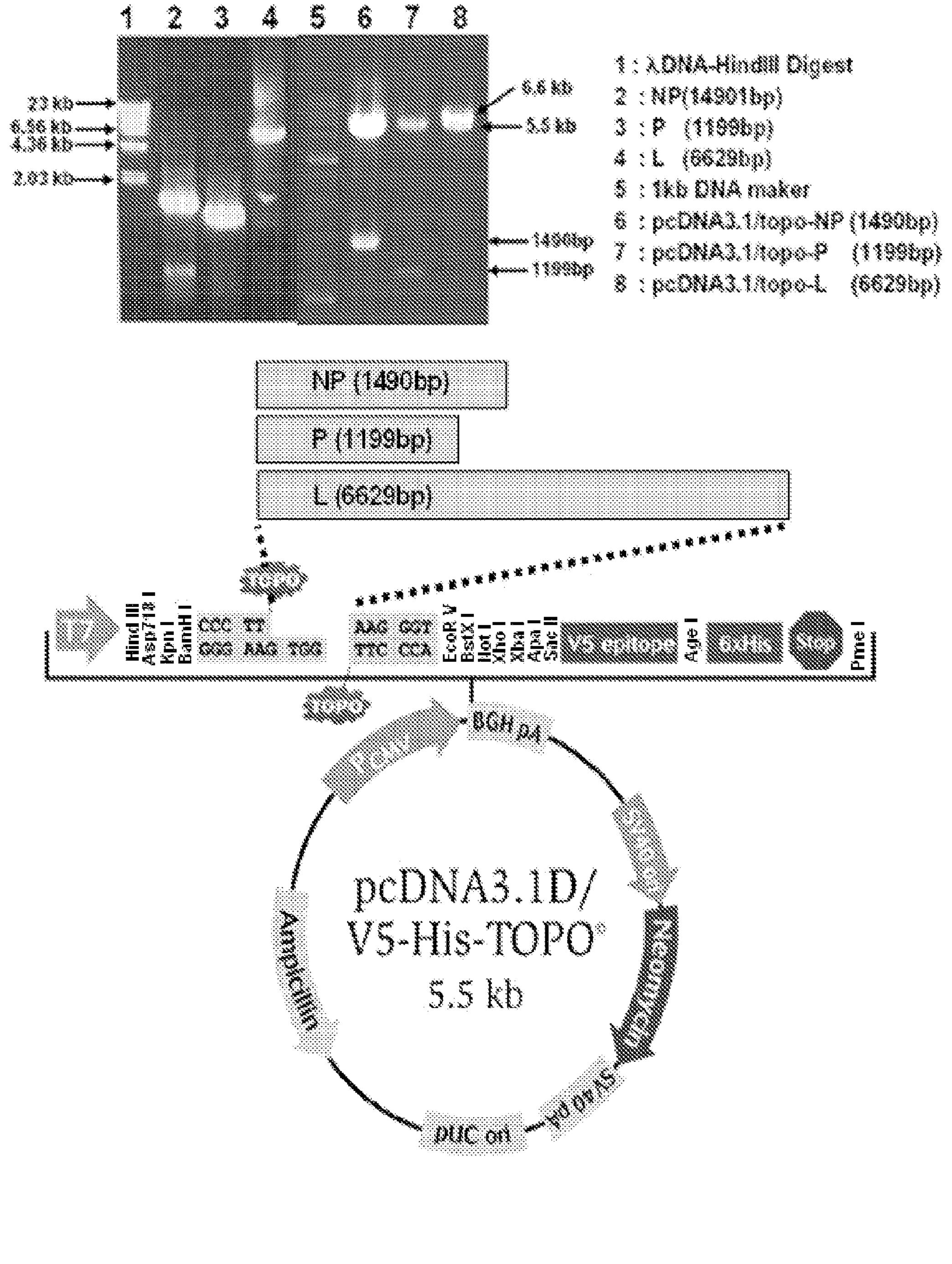
FIG. 11 shows a process of manufacturing plasmid for expressing the NP, P and L genes of NDV, wherein lanes 2, 3 and 4 of A indicate a RT-PCR result of NP, P and L genes, respectively, lanes 6, 7 and 8 of A indicate a gene inserted in a vector that is treated with NotI after cloning the NP, P and L genes into a pcDNA3.1/TOPO vector, respectively, and B indicates a schematic diagram outlining this.
Figure 12:
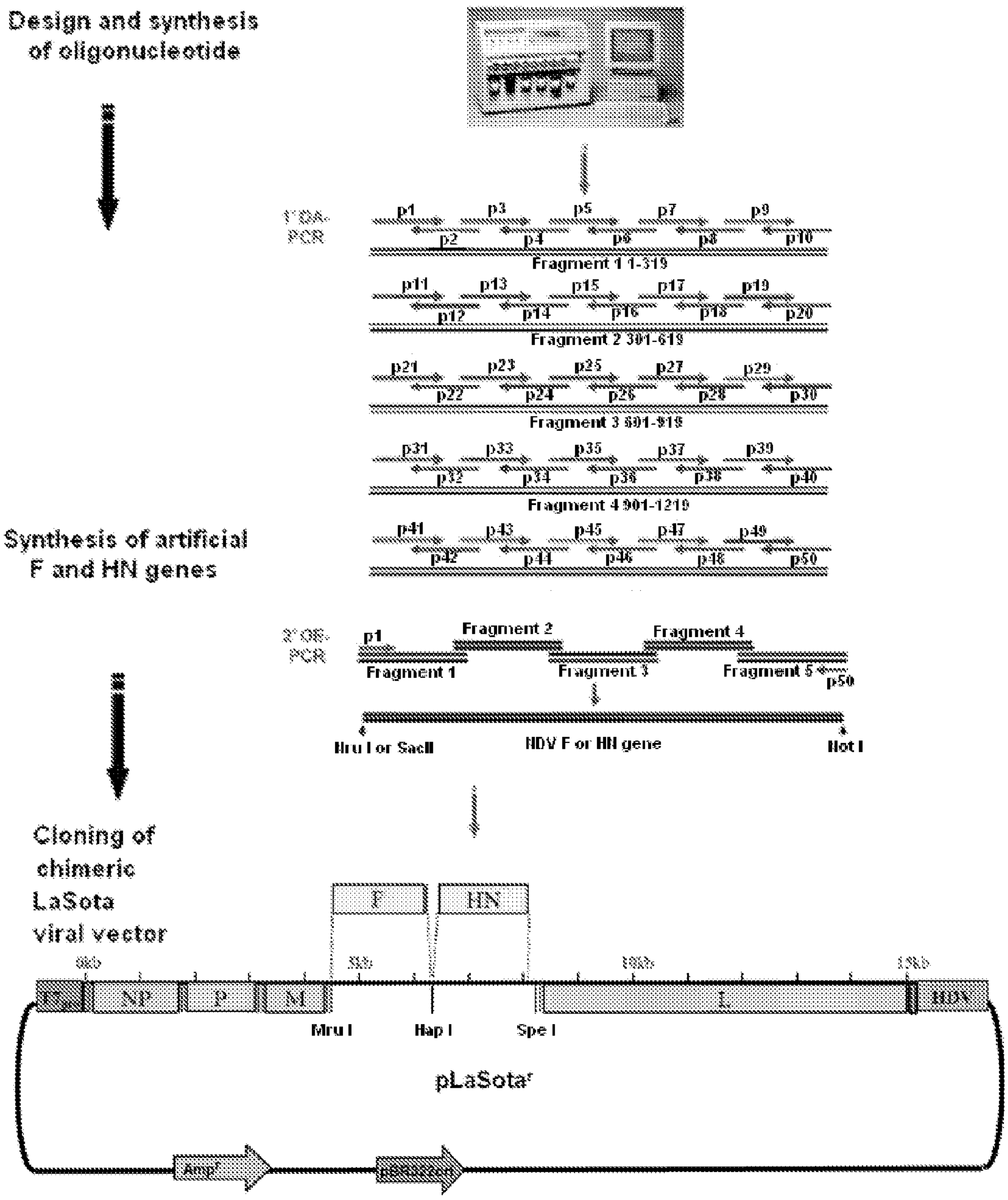
FIG. 12 shows a semi-synthesis process of the F and HN genes using s PTDS technique.

The amplified products for NP, P, and L genes obtained by RT-PCR are shown in FIG. 11A. Each gene was cloned into a TA-cloning vector, and the clones in which no mutation occurred in the nucleotide sequence were selected by sequencing analysis. The selected clones are shown in FIG. 11B.

2.3. Preparation of a Recombinant Lentogenic NDV with a Surface Antigen of Velogenic Field NDV 2.3.1. Preparation of a Recombinant Clone Attenuating F and HN Gene of Velogenic KBNP-4152

In an embodiment of the present invention, a recombinant vector for transcription of the NDV genome wherein F and HN gene of the velogenic Newcastle disease virus, KBNP-4152 that is recently prevalent domestically was inserted in a vector for transcription of the La Sota strain (rNDV) using the La Sota strain as a backbone, which is manufactured.

2.3.2. Synthesis of a Recombinant Viral Gene

Each of the modified F and HN gene was obtained using site-directed mutagenesis or PTDS (PCR DNA synthesis) (Xiong, A. S. et al., 2004, Nucleic Acids Research, Vol 32, No. 12 e98). The manufacturing process is shown in FIG. 12 to 15.

(A) A gene having a 3'-terminus of the La Sota M gene, a linker of the KBNP-4152 F gene, and a modified nucleotide sequence of the cleavage site of KBNP-4152 F gene were synthesized.

For manufacturing a recombinant virus, two genes having genomic sequences of the La Sota strain up to the 3'-terminus of the M gene, and having nucleotide sequences of KBNP-4152 up to the intergenic sequence and gene start sequence, were fused (refer to FIG. 13). For attenuating the F gene, the gene was mutated so that occurred the codons for the amino acids located at the cleavage site encoded one or two basic amino acids (i.e., changed from 112-RRQKRF-117 into 112-GRQARL-117). As shown in FIG. 14, primers were synthesized, and primers combined according to the arrow direction were added. Then, the gene was artificially synthesized by site-directed mutagenesis and PTDS.

(B) Then, KBNP-4152 HN (1-569) gene and an HN gene terminus (570-577) of the La Sota strain were connected. As a result, nucleotide sequences of the connected sites were as follows (SEQ ID NO: 85, the underlined part is an HN C-terminus coding sequence of the La Sota strain).

cccttACTAGTTGAGATTCTCAAGGATGATGGGGTTAGGGAGGCCA
GGGCTGGCCGCTT

GAGTCAATTGCGAGAGGGTTGGAAAGATGACATTGTATCACCTAT
CTTTTGCGACGCCAA

-continued

GAATCAAACTGAGTACCGGCGTGAGCTCGAGTCTTACGCTGCCAG
CTGGCCATAATCAGC

TAGCGCTAATGTGATTAGATTAAATCTTGTCGATAGTCACTTGATT
AAGAAAAAATGTAA

GTGGCAATGAGATACAAGGCAAAACAGCTCATGGTAAATAATAC
GGGTAGGACATGGCGA (C) As described above, for connecting the KBNP-4152 HN (1-569) gene and HN gene terminus (570-577) of the La Sota strain, primers were designed as shown in FIG. 15, and PTDS was performed.

2.3.3. Chimera NDV (KBNP-C4152R2L) Rescue

After culturing a HEp-2 (Korea Collection for Type Cultures) or BHK21 (received from Ph. D Park M H of Mogam Biotechnology Research Institute) cell line at 80% confluence in 6-well plates (37° C., 5% CO2), vaccinia T7 virus (received from Ph. D Park M H of Mogam Biotechnology Research Institute) was infected. For forming an RNP complex of NDV on the cell line, the three expression plasmid, pcDNA3.1-NP, pcDNA3.1-P and pcDNA3.1-L vector (FIG. 11B) for expression of NP, P and L genomic genes, and the one transcription vector of NDV genome, pTMH C4152-R2L (SEQ ID NO: 1, refer to FIG. 23), were prepared. To manufacturing a recombinant vector, pTMH C4152-R2L, attenuated F gene and the HN (1-569) gene of KBNP-4152 were inserted between the intergenic sequence site at the back of M gene and the 570th amino acid encoding site in the HN gene of the La Sota strain genome.

10 μℓ of Lipofectamine™ (Invitrogen Co.) was mixed with 4 μg of plasmid DNA mixed with each plasmid vector at the ratio of 1:1:0.1:1, and transfected to HEp-2 cell line. Then, 1

μℓ/ml of acetylated trypsin was added to the culture medium. The cell line was cultured in 6-well plates at 37° C. for 2-3 days, and the cultured cells and culture medium were harvested and performed 3 times of quick freezing and quick defrost. Then, the cells and the culture medium were inoculated into SPF embryonated eggs at 9-11 days old, and allantoic fluid of the embryonated egg was harvested. As a result, a Newcastle disease virus from the allantoic fluid was obtained, and the virus was named a KBNP-C41152R2L strain. The KBNP-C41152R2L strain was deposited with the Korean Collection for Type Culture (Korea Research Institute of Bioscience and Biotechnology, Taejon, Republic of Korea) on Sep. 12, 2006, and assigned deposition No. KCTC10984BP.

Figure 16:
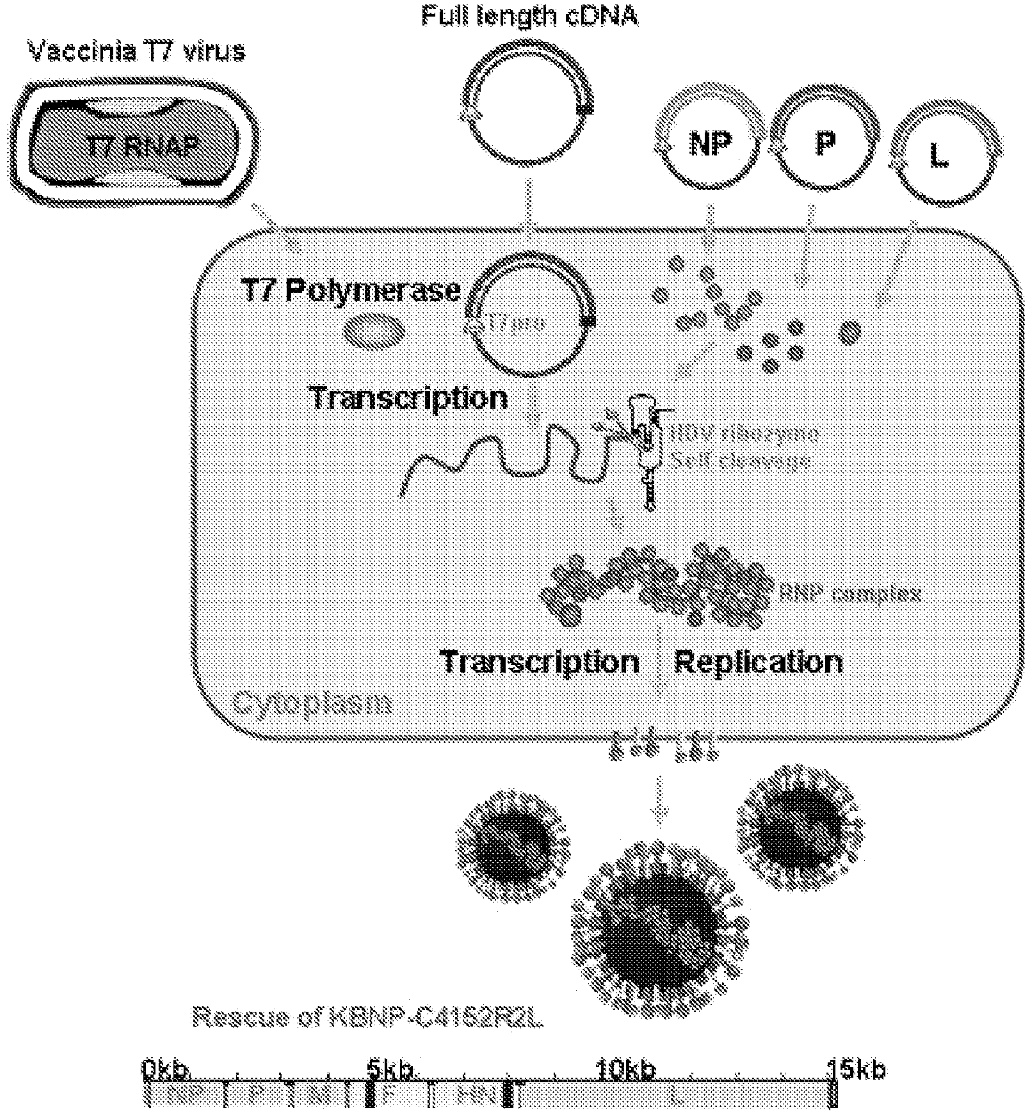
FIG. 16 shows a process of manufacturing the recombinant virus, KBNP-C4152R2L.

The process of manufacturing the KBNP-C4152R2L virus is shown in FIG. 16.

According to the same method as described above, velogenic NDV (named RRQKRF; KBNP-4152R4L) having 4 of basic amino acids and lentogenic NDV (name GGQARL; KBNP-C4152R1L) having 1 of basic amino acid at a cleavage site of the F protein were manufactured, respectively. The name of the strain was determined according to the number of basic amino acids of a cleavage site of the F protein, wherein the number at the back of R indicates the number of basic amino acids among 112 to 116 amino acids, and L (long) indicates the length of HN protein having 577 amino acids similar to the La Sota strain.

Figure 17:
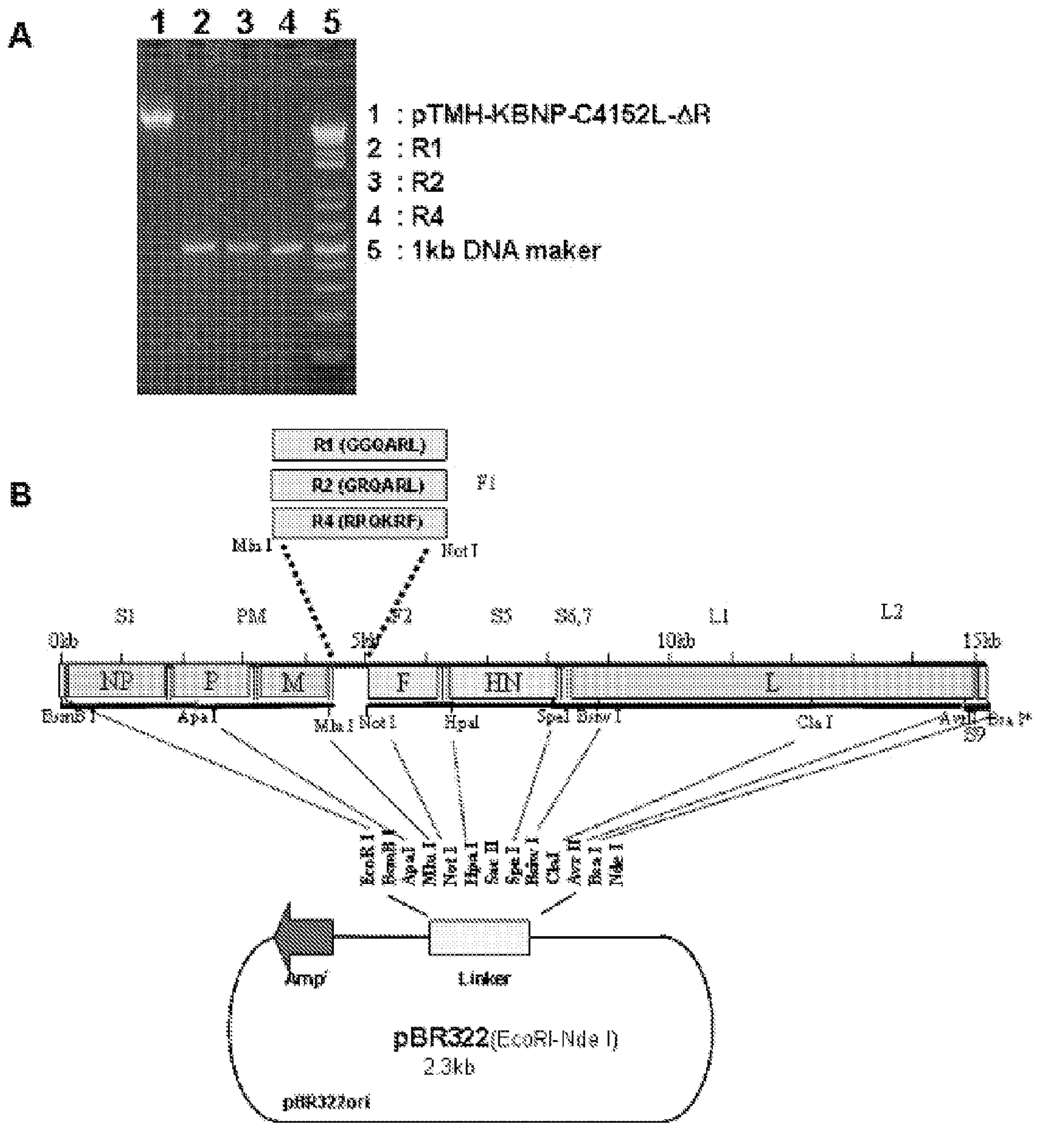
FIG. 17 shows a process of manufacturing a clone of a recombinant virus with various furin-like enzyme recognition sites.

Achematic diagram of the obtained KBNP-C4152R1L, KBNP-C4152R2L and KBNP-C4152R4L is shown in FIG. 17.

Example 3

Figure 18:
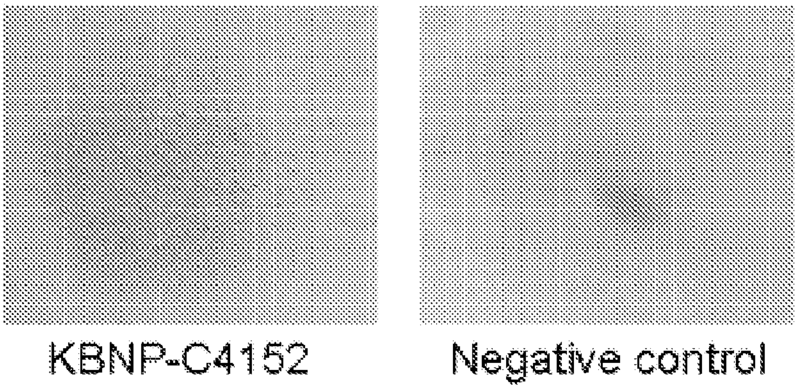
FIG. 18 is a result of showing whether KBNP-C4152R2L inoculated into a chicken embryo is increased or not by using a plate hemagglutination test.

Analysis of a KBNP-C4152R2L 3.1. General Characteristics Analysis of Chimera NDV The obtained KBNP-C4152R2L was inoculated into SPF embryonated eggs at 9-10 days old, and allantoic fluid of the embryonated egg was harvested after 3-5 days. Then, it was confirmed whether the recombinant NDV grows or not by using a plate hemagglutination test. The results are shown in FIG. 18. As shown in FIG. 18, hemagglutination was observed in the allantoic fluid obtained from the embryonated egg inoculated with KBNP-C4152R2L, and consequently the growth of KBNP-C4152R2L was confirmed.

Figure 19:
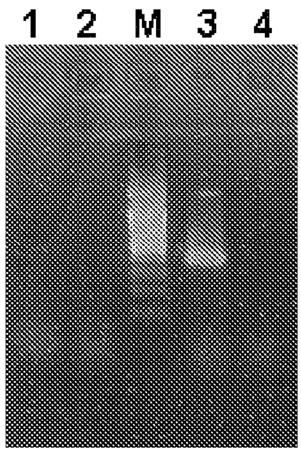
FIG. 19 shows a pathotype-specific RT-PCR result for confirming the pathogenicity of KBNP-C4152R2L.

KBNP-C4152R2L is the same as the KBNP-4152 wherein most of the F and HN genes are field velogenic, but it is a virus wherein the cleavage site of the F protein is artificially attenuated. Particularly, the viral RNA was not detected by PCR using a velogenic NDV-specific primer, but was detected by PCR using all NDV common detecting primers. This fact was confirmed by a gene marker of the recombinant NDV through determining the amplified viral RNA sequences obtained by RT-PCR using NDV-pt-R and NDVcomF156 primers shown in Table 5. By the RT-PCR method, the chimera virus was detected, and the pathogenic type (pathotype) was confirmed. The results are shown in FIG. 19. As shown in FIG. 19, KBNP-C4152R2L is detected by PCR using NDV commonly primer (NDVcomF156), but is not detected by PCR using a pathogenic strain-specific primer (NDV-pt-R) (Korea Patent No. 0451883).

Figure 20:
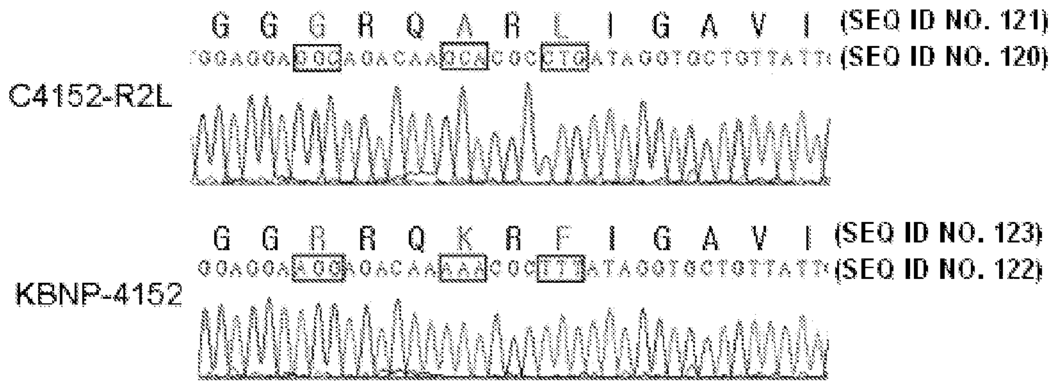
FIG. 20 is a result of comparing a nucleotide sequence of the furin-like enzyme recognition site of the F protein of KBNP-4152 and KBNP-C4152R2L.

For identifying the virus in more detail, the nucleotide sequence of the virus was analyzed after RT-PCR, and the nucleotide sequence coding the cleavage site of the F gene which is artificially synthesized was confirmed. The results are shown in FIG. 20. As shown in FIG. 20, the cleavage site of the F protein of parental strain, KBNP-4152 has a structure of 112-RRQKRF-117, but KBNP-C4152R2L has a structure of 112-GRQARL-117. Particularly, NDV in nature does not have the alanine (A) at the $115^{th}$ amino acid position, but the chimer virus of the present invention has the alanine. This is a feature of the present invention of only the chimera virus.

3.2. Serologic Characteristics Analysis of Chimera NDV

Figure 21:
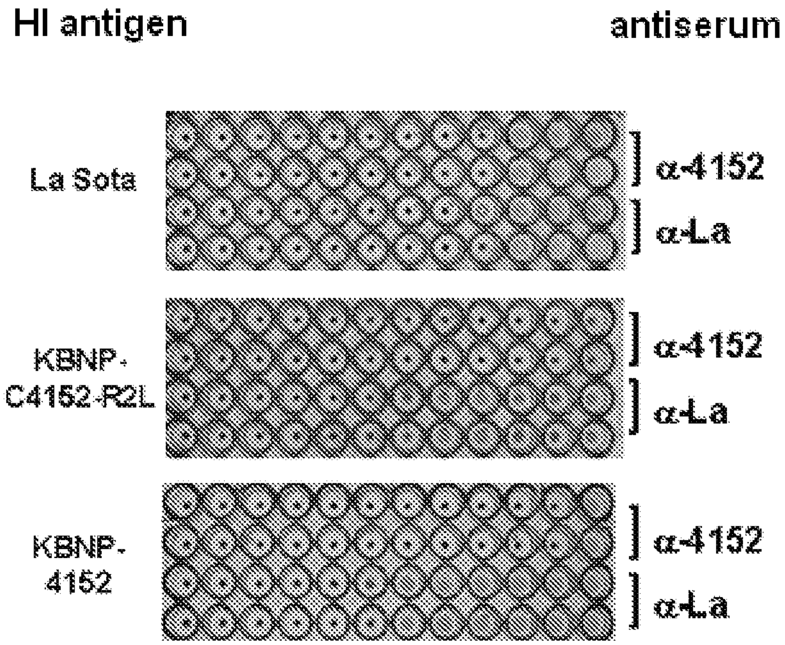
FIG. 21 shows an antigenic relationship among the La Sota strain, KBNP-4152 and KBNP-C4152R2L by using a cross hemagglutination inhibition test.

Because F and HN of KBNP-C4152R2L are similar to KBNP-4152 but are clearly different from the La Sota strain, it is expected that KBNP-C4152R2L is serologically similar to KBNP-4152 but different from the La Sota strain. In order to confirm this, serologic characteristics were analyzed by using a cross hemagglutination inhibition test. The results are shown in FIG. 21. As shown in FIG. 21, serologically KBNP-C4152R2L is similar with KBNP-4152. That is, when compared with the La Sota strain, anti-serum of anti-La Sota showed 4 to 8 times lower hemagglutination units in the KBNP-C4152R2L and KBNP-4152, and anti-serum of anti-KBNP-4152 showed nearly quite similar hemagglutination units in the oneself or KBNP-C4152R2L.

3.3. Pathogenicity Index Measurement of a KBNP-C4152R2L 3.3.1. Mean Death Time (MDT) Measurement MDT measurement was performed according to the method of Alexander (1998). The KBNP-C4152R2L virus diluted with $10^{-6}$ was inoculated into two groups of 5 embryonated eggs per group. The first group was inoculated at 9 A.M., and the second group was inoculated at 5 P.M. After inoculation, the eggs were incubated at 37° C. for 7 days, and checked embryo-death-time at 9 A.M. and 5 P.M. each day. Then, mortality time was recorded and MDT (mean death time) was calculated. If the measured MDT was shorter than 60 h, the virus was determined as velogenic, if the measured MDT is 60-90 h, it was determined as mesogenic, and if the measured MDT is 90-120 h, it was determined as lentogenic, and if the measured MDT is more than 120 hours, it was determined apathogenic. MDT of a vaccine virus must be more than 90 h. Consequently, the average mortality time of the KBNP-C4152R2L was measured at more than 168 h, so the KBNP-C4152R2L was classified as apathogenic NDV.

3.3.2. Intracerebral Pathogenicity Index (ICPI) Measurement

After inoculating 50 μℓ of allantoic fluid (Example 2.3.3.) diluted with sterile saline 10-fold into intracerebrally into 1 day-old chicks (n=10) using a 1 cc syringe, a normal chick is marked as 0, a chick showing a disease symptom was marked as 1, and a killed chick was marked as 2, respectively. Then, the overall score of each group obtained over 8 days was divided by 80. In the results, apathogenic was classified as 0.0-0.2, lentogenic was classified as 0.2-0.5, mesogenic was classified as 1.0-1.5, and velogenic was classified as 1.5-2.0. For utilizing the virus as a vaccine virus domestically, because the pathogenicity index must be less than 0.5, a recombinant virus having 0.0-0.5 of pathogenicity index was selected.

The results of measurements of KBNP-4152, KBNP-C4152R2L and ICPI of the La Sota strain are shown in Tables 11 to 13, respectively.

TABLE 11

ICPI measurement of KBNP-4152

| | Day | | | | | | | | |
|---|---|---|---|---|---|---|---|---|---|
| | 1 | 2 | 3 | 4 | 5 | 6 | 7 | 8 | Sum(index) |
| Sign | 6 | 0 | 0 | 0 | 0 | 0 | 0 | 0 | 6 × 1 |
| Dead | 4 | 10 | 10 | 10 | 10 | 10 | 10 | 10 | 74 × 2 |
| Normal | 0 | 0 | 0 | 0 | 0 | 0 | 0 | 0 | |
| | | | | | | | | Total = | 154 |

ICPI = 154/80 = 1.925

TABLE 12

| ICPI measurement of KBNP-C4152R2L | | | | | | | | | |
|---|---|---|---|---|---|---|---|---|---|
| | Day | | | | | | | | |
| | 1 | 2 | 3 | 4 | 5 | 6 | 7 | 8 | Sum(index) |
| Sign | 0 | 0 | 0 | 0 | 0 | 0 | 0 | 0 | 0 × 1 |
| Dead | 0 | 0 | 0 | 0 | 0 | 0 | 0 | 0 | 0 × 2 |
| Normal | 10 | 10 | 10 | 10 | 10 | 10 | 10 | 10 | |
| | | | | | | | | Total = | 154 |

ICPI = 0/80 = 0.0

TABLE 13

| ICPI measurement of La Sota strain | | | | | | | | | |
|---|---|---|---|---|---|---|---|---|---|
| | Day | | | | | | | | |
| | 1 | 2 | 3 | 4 | 5 | 6 | 7 | 8 | Sum(index) |
| Sign | 0 | 0 | 0 | 0 | 0 | 3 | 5 | 2 | 10 × 1 |
| Dead | 0 | 0 | 0 | 0 | 0 | 0 | 1 | 4 | 5 × 2 |
| Normal | 10 | 10 | 10 | 10 | 10 | 10 | 10 | 10 | |
| | | | | | | | | Total = | 20 |

ICPI = 20/80 = 0.25

According to the MDT and ICPI results, MDT of the KBNP-C4152R2L was more than 168 h, and ICPI of the KBNP-C4152R2L was 0.0. Therefore, the virus was confirmed as a virus without any pathogenicity. This result of the pathogenicity decrease indicates that the KBNP-C4152R2L strain of the present invention is attenuated more than the conventional vaccine strain, La Sota, and therefore the pathogenicity of the KBNP-C4152R2L strain is less than that of the La Sota strain. A sudden decrease of the pathogenicity in the cytopathic effect is capable of being shown in the recombinant virus introduced with the F and HN genes of velogenic field NDV strain having a granular cytopathic effect instead of the F and HN genes of the strain having an excellent syncytial formation capability. Thus far, it has been reported that a clone having a syncytial type and granular type of cytopathic effect among velogenic NDV exists. Further, it has been reported that the ICPI value (1.78) of the granular type of clone, SNU9358GG (AF535861) is less than the ICPI value (1.95) of syncytial type of NDV clone, SNU9358GS (received from Avian Disease & Laboratory, College of Veterinary Medicine of Seoul National University), and therefore the pathogenicity of the granular type of clone is less than that of the syncytial type of NDV clone. However, because the NDV clone having this granular type of cytopathic effect in the pathogenicity NDV with other genotypes III, IV, V, VIII, and XI including genotype VII was not previously known, the present inventors succeeded for the first time in cloning a granular type of NDV from the NDV with genotype VII, and manufacturing a recombinant NDV having pathogenicity of less than the La Sota strain having a granular type of cytopathic effect using F and HN genes of the virus.

3.4. Genetic Safety Test of a KBNP-C4152R2L

After sub-culturing a recombinant virus of the present invention, KBNP-C4152R2L on a chicken embryo more than 9 times, 4030-8889 nucleotide sequence of the chimera genome was amplified by RT-PCR and analyzed by DNA sequencing. As a result, the nucleotide sequence had no change on the nucleotide sequence, and it was confirmed as a very stable nucleotide sequence.

3.5. Productivity Measurement of a KBNP-C4152R2L: EID50 (50% Egg-Infectious Dose) Measurement After inoculating 0.1 ml of the virus diluted 10-fold with a sterile saline solution into the allantoic cavity of 5-7 chicken embryos at 9-10 days old, the inoculated chicken embryos were cultivated at 37° C. for 5-7 days. Then, the obtained chicken embryos were chilled, and the allantoic fluid from the chilled chicken embryos were harvested. Then, it was determined whether the virus increased or not by using hemagglutination, which was calculated according to a determined formula. As a result, EID50 of KBNP-C4152R2L was observed at 1010.1/mℓ, and the productivity of the virus was very high, similar to the previous La Sota strain.

3.6. Hemagglutination-Elution Pattern Measurement

The examination for hemagglutination-elution was performed according to the method of Spalatin (1970). Namely, 0.5 ml of each of the La Sota strain and KBNP-C4152R2L serially diluted with CMF-PBS in 2-fold and 0.25 ml of 1% chicken blood were mixed in micro-well plates. After incubating the plates at room temperature for 1 h, the hemagglutination titer was measured. After the $1^{st}$ reading, the plate was maintained at 24° C. for 24 h, and the hemagglutination titer was measured again. The plate was resuspended after 2 h, and the hemagglutination titer again was again measured. The titer was represented as the reciprocal of the hemagglutination-occurring maximal dilution factor. A method of determining the hemagglutination-elution pattern is as follows, when the hemagglutination-elution had completely occurred after hemagglutination at 24 h, and the hemagglutination had not occurred after resuspension at 2 h, the hemagglutination-elution pattern was determined as a rapid eluter, but determined as a slow eluter.

As a result, the La Sota strain was observed as a slow eluter, but the KBNP-C4152R2L was observed as a rapid eluter, indicating that the KBNP-C4152R2L has the same biological characteristics as the KBNP-4152.

3.7. Cytopathic Effect Measurement

Figure 22:
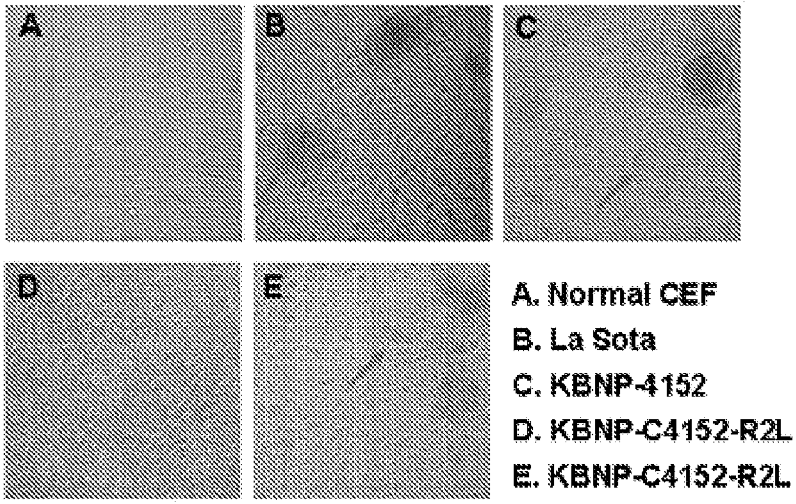
FIG. 22 shows a cytophatic effect of KBNP-C4152R2L.

After culturing chicken embryonic fibroblast (CEF) to form a single layer on 96-well plates, the La Sota strain, KBNP-4152 and KBNP-C4152R2L (each 200 TCID50/well) were infected into the cultured cells, respectively. Then, the culture medium was replaced with a medium containing 0.5% FBS and 20 μg/mℓ of trypsin. Observed results after culturing for 3 days, are shown in FIG. 22. The red arrow in the middle of FIG. 22 indicates the formation of syncytia of typical cytopathic effects of NDV. Practically, it was confirmed that KBNP-C4152R2L forms a specific syncytia of NDV when trypsin is added in the strain (the red arrow of FIG. 22).

This cytopathic effect indicates that the chimera virus is a lentogenic pathogenicity strain having trypsin dependency in the formation of syncytia. Further, the virus has a granular type of cytopathic effect as shown in FIG. 22D and without the formation of typical syncytia, different from the La Sota strain and the KBNP-4152 strain.

3.8. Killed Vaccine Test of a KBNP-C4152R2L

A chicken embryo culture medium of KBNP-C4152R2L, a 10-fold concentrated fluid obtained from the culture medium, and a chicken embryo culture medium of the La Sota strain were each inactivated by adding 0.3% formaldehyde. For manufacturing each of the killed vaccines, 30% of each of the inactivated viral antigen supernatants was mixed with 70% ISA70 oil. The manufactured killed vaccine was inoculated into the subcutaneous tissue of 6-week-old SPF chickens. After 3 weeks, a correction circumference 106TCID50 (AY6304009) used as a standard in Quarantine service was challenged into the nasal cavity and oral cavities. After the challenge, the mortality rate up to 10 days was observed. The results are shown in Table 14.

TABLE 14

Protection efficacy and immunogenicity of Chimera NDV vaccine

| Vaccine | Dose | | HI titer | | | Survival After |
|---|---|---|---|---|---|---|
| (killed oil) | HA unit | $EID_{50}$ | Test antigen | 6 DPV | 21 DPV | challenge |
| Control | — | — | La Sota | 0 | 0 | 1/10 |
| | | | C4152R2L | 0.2 ± 0.6 | 0 | (10%) |
| | | | KBNP-4152 | 0 | 0 | |
| C4152R2L | 20 | $10^{9.3}$ | La Sota | 0.3 ± 0.8 | 7.7 ± 1.3 | 15/15 |
| oil | | | C4152R2L | 0.2 ± 0.8 | 8.2 ± 0.9 | (100%) |
| | | | KBNP-4152 | 0.2 ± 0.8 | 7.7 ± 1.0 | |
| C4152R2L | 154 | $10^{9.9}$ | La Sota | 1.5 ± 1.4 | 7.7 ± 1.2 | 15/15 |
| oil | | | C4152R2L | 2.2 ± 1.4 | 8.9 ± 1.3 | (100%) |
| | | | KBNP-4152 | 2.2 ± 1.4 | 8.2 ± 1.3 | |
| BNE oil | 154 | $10^{9.5}$ | La Sota | 0.2 ± 0.6 | 6.9 ± 1.5 | 8/9 |
| | | | C4152R2L | 0 | 5.1 ± 1.4 | (89%) |
| | | | KBNP-4152 | 0 | 4.6 ± 1.5 | |

As shown in Table 14, even though the antigen amount of KBNP-C4152R2L calculated by HA titer is lower compared to the La Sota strain, the antibody formation capability of KBNP-C4152R2L is much better compared with previous vaccines. Particularly, the serological immunity against the field strain was better with the KBNP-C4152R2L compared to the La Sota strain.

3.9. In Ovo Vaccine Test of a KBNP-C4152R2L

KBNP-C4152R2L has lower pathogenicity than a strain used for the current vaccine, and its possibility for in ovo vaccine is high. For confirming this, in ovo vaccine was inoculated into 18 day-old chicken embryos, and the hatching rate and the rate of weight gain obtained after hatching at 2 weeks were compared with a control group. By examining the antibody titer of the inoculated chicken embryos at 2 weeks old or more, it was determined whether maternal antibodies were overcome or not, and the immunity levels were compared. After 2 weeks, the velogenic virus was challenged into the chicken embryos, and the rate of protection against the virus was determined.

Chicken embryo used for the test was conventional laying hen chicks, and 0.1 cc of each diluted vaccine strain ($10^{7.0}$ $EID_{50}$/ml) was inoculated into the chicken embryos at 18 days of age. A negative control group was inoculated with 0.1 cc of sterile PBS. To confirm the level of maternal antibodies, 5 chicken embryos of a negative control group were euthanized immediately after hatching and the serum of the euthanized chicken embryos was obtained. After 17 days of age, individual weights for each group were measured and blood was drawn. Then, a virulent stain KBNP-4152 ($10^{6.5}$ $EID_{50}$) was inoculated into nasal cavities and oral cavities thereof. After the attack inoculation, the survival rate to 10 days was observed. The results are shown in Table 15.

TABLE 15

Comparison of in ovo vaccine effect of a KBNP-C4152R2L
Hatchability and protection of chickens inoculated with chimera NDV, strain,
KBNP-C4152R2L at 18 day of embryonation against velogenic NDV, challenge.

| | Dose | Survival from hatching | Mean Weight | Mean HI titer ($log_2$) | | | Survival |
|---|---|---|---|---|---|---|---|
| Vaccine (live) | $log_{10}$ $EID_{50}$/egg | to 17 day-old | at 17 day-old | Test antigen | at 1 day old | at 17 day-old | After Challenge |
| Control | — | 23/27 (85.2%) | 201 ± 17.8 g | La Sota | 5.8 ± 2.7 | 2.7 ± 1.7 | 12/18 |
| | | | | C4152R2L | — | 1.8 ± 1.3 | (66.7%) |
| C4152R2L | 6.1 | 17/20 (85.0%) | 204 ± 42 g | La Sota | — | 4.9 ± 1.1 | 17/17 |
| | | | | C4152R2L | — | 5.5 ± 1.4 | (100%) |
| La Sota | 6.0 | 4/20 (20.0%) | — | La Sota | — | 6.8 ± 2.2 | 4/4 |
| | | | | C4152R2L | — | 5.0 ± 1.4 | (100%) |

As shown in Table 15, the KBNP-C4152R2L inoculation group and the negative control group had no statically significant difference in hatching rate and rate of weight gain. However, the antibody titer at 17 days after hatching was higher in the KBNP-C4152R2L inoculation group compared with the control group. That is, in the case of the control group, the hemagglutination inhibition (HI) titer of the maternal antibody at 1 day versus the La Sota strain was decreased by 2.7±1.7 from an average of 5.8±2.7. On the other hand, in the case of the KBNP-C4152R2L inoculation group, the HI titer of maternal antibody at 1 day versus the La Sota strain was 4.9±1.1, and showed a relatively higher HI titer of 5.5±1.4. Further, after challenge, a mortality rate of 33% was observed in the control group, but a survival rate of 100% was observed in the recombinant vaccine inoculation group.

These results are excellent compared to "U.S. Pat. No. 6,699,479B1" of the title "Recombinant Newcastle disease virus as an embryo vaccine" by Akzo Nobel N/6 V (NL) Company, and is significant in that the vaccine is obtained from KBNP-C4152R2L developed by a new method without using attenuation according to P gene editing.

Recently, developed countries have preferred in ovo vaccines that are capable of directly vaccinating chicken embryos before hatching, because these vaccines have the simplicity of inoculation and economy. However, there has been a limit in live vaccine strains known thus far that are applied to Newcastle disease, because the strains have pathogenicity with respect to chicken embryos. On the other hand, it is confirmed that KBNP-C4152R2L of the present Invention has no pathogenicity in the chicken embryos, and it is expected that the value of applying the KBNP-C4152R2L as in ovo vaccine is very high.

As described above, the Newcastle disease virus of the present invention has similar antigenicity to the velogenic Newcastle disease virus that is prevalent both domestically and in Asia as a whole. Further, because the Newcastle disease virus of the present invention has similar or significantly low pathogenicity compared with currently used vaccine strains, the vaccine can be used as in ovo vaccine. In addition, the possibility of acquisition of pathogenicity by point mutation is significantly lower compared with previous vaccine strains. Therefore, the Newcastle disease virus of the present invention can be used in manufacturing killed vaccine, a live vaccine and in ovo vaccine for preventing Newcastle disease in both domestically and in Asia overall.

What is claimed is:

1. A strain of Newcastle disease virus, comprising nucleotide sequences encoding NP, P, M, and L proteins of a low-pathogenic Newcastle disease virus AY845400; and nucleotide sequences encoding F and HN proteins of a high-pathogenic Newcastle disease virus KCTC 10919BP, wherein the F protein coding sequence comprised in the strain is characterized by substitution of the codon encoding the $115^{th}$ amino acid of the F protein of the high-pathogenic Newcastle disease virus with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU.

2. A strain of Newcastle disease virus, comprising nucleotide sequences encoding NP, P, M, and L proteins of a low-pathogenic Newcastle disease virus AY845400; and nucleotide sequences encoding F and HN proteins of a high-pathogenic Newcastle disease virus KCTC 10919BP, wherein the F protein coding sequence comprised in the strain is characterized by substitution of the codon encoding the $115^{th}$ amino acid of the F protein of the high-pathogenic Newcastle disease virus with any one selected from the group consisting of alanine codons consisting of GCA, GCC, GCG and GCU; aspartic acid codons consisting of GAC and GAU; phenylalanine codons consisting of UUC and UUU; isoleucine codons consisting of AUC and AUU; leucine codons consisting of UUA and UUG; serine codons consisting of UCA, UCC, UCG and UCU; threonine codons consisting of ACC and ACU; valine codons consisting of GUA, GUC, GUG and GUU; and tyrosine codons consisting of UAC and UAU, wherein the HN protein is a recombinant HN protein having the amino acid sequences of $570^{th}$ and higher positions from the low-pathogenic Newcastle disease virus and the amino acid sequences from $1^{st}$ to $569^{th}$ positions from the high-pathogenic Newcastle disease virus.

3. The strain according to claim 1, wherein the strain is KCTC 10984BP.

4. A vaccine against Newcastle disease comprising the stain of Newcastle disease virus of claim 1.

5. A vaccine against Newcastle disease comprising the stain of Newcastle disease virus of claim 2.

6. The vaccine according to claim 4, wherein the strain is KCTC 10984BP.

7. The vaccine according to claim 4, wherein the vaccine is an inactivated killed vaccine or a live vaccine.

8. A method of delivering the vaccine of claim 4 to a subject, comprising delivering the vaccine to the subject in ovo.

9. The vaccine according to claim 5, wherein the vaccine is an inactivated killed vaccine or a live vaccine.

10. A method of delivering the vaccine of claim 5 to a subject, comprising delivering the vaccine to the subject in ovo.

* * * * *